United States Patent [19]
Bard et al.

[11] Patent Number: 6,083,705
[45] Date of Patent: Jul. 4, 2000

[54] DNA ENCODING HUMAN α 1 ADRENERGIC RECEPTORS AND USES THEREOF

[75] Inventors: Jonathon A. Bard, Wyckoff, N.J.; Richard L. Weinshank, New York, N.Y.; Carlos Forray, Paramus, N.J.

[73] Assignee: Synaptic Pharmaceuticals Corporation, Paramus, N.J.

[21] Appl. No.: 09/206,899

[22] Filed: Dec. 7, 1998

Related U.S. Application Data

[60] Division of application No. 08/406,855, filed as application No. PCT/US93/09187, Sep. 24, 1993, which is a continuation-in-part of application No. 07/952,798, Sep. 25, 1992, abandoned.

[51] Int. Cl.[7] .............................. C12Q 1/68; C07H 21/04
[52] U.S. Cl. ....................... 435/6; 435/69.1; 435/240.2; 435/320.1; 530/23.1
[58] Field of Search ........................ 435/6, 69.1, 240.2, 435/320.1; 530/23.1, 350

[56] References Cited

U.S. PATENT DOCUMENTS

| | | | |
|---|---|---|---|
| 4,616,017 | 10/1986 | Baldwin et al. | 514/252 |
| 4,661,491 | 4/1987 | Regnier | 514/260 |
| 4,873,191 | 10/1989 | Wagner et al. | 800/25 |
| 5,155,218 | 10/1992 | Weinshank et al. | 536/23.5 |
| 5,556,753 | 9/1996 | Bard et al. | 435/6 |
| 5,714,381 | 2/1998 | Bard et al. | 435/325 |

OTHER PUBLICATIONS

Cubbedu, L.X., *American Heart Journal* (1988) 116:133–162 (Exhibit 4).

Fraser, et al., "Autobodies and Monoclonal Antibodies in the Purification and Molecular Characterization of Neurotransmitter Receptors", *J. Cell. Biochem.* (1983) 21(3): 219–231 (Exhibit 5).

Ramarao, C.S., et al., "Genomic Organization and Expression of the Human $\alpha_{1B}$–Adrenergic Receptor" *J. Biol. Chem.* (1992) 267(30): 21936–21945 (Exhibit 6).

Adham, N., et al., "Cloning of another human serotonin receptor (5–HT$_{1F}$): A fifth 5HT$_1$ receptor subtype coupled to the inhibition of Adenylate cyclase", *Proc. Natl. Acad. Sci. USA* (1993) 90: 408–412.

Bruno, J.F., et al., Molecular cloning and sequencing of a cDNA encoding a human $\alpha_{1A}$–adrenergic receptor. Biochem. Biophys. Res. Com. 1991. 179(3): 1485–1490.

Cotecchia, et al., "Molecular cloning and expression of the cDNA for the hamster alpha 1–adrenergic receptor", *Proc. Natl. Acad. Sci.* (1988) 85: 7159–7163.

Cotten, M. and Birnstiel, M.L., Ribozyme mediated destruction of RNA in vivo, *EMBO J.* (1989) 8(12): 3861–3866.

DiBona, G.F., Hypertension and renal alpha adrenergic receptors, *FASEB J.* (1989) 3: 1993–1994.

Forray, C., et al., "The $\alpha_1$–Adrenergic Receptor that Mediates Smooth Muscle Contraction in Human Prostate Has the Pharmacological Properties of the Cloned Human $\alpha_{1C}$ Subtype" *Molecular Pharmacol.* (1994) 45: 703–708.

Gao, et al., "Isolation and characterization of the gene encoding the rat $\alpha_{1B}$ adrenergic receptor" *Gene* (1993) 131: 243–247.

Glover, D.M., Gene Cloning, Chapman & Hall, London 1984, p. 1–21.

Jones, C.R., et al., "Autoradiography of adrenoceptors in rat and human brain: α–adrenoceptor and idazoxan binding sites" *Progress In Brain Research* (1991) 88: 271–291.

Karson, E.M., et al., Prospects for human gene therapy, *J. Reprod. Med.* (1992) 37(6): 508–514.

Laz, T.M., et al., "The Rat Homologue of the Bovine $\alpha_{1C}$–Adrenergic Receptor Shows the Pharmacological Properties of the classical $\alpha_{1A}$ Subtype" *Molecular Pharmacol.* (1994) 46: 414–422.

Lerner, R.A., Tapping the immunological repertoire to produce antibodies of predetermined specificity, *Nature* (1982) 299: 592–596.

Link, R., et al., Cloning of Two Mouse Genes Encoding $\alpha_2$–Adrenergic Receptor Subtypes and Identification of a Single Amino Acid in the Mouse $\alpha_2$–C10 Homolog Responsible for an Interspecies Variation in Antagonist Binding, Molecular Pharmacology (1992) 42: 16–27.

Lomasney, J.W., et al., Molecular cloning and expression of the cDNA for the $\alpha_{1A}$–adrenergic receptor. *J. Biol. Chem.* 1991 266(10): 6365–6369.

Perala, M., et al., "Differential expression of two $\alpha_2$–adrenergic receptor subtype mRNAs in human tissues" *Molecular Brain Research* (1992) 16: 57–63.

Roemer, K. and Friedman, T., Concepts and strategies for human gene therapy, *Eur. J. Biochem.* (1992) 208.

Schwinn, D.A., et al., Molecular Cloning and Expression of the cDNA for a Novel $\alpha_1$–Adrenergic Receptor Subtype. *J. Biol. Chem.* (1990) 265:8183–8189.

Schwinn, D.A., and Lomasney, J.W., Pharmacologic characterization of cloned $\alpha_1$–adrenoceptor subtypes: selective antagonists suggest the existence of a fourth subtype, *Eur. J. Pharmacol.* (1992) 227(4): 433–436.

(List continued on next page.)

*Primary Examiner*—George C. Elliott
*Assistant Examiner*—Andrew Wang
*Attorney, Agent, or Firm*—John P. White; Cooper & Dunham LLP

[57] ABSTRACT

This invention provides an isolated nucleic acid, vectors, transformed mammalian cells and non-human transgenic animals that encode and express normal or mutant α 1a, α 1b and α 1c adrenergic receptor genes. This invention also provides a protein, and an antibody directed to the protein and pharmaceutical compounds related to α 1a, α 1b and α 1c adrenergic receptors. This invention provides nucleic acid probes, and antisense oligonucleotides complementary to α 1a, α 1b and α 1c adrenergic receptor genes. This invention further provides methods for determining ligand binding, detecting expression, drug screening, and treatments for alleviating abnormalities associated with human α 1a, α 1b and α 1c adrenergic receptors.

31 Claims, 37 Drawing Sheets

OTHER PUBLICATIONS

Voight, M.M., et al., Sequence of a rat brain cDNA encoding an alpha–1B adrenergic receptor. *Nucleic Acids Res.* (1990) 18(4): 1053.

Wagner, E., et al., Transferrin polycation DNA complexes: The effect of polycations on the structure of the complex and DNA delivery to cells, *Proc. Natl. Acad. Sci. USA* (1991) 88: 4255–4259.

Waspe, L.E., et al., The cardiac beta–myosin heavy chain isogene is induced selectively in alpha$_1$–adrenergic receptor–stimulated hypertrophy of cultured rat heart myocytes, *J. Clin. Invest.* (1990) 85(4): 1206–1214.

Weinshank, R.L., et al., "Human serotonin 1D receptor is encoded by a subfamily of two distinct genes: 5–HT$_{1D\alpha}$ and 5–HT$_{1D\beta}$" *Proc. Natl. Acad. Sci. USA* (1992) 89: 3630–3634.

Yakubov, L.A., et al., Mechanism of oligonucleotide uptake by cells: Involvement of specific receptors?, Proc. Natl. Acad. Sci. USA 1989 86:6454–6458.

Yang–Feng, T.L., et al., "Chromosomal organization of adrenergic receptor genes" Proc. Natl. Acad. Sci. USA (1990) 87: 1516–1520.

FIGURE 1A

| FIGURE 1A, 1/37 |
| FIGURE 1B, 2/37 |
| FIGURE 1C, 3/37 |
| FIGURE 1D, 4/37 |
| FIGURE 1E, 5/37 |
| FIGURE 1F, 6/37 |
| FIGURE 1G, 7/37 |
| FIGURE 1H, 8/37 |
| FIGURE 1I, 9/37 |

```
        -170            -150            -130
         .               .               .
-176  CCGGGCCAGGCACGTCTCCGCTCTCGGACACAGCCGTCACAGGAACTTGGGCAGGAC  -117

-110             -90             -70
         .               .               .
-116  CCGACGGGACCCCGTGCGCGGAGCTGCATCTGGAGCCCCGCGGCTATGCCCTGTGCTCCCC  -57

-50             -30             -10
          .               .               .
 -56  TCCTGCCGGCCGCTCGTTCTGTGCCCCGGCCCCGGCCACCGACGGCCGCGTTGAGATG    3
 -18                                                        M     1

10              30              50
           .               .               .
   4  ACTTTCCGCGATCTCCTGAGCGTCAGTTTCGAGGACCCCGCGGACAGCAGCCAGGG    63
   2   T  F  R  D  L  L  S  V  S  F  E  G  P  P  R  P  D  S  S  A  G  21
```

FIGURE 1B

```
 64  GGCTCCAGCGCGGGGGCGGGGGCAGCGCGGGGGCGCGGGGCCCCCTCGAGGCCCG  123
 22  G  S  S  A  G  G  G  G  S  A  G  G  G  A  A  P  S  E  G  P     41

124  GCGGTGGGCGGCGTGCCCGGAGGCGGCGGGGGGGCGGGTGGGCGCAGGCAGC  183
 42  A  V  G  G  V  P  G  G  A  G  G  G  G  V  V  G  A  G  S     61

184  GGCGAGGACAACCGGAGCTCCGCGGGAGCCCCGGGTCCGCGGGGCGCGGCGACGTG  243
 62  G  E  D  N  R  S  S  A  G  E  P  G  S  A  G  G  D  V     81

244  AATGGCACGGCCGTCGGGGACTGGTGAGCCCGCCAGGCTGGGCGTGGGCGTC  303
 82  N  G  T  A  A  V  G  G  L  V  V  S  A  Q  G  V  G  V    101
```

FIGURE 1C

```
304  TTCCTGGCAGCCCTTCATCCTTATGGCCGTGGCAGGTAACCTGCTGTCATCCTCTCAGTG  363
102   F  L  A  A  F  I  L  M  A  V  A  G  N  L  L  V  I  L  S  V   121

364  GCCTGCAACCGCCACCTGCAGACCGTCACCAACTATTTCATCGTGAACCTGGCCGTGGCC  423
122   A  C  N  R  H  L  Q  T  V  T  N  Y  F  I  V  N  L  A  V  A   141

424  GACCTGCTGCTGAGCGCCACCGTACTGCCCTTCTCGGCCACCATGGAGGTTCTGGGCTTC  483
142   D  L  L  L  S  A  T  V  L  P  F  S  A  T  M  E  V  L  G  F   161

484  TGGGCCTTTGGCCGCGCCTTCTGCGACGTATGGGCCGCCGCTGTGGACGTGCTGTGCACG  543
162   W  A  F  G  R  A  F  C  D  V  W  A  A  A  V  D  V  L  C  C  T  181
```

FIGURE 1D

```
544  GCCTCCATCCTCAGCCTCTGCACCATCTCCGTGGACCGGTACGTGGGCGTGCGCCACTCA  603
182   A  S  I  L  S  L  C  T  I  S  V  D  R  Y  V  G  V  R  H  S   201

604  CTCAAGTACCCAGCCATCATGACCGAGCGCAAGGCCGCCATCCTGGCCCTGCTGCTCTGG  663
202   L  K  Y  P  A  I  M  T  E  R  K  A  A  I  L  A  L  L  W    221

664  GTCGTAGCCCTGGTGGTGTCCGTAGGGCCCCTGCTGGGCTGGAAGGAGCCCGTGCCCCCT  723
222   V  V  A  L  V  V  S  V  G  P  L  L  G  W  K  E  P  V  P  P   241

724  GACGAGGCGCTTCTGCGGTATCACCGAGGAGGCCGCTACGCTGTCTTCTCCTCCGTGTGC  783
242   D  E  R  F  C  G  I  T  E  E  A  A  G  Y  A  V  F  S  S  V  C   261
```

FIGURE 1E

```
                      810                   830
784  TCCTTCTACCTGCCCATGGGCGTCATCGTGGTCATGTACTGCCGCGTGTACGTGGTCGCG  843
262   S  F  Y  L  P  M  A  V  I  V  V  M  Y  C  R  V  Y  V  V  A   281
                      850                   870                   890
844  CGCAGCACCACGCGCAGCCTCGAGGCAGGCGTCAAGGCGAGGCAAGGCCTCCGAG       903
282   R  S  T  T  R  S  L  E  A  G  V  K  R  E  R  G  K  A  S  E   301
                      910                   930                   950
904  GTGGTGCTGCGCCATCCACTGTCGCGGGGCGCAATGACGGGCGCACGGCATG          963
302   V  V  L  R  I  H  C  R  G  A  A  T  G  A  D  G  A  H  G  M   321
                      970                   990                   1010
964  CGCAGCGCCAAGGGCCACACCTTCCGCAGCTCGTCCCTGTCCGTGCTCTCCAAGTTCTCC 1023
322   R  S  A  K  G  H  T  F  R  S  S  L  S  V  R  L  L  K  F  S   341
```

FIGURE 1F

```
       1030            1050                1070
1024  CGTGAGAAGAAGGCGGCCAAGACTCTGGCCATCGTCGTGGTGTCTTCGTGCTCTGCTGG  1083
 342   R   E   K   K   A   A   K   T   L   A   I   V   V   G   V   F   V   L   C   W    361

1090            1110                1130
1084  TTCCCCTTCTTCTTTGTCCTGCCGCTCGGCTCCCTTGTCCCGCAGCTGAAGCCATCGGAG  1143
 362   F   P   F   F   F   V   L   P   L   G   S   L   F   P   Q   L   K   P   S   E    381

1150            1170                1190
1144  GGCGTCTTCAAGGTCATCTTCTGGCTACTTCAACAGCTGCGTGAACCCGCTCATC       1203
 382   G   V   F   K   V   I   F   W   L   G   Y   F   N   S   C   V   N   P   L   I    401

1210            1230                1250
1204  TACCCCTGTTCCAGCCGCGAGTTCAAGGCGGCCTTCCTGCGTCTCCTGCGCTGCCAGTGC  1263
 402   Y   P   C   S   S   R   E   F   K   R   A   F   L   R   L   L   R   C   Q   C    421
```

FIGURE 1G

```
1264  CGTCGTCGCCGGCGGCCGCCCTCTCTGGCGTGTCTACGGCCACCACTGGCGGGCCTCC  1323
422   R  R  R  R  R  R  P  L  W  R  V  Y  G  H  H  W  R  A  S   441

1324  ACCAGCGGCCTGCGCCAGGACTGCGCCCCGAGTTCGGGCGACGCCCCCGAGGCGCCG   1383
442   T  S  G  L  R  Q  D  C  A  P  S  S  G  D  A  P  P  G  A  P  461

1384  CTGGCCCTCACCGCGCTCCCCGACCCCGAACCCCCAGGCACCCCCAGGCACCCCAGGATGCAG  1443
462   L  A  L  T  A  L  P  D  D  P  P  E  P  P  G  T  P  E  M  Q   481

1444  GCTCCGGTGGCCAGCCGTCGAAAGCCACCAGCCCTTCCGCCGAGTGGAGGCTGCTGGGG  1503
482   A  P  V  A  S  R  R  K  P  P  S  A  F  R  E  W  R  L  L  G   501
```

FIGURE 1H

```
1504  CCGTTCCGGAGACCCACGACCCAGCTGCGCCAAAGTCTCCAGCCTGTCGCACAAGATC  1563
502    P  F  R  R  P  T  T  Q  L  R  A  K  V  S  S  L  S  H  K  I   521

1564  CGGCGCCGGGGCCGCGCAGCCCAGGCCAGGAGGCGCGCCCAGCGTGCGCCCAGCGTCAGAGGTGGAGGCT  1623
522    R  A  G  G  A  Q  R  A  E  A  A  C  A  Q  R  S  E  V  E  A   541

1624  GTGTCCCTAGGCGTCCCACACGAGGTGGCCGAGGCCACCTGCCAGGCCTACGAATTG  1683
542    V  S  L  G  V  P  H  E  V  A  E  G  A  T  C  Q  A  Y  E  L   561

1684  GCCGACTACAGCAACCTACGGGAGACCGATATTTAAGGACCCCAGAGCTAGGCCCGGGAG  1743
562    A  D  Y  S  N  L  R  E  T  D  I  *                           572
```

FIGURE 11

```
          1750                  1770                  1790
1744  TGTGCTGGGCTTGGGGGTAAGGGGGACCAGAGAGGCGGGCTGGTGTTCTAAGAGCCCCCG  1803
          1810                  1830                  1850
1804  TGCAAATCGGAGACCCGGAAACTGATCAGGGCAGCTGCTCTGTGACATCCCTGAGGAACT  1863
          1870                  1890                  1910
1864  GGGCAGAGCTTGAGGCTGGAGCCCCTTGAAAGGTGAAAAGTAGTGGGGCCCCTGCTGGAC  1923
          1930                  1950
1924  TCAGGTGCCCAGAACTCTTTCTTAGAAGGGAGAGGCTGC  1963
```

FIGURE 2A

| FIGURE 2A, | 10/37 |
|---|---|
| FIGURE 2B, | 11/37 |
| FIGURE 2C, | 12/37 |
| FIGURE 2D, | 13/37 |
| FIGURE 2E, | 14/37 |
| FIGURE 2F, | 15/37 |
| FIGURE 2G, | 16/37 |
| FIGURE 2H, | 17/37 |

```
         -120                -100                 -80                 -63
-122 GCCAGGAGGGCGCCCTCTGGGAAGAAGACCACGGGGAAGCAAAGTTTCAGGGCAGCTGAG

-60                 -40                 -20                  -3
 -62 GAGCCCTTCGCCGCAGCCCTTCCGAGCCCAATCATCCCCCAGCCTATGGAGGGGACTCT 0                  20                  40                 57
  -2 AAGATGAATCCCGACCTGGACACCGGCCACAACACATCAGCACCTGCCACTGGGGAGAG      19
   0      M  N  P  D  L  D  T  G  H  N  T  S  A  P  A  H  W  G  E 60                  80                 100                117
  58 TTGAAAAATGCCAACTTCACTGGCCCCAACCAGACCTCGAGCAACTCCACACTGCCCCAG     39
  20  L  K  N  A  N  F  T  G  P  N  Q  T  S  S  N  S  T  L  P  Q
```

FIGURE 2B

```
118  CTGGACATCACCAGGGCCATCTCTGTGGGCCTGGTGCTGGGCGCCTTCATCCTCTTTGCC  177
 40   L  D  I  T  R  A  I  S  V  G  L  V  L  G  A  F  I  L  F  A   59

178  ATCGTGGGCAACATCCTAGTCATCTTGTCTGTGGCCTGCAACCGGCACCTGCGGACGCCC  237
 60   I  V  G  N  I  L  V  I  L  S  V  A  C  N  R  H  L  R  T  P   79

238  ACCAACTACTTCATTGTCAACCTGGCCATGGCCGACCTGCTGTTGAGCTTCACCGTCCTG  297
 80   T  N  Y  F  I  V  N  L  A  M  A  D  L  L  L  S  F  T  V  L   99

298  CCCTTCTCAGCGGCCCTAGAGGTGCTCGGCTACTGGGTGCTGGGGCGGATCTTCTGTGAC  357
100   P  F  S  A  A  L  E  V  L  G  Y  W  V  L  G  R  I  F  C  D  119
```

FIGURE 2C

```
358  ATCTGGGCAGCCGTGGATGTCCTGTGCTGCACAGGTCCATTCTGAGCCTGTGCCATC  417
120   I  W  A  A  V  D  V  L  C  C  T  A  S  I  L  S  L  C  A  I   139

418  TCCATCGATCGCTACATCGGGGTGCGCTACTCTCTGCAGTATCCCACGCTGGTCACCCGG  477
140   S  I  D  R  Y  I  G  V  R  Y  S  L  Q  Y  P  T  L  V  T  R   159

478  AGGAAGGCCATCTGGCCGTCAGTGTCTGCTCTTGTCCACCGTCTCATCTCCATCGGG  537
160   R  K  A  I  L  A  L  L  S  V  W  V  L  S  T  V  I  S  I  G   179

538  CCTCTCCTTGGGTGGAAGGAGCCGGCACCCAACGATGACAAGGAGTGCGGGGTCACCGAA  597
180   P  L  L  G  W  K  E  P  A  P  N  D  D  K  E  C  G  V  T  E   199
```

FIGURE 2D

```
       600              620              640
598  GAACCCTCTATGCCCTCTCTCCTTCTCTGGGCTCTTCTACATCCCTCTGGCTGTCATT   657
200   E  P  P  F  Y  A  L  F  S  S  L  G  S  F  Y  I  P  L  A  V  I   219

660              680              700
658  CTAGTCATGTACTGCCGTGTCTATATAGTGGCCAAGAGAACCACCAAGAACCTAGAGGCA  717
220   L  V  M  Y  C  R  V  Y  I  V  A  K  R  T  T  K  N  L  E  A   239

720              740              760
718  GGAGTCATGAAGGAGATGTCCAACTCCAAGGAGCTGACCCTGAGGATCCATTCCAAGAAC  777
240   G  V  M  K  E  M  S  N  S  K  E  L  T  L  R  I  H  S  K  N   259

780              800              820
778  TTTCACGAGGAGGACACCCTTAGCAGTACCAAGGCCAAGGGCCACAACCCCAGGAGTTCCATA  837
260   F  H  E  D  T  L  S  S  T  K  A  K  G  H  N  P  R  S  S  I   279
```

FIGURE 2E

```
     840                860                880
838  GCTGTCAAACTTTTTAAGTCTCTCCAGGAAAGAAAGCAGCTAAGACGTTGGGCATTGTG  897
280   A  V  K  L  F  K  F  S  R  E  K  K  A  A  K  T  L  G  I  V   299

900                920                940
898  GTCGGTATGTTCATCTTGTGCTGGCTACCCTTCTTCATCGCTTTGGCTTCCTTG  957
300   V  G  M  F  I  L  C  W  L  P  F  F  I  A  L  P  L  G  S  L   319

960                980                1000
958  TTCTCCACCCTGAAGCCCCCGACGCCGTGTTCAAGGTGGTCTTCTGGGCTACTTC  1017
320   F  S  T  L  K  P  P  D  A  V  F  K  V  V  F  W  L  G  Y  F   339

1020               1040               1060
1018 AACAGCTGCCTCAACCCCATCATCTACCCATGCTCCAGCAAGGAGTTCAAGCGCGCTTTC  1077
340   N  S  C  L  N  P  I  I  Y  P  C  S  S  K  E  F  K  R  A  F   359
```

FIGURE 2F

```
1078   GTGCGCATCCTCGGGTGCCAGTGCCCGGCGCGCCGACGCCGGCCCGT   1137
360    V  R  I  L  G  C  Q  C  P  G  R  G  R  R  R  R  R  R   379

1138   CGCCTGGGCGGCTGCGCCTACACCTACCGGCCGTGGACCCGGGGCTCGGGTGAGCGC   1197
380    R  L  G  G  C  A  Y  T  Y  R  P  W  T  R  G  G  S  L  E  R   399

1198   TCGCAGTCGCGCAAGGACTCGCTGGACGACAGCGGCAGCTGCCTGAGCGGCAGCCAGCGG   1257
400    S  Q  S  R  K  D  S  L  D  D  S  G  S  C  L  S  G  S  Q  R   419

1258   ACCCTGCCCTCGGCCTCGCCGAGCCCGGGCTACCTGGGCCGCGGCGCCCCGCCAGTC   1317
420    T  L  P  S  A  S  P  S  P  G  Y  L  G  R  G  A  P  P  P  V   439
```

FIGURE 2G

```
                              1340                1360
1318  GAGCTGTGCGCCTTCCCCGAGTGGAAGGCCCCGGCCCTCCTGAGCCTGCCCGCCCT  1377
440    E   L   C   A   F   P   P   E   W   K   A   P   G   A   L   L   S   L   P   A   P   459
                              1400                1420
1378  GAGCCCCCCGGCCGCCGCCGCCGCCACGACTCGGGCCCGCTCTTCACCTTCAAGCTCCTG  1437
460    E   P   P   G   R   R   G   R   H   D   S   G   P   L   F   T   F   K   L   L   479
                              1460                1480
1438  ACCGAGCCCGAGAGCCCCGGGACCGACGGCGGCGCCAGCAACGGAGGCTGCGAGGCCGCG  1497
480    T   E   P   E   S   P   G   T   D   G   G   A   S   N   G   G   C   E   A   A   499
                              1520                1540
1498  GCCGACGTGGCCAACGGGCAGCCGCCCGGCTTCAAAAGCAACATGCCCCTGGCCCGGGCAG  1557
500    A   D   V   A   N   G   Q   P   P   G   F   K   S   N   M   P   L   A   P   G   Q   519
```

FIGURE 2H

1558 TTTTAGGGCCCCCGTGCGCAGCTTTCTTTCCCTGGGAGGAAAACATCGTGGGGGGA 1615
520  F  *                                                      520
     1560      1580         1600

FIGURE 3A

| | |
|---|---|
| FIGURE 3A, | 18/37 |
| FIGURE 3B, | 19/37 |
| FIGURE 3C, | 20/37 |
| FIGURE 3D, | 21/37 |
| FIGURE 3E, | 22/37 |
| FIGURE 3F, | 23/37 |
| FIGURE 3G, | 24/37 |

```
-124                -120         -100          -80          -65
     CCAGCCAAACCACTGGCAGGCTCCCTCCAGCCGAGACCTTTATTCCCGGCTCCCGAGCT

-64                  -60          -40          -20           -5
     CCGCCCTCCGGCCAGCCGGGAGGTGGCCCTGACAGCCGGACCTGCCCGGCCCCCGGCTG

-4                    0            20           40          55
 0   GGACCATGGTGTTCTCTCGGGAAATGCTTCCGACAGCTCCAACTGCACCCAACCGCCGG    19
     M  V  F  L  S  G  N  A  S  D  S  S  N  C  T  Q  P  P  A 56                    60           80          100          115
20   CACCGGTGAACATTTCCAAGGCCATTCTGCTCGGGGTGATCTTGGGGGGCCTCATTCTTT   39
     P  V  N  I  S  K  A  I  L  L  G  V  I  L  G  G  L  I  L  F
```

FIGURE 3B

```
                                       160
116  TCGGGGTGCTGGGTAACATCCTAGTGATCCTCTCCGTAGCCTGTCACCGACACCTGCACT  175
40     G  V  L  G  N  I  L  V  I  L  S  V  A  C  H  R  H  L  H  S    59

220
176  CAGTCACGCACTACTACATCGTCAACCTGGCCGTGGCCGACCTCCTGCTCACCTCCACGG  235
60     V  T  H  Y  Y  I  V  N  L  A  V  A  D  L  L  L  T  S  T  V    79

280
236  TGCTGCCCTTCTCCGCCATCTTCGAGGTCCTAGGCTACTGGGCCTTCGGCAGGGTCTTCT  295
80     L  P  F  S  A  I  F  E  V  L  G  Y  W  A  F  G  R  V  F  C    99

340
296  GCAACATCTGGGCGGGCAGTGGATGTGCTGTGCTGCACCGCGTCCATCATGGGCCTCTGCA  355
100    N  I  W  A  A  V  D  V  L  C  C  T  A  S  I  M  G  L  C  I   119
```

FIGURE 3C

```
                   380                 400
     TCATCTCCATCGACCGCTACATCGGCGTGAGCTACCCGCTGCGCTACCCAACCATCGTCA    415
356   I  S  I  D  R  Y  I  G  V  S  Y  P  L  R  Y  P  P  T  I  V  T   139
120

440                 460
     CCCAGAGGAGGGTCTCATGGCTCTGCTCTGTGGCACTCTCCCTGGTCATATCCA          475
416   Q  R  R  G  L  M  A  L  L  C  V  W  A  L  S  L  V  I  S  I     159
140

500                 520
     TTGGACCCCCTGTTCGGCTGGAGGCAGCCGGCCCCCGAGGACGAGACCATCTGCCAGATCA   535
476   G  P  L  F  G  W  R  Q  P  A  P  E  D  E  T  I  C  Q  I  N     179
160

560                 580
     ACGAGGAGCCGGGCTACGTGCTCTTCTCAGCGCTGGGCTCCTTCTACCTGCCTCTGGCCA    595
536   E  E  P  G  Y  V  L  F  S  A  L  G  S  F  Y  L  P  L  A  I     199
180
```

FIGURE 3D

```
596  TCATCCTGGTCATGTACTGCCGCGTCTACGTGGTGGCCAAGAGGGAGAGCCGGGGCCTCA  655
200   I  L  V  M  Y  C  R  V  Y  V  V  A  K  R  E  S  R  G  L  K   219

656  AGTCTGGCCTCAAGACCGACAAGTCGGACTCGGAGCAAGTGACGCTCCGCATCCATCGGA  715
220   S  G  L  K  T  D  K  S  D  S  E  Q  V  T  L  R  I  H  R  K   239

716  AAAACGCCCCGGCAGGAGGCAGGGGGATGGCCAGCGCCAAGACCAAGACGCACTTCTCAG  775
240   N  A  P  A  G  G  S  G  M  A  S  A  K  T  K  T  H  F  S  V   259

776  TGAGGCTCCTCAAGTTCTCCCGGGAGAAGAAAGCGGCCAAAACGCTGGGCATCGTGGTCG  835
260   R  L  L  K  F  S  R  E  K  K  A  A  K  T  L  G  I  V  V  G   279
```

FIGURE 3E

```
       840                                 860                               880
        .                                   .                                 .
836  GCTGCTTCGTCCTCCTCTGCTGCTGGCCTTTTTCTTAGTCATGCCCATGGGTCTTCTTCC   895
280   C  F  V  L  P  S  C  W  L  P  F  F  L  V  M  P  I  G  S  F  F  P   299

900                                 920                               940
        .                                   .                                 .
896  CTGATTTCAAGCCCTCTGAAACAGTTTTTAAAATAGTATTTTGGCTCGGATATCTAAACA   955
300   D  F  K  P  S  E  T  V  F  K  I  V  F  W  L  G  Y  L  N  S   319

960                                 980                              1000
        .                                   .                                 .
956  GCTGCATCAACCCCCATCATATACCCATGCTCCAGCCAAGAGTTCAAAAGGCCTTTCAGA   1015
320   C  I  N  P  I  I  Y  P  C  S  S  Q  E  F  K  K  A  F  Q  N   339

1020                                1040                              1060
        .                                   .                                 .
1016 ATGTCTTGAGAATCCAGTGTCTCTGCAGAAAGCAGTCTTCCAAACATGCCCTGGGCTACA   1075
340   V  L  R  I  Q  C  L  C  R  K  Q  S  S  K  H  A  L  G  Y  T   359
```

FIGURE 3F

```
         1080            1100            1120
1076 CCCTGCACCCCGGCCCCAGCCTGGAAGGGCCGTGGAAGGGCAACACAAGGACACATGGTGCGCATCCCCG  1135
 360    L  H  P  P  S  Q  A  V  E  G  Q  H  K  D  M  V  R  I  P  V            379

1140            1160            1180
1136 TGGGATCAAGAGAGACCTTCTACAGGATCTCCAAGACGGATGGCGTTTGTGAATGGAAAT  1195
 380    G  S  R  E  T  F  Y  R  I  S  K  T  D  G  V  C  E  W  K  F           399

1200            1220            1240
1196 TTTTCTTCTTCCATGCCCCGTGGATCTGCCAGGATTACAGTGTCCAAAGACCAATCCTCCT  1255
 400    F  S  S  M  P  R  G  S  A  R  I  T  V  S  K  D  Q  S  S  C           419

1260            1280            1300
1256 GTACCACAGCCCGGGGTGAGAAGTAAAAGCTTTTTGCAGTCTGCTGCTGTGTAGGGCCCT  1315
 420    T  T  A  R  V  R  S  K  S  F  L  Q  V  C  C  C  V  G  P  S           439
```

FIGURE 3G

```
1316  CAACCCCCAGCCTTGACAAGAACCATCAAGTTCCAACCATTAAGGTCCACCATCTCCC  1375
 440    T  P  S  L  D  K  N  H  Q  V  P  T  I  K  V  H  T  I  S  L   459

1376  TCAGTGAGAACGGGGAGGAAGTCTAGGACAGGAAAGATGCAGAGGAAAGGGAATATCTT  1435
 460    S  E  N  G  E  E  V  *                                       466

1436  AGGTACCATACCCTGGAGTTCTAGAGGATTCCTGACAAGCTTATTCCGATCCAGACATG  1495

1496  ATAGATACATTGATGAGTT  1514
```

| FIGURE 4A, 25/37 |
| FIGURE 4B, 26/37 |
| FIGURE 4C, 27/37 |
| FIGURE 4D, 28/37 |

FIGURE 4A

```
                 1                                              40
human  alpha1a   mtfrdllsvs fegprpdssa ggssaggggg saggaapseg
H318/3 alpha1a   .......... .......... .......... ..........
Rat    alpha1a   mtfrdilsvt fegprsssst ggsgagggag tvg.....peg
       Consensus MTFRD-LS-- FEGPR--SS- GGS-AGGG-G --G-----EG 41                                             80
human  alpha1a   pavggvpgg- ggggg-vga- sgednrssa. .....gepgs
H318/3 alpha1a   ........m- aalrs-mma- ylsewrtpty rstemvqrlr
Rat    alpha1a   gavggvpg.- tggga-vgt- sgednqsst. .....gepg
       Consensus --------A- -----V---G ---------- ----------

81                                             120
human  alpha1a   ag-ggdvngt ---------- ---------- ----------
H318/3 alpha1a   me-vqhstst ---------- ---------- ----m-----
Rat    alpha1a   aa-sgevngs ---------- ---------- ----t-----
       Consensus --A------- AAVGGLVVSA QGVGVGVFLA AFIL-AVAGN 121                                            160
human  alpha1a   ---------- ---------- ---------- ----t-----
H318/3 alpha1a   ---------- ---------- ---------- ----t-----
Rat    alpha1a   ---------- ---------- ---------- ---a------
       Consensus LLVILSVACN RHLQTVTNYF IVNLAVADLL LSA-VLPFSA
```

FIGURE 4B

```
                      161                                                              200
human    alpha1a      ----------  ----------  ---a------  ----------  ----------
H318/3   alpha1a      ----------  ----------  ---a------  ----------  ----------
Rat      alpha1a      ----------  ----------  ---t------  ----------  ----------
         Consensus    TMEVLGFWAF  GR-FCDVWAA  VDVLCCTASI  LSLCTISVDR 201                                                              240
human    alpha1a      ----------  ----------  ----------  -----v----  ----------
H318/3   alpha1a      ----------  ----------  ----------  -----v----  ----------
Rat      alpha1a      ----------  ----------  ----------  ------a---  ----------
         Consensus    YVGVRHSLKY  PAIMTERKAA  AILALLW-VA  LVVSVGPLLG 241                                                              280
human    alpha1a      ----------  --------a-  --v-------  ----------  ----------
H318/3   alpha1a      ----------  --------a-  --v-------  ----------  ----------
Rat      alpha1a      ----------  --------v-  --i-------  ----------  ----------
         Consensus    WKEPVPPDER  FCGITEE-GY  A-FSSVCSFY  LPMAVIVVMY 281                                                              320
human    alpha1a      ----------  ------v---  --r-------  ----------  -------g--
H318/3   alpha1a      ----------  ------v---  --r-------  ----------  -------g--
Rat      alpha1a      ----------  ------i---  --p-------  ----------  -------s--
         Consensus    CRVYVVARST  TRSLEAG-KR  E-GKASEVVL  RIHCRGAAT-
```

FIGURE 4C

```
                        321                                                                      360
human   alpha1a         -d-ah-mr-a  ----f-----  ----------  ----------
H318/3  alpha1a         -d-ah-mr-a  ----f-----  ----------  ----------
Rat     alpha1a         -k-yp-tq-s  ----l-----  ----------  ----------
        Consensus       A-G---G---S-  KGHT-RSSLS  VRLLKFSREK  KAAKTLAIVV 361                                                                      400
human   alpha1a         ----------  ----------  ----------  ----------
H318/3  alpha1a         ----------  ----------  ----------  ----------
Rat     alpha1a         ----------  ----------  ----------  ----------
        Consensus       GVFVLCWFPF  FFVLPLGSLF  PQLKPSEGVF  KVIFWLGYFN 401                                                                      440
human   alpha1a         ----------  ----.rp-wrv
H318/3  alpha1a         ----------  ----.rp-wrv
Rat     alpha1a         ----------  ----lws-rpp
        Consensus       SCVNPLIYPC  SSREFKRAFL  RLLRCQCRRR  RRR----L---

441                                                                      480
human   alpha1a         yg..hhw---  ...stsgl-q  dca----gdap  --ap-alt-l
H318/3  alpha1a         yg..hhw---  ...stsgl-q  dca----gdap  --ap-alt-l
Rat     alpha1a         lasldrr--f  rlrpqpsh-s  prg---phct  --cg-grh-.
        Consensus       -----RA---  ------R---  ---PSS----  PG--L----A-
```

FIGURE 4D

```
                  481
human alpha1a     pdpdpeppgt pem-apv---r -k..ppsafr ewrllgpfr-
H318/3 alpha1a    pdpdpeppgt pem-apv---r -shpapsasg gcwgrsgdp-
Rat alpha1a       ......gdag fgl-qsk--l -.......lr ewrllgplq-
Consensus         ---------- ----Q---AS- R--------- --------R
                                                           520

521                                      560
human alpha1a     -ttqlrakvs slshkiragg -q-aeaac-q -seveavslg
H318/3 alpha1a    -scapkspac rtrsppgars -q-qraps-q -wrlcp*...
Rat alpha1a       -ttqlrakvs slshkirs.g -r-aetac-l -seveavsln
Consensus         P--------- ---------- A-R-----A- R-----SL- 561                                      588
human alpha1a     vphevaegat cqayeladys nlretdi*
H318/3 alpha1a    .......... .......... ........
Rat alpha1a       vpqdgaeavi cqayepgdys nlretdi*
Consensus         VP---AE--- CQAYE--DYS NLRETDI*
```

| FIGURE 5A, 29/37 |
| FIGURE 5B, 30/37 |
| FIGURE 5C, 31/37 |
| FIGURE 5D, 32/37 |

FIGURE 5A

```
                        1                                                40
Rat      alpha1b        ------------ ------------ ------h----- -dd---------
Hamster  alpha1b        ------------ ------------ ------q----- -da---------
Human    alpha1b        ------------ ------------ ------h----- -na---------
         Consensus      MNPDLDTGHN   TSAPA-WGEL   K--NFTGPNQ   TSSNSTLPQL 41                                               80
Rat      alpha1b        -v---------- ------------ ------i----- ------------
Hamster  alpha1b        -v---------- ------------ ------i----- ------------
Human    alpha1b        -i---------- ------------ ------m----- ------------
         Consensus      D-TRAISVGL   VLGAFILFAI   VGNILVLILSV  ACNRHLRTPT 81                                              120
Rat      alpha1b        ------------ ------------ ---t-------- ------------
Hamster  alpha1b        ------------ ------------ ---t-------- ------------
Human    alpha1b        ------------ ------------ ---a-------- ------------
         Consensus      NYFIVNLA-A   DLLLSFTVLP   FSA-LEVLGY   WVLGRIFCDI 121                                             160
Rat      alpha1b        ------------ ------------ ------------ ------------
Hamster  alpha1b        ------------ ------------ ------------ ------------
Human    alpha1b        ------------ ------------ ------------ ------------
         Consensus      WAAVDVLCCT   ASILSLCAIS   IDRYIGVRYS   LQYPTLVTRR
```

FIGURE 5B

```
                    161                                                              200
Rat     alpha1b     ---------- ---------- ---------- ---------- ----------
Hamster alpha1b     ---------- ---------- ---------- ---------- ----------
Human   alpha1b     ---------- ---------- ---------- ---------- ----------
Consensus           KAILALLSVW VLSTVISIGP LLGWKEPAPN DDKECGVTEE 201                                                              240
Rat     alpha1b     --c---c--- ---------- ---------- ----------
Hamster alpha1b     --y---s--- ---------- ---------- ----------
Human   alpha1b     --y---s--- ---------- ---------- ----------
Consensus           PF-ALF-SLG SFYIPLAVIL VMYCRVYIVA KRTTKNLEAG 241                                                              280
Rat     alpha1b     ---------- ---------- ---------- ----------
Hamster alpha1b     ---------- ---------- ---------- ----------
Human   alpha1b     ---------- ---------- ---------- ----------
Consensus           VMKEMSNSKE LTLRIHSKNF HEDTLSSTKA KGHNPRSSIA 281                                                              320
Rat     alpha1b     ---------- ---------- ---------- ----------
Hamster alpha1b     ---------- ---------- ---------- ----------
Human   alpha1b     ---------- ---------- ---------- ----------
Consensus           VKLFKFSREK KAAKTLGIVV GMFILCWLPF FIALPLGSLF
```

FIGURE 5C

```
                  321                                                          360
Rat     alpha1b   ----------  ----------  ----------  ----------  -------m
Hamster alpha1b   ----------  ----------  ----------  ----------  -------m
Human   alpha1b   ----------  ----------  ----------  ----------  -------v
Consensus         STLKPPDAVF  KVVFWLGYFN  SCLNPIIYPC  SSKEFKRAF- 361                                                          400
Rat     alpha1b   -------..-  gg--------  --a-------  ----------  ----------
Hamster alpha1b   -------..-  sg--------  --a-------  ----------  ----------
Human   alpha1b   ------rg-   gr--------  --g-------  ----------  ----------
Consensus         RILGCQC--R  --RRRRRRRR  LG-CAYTYRP  WTRGGSLERS 401                                                          440
Rat     alpha1b   ----------  ---m--qk--  ----------  ----------  ----tq--v-
Hamster alpha1b   ----------  ---m--sq--  ----------  ----------  ----aq--l-
Human   alpha1b   ----------  ---l--sq--  ----------  ----------  ----ap--v-
Consensus         QSRKDSLDDS  GSC-SG---RT LPSASPSPGY  LGRG--PP-E 441                                                          480
Rat     alpha1b   ---f-----.p ----------  ----------  -------l--  ---------g
Hamster alpha1b   ---y----.s  ----------  ----------  -------l--  ---------g
Human   alpha1b   ---f----ap  ------pa--  ----------  -------h--  ---------t
Consensus         LCA-PEWK--  GALLSL--PE  PPGRRGR-DS  GPLFTFKLL-
```

FIGURE 5D

```
                      481                                    520
Rat      alpha1b     d-----eat  -----dttt  -l-------  -----g---h-
Hamster  alpha1b     e-----egd  -----datt  -l-------  -----a---h-
Human    alpha1b     e-----dgg  -----eaaa  -v-------  -----a---q-
         Consensus   -PESPGT--  ASNGGC---  D-ANGQPGFK SNMPL-PG-F 521
Rat      alpha1b     *
Hamster  alpha1b     *
Human    alpha1b     *
         Consensus   *
```

FIGURE 6A

```
                         1                                                        40
Human     alphalc        ----------  ----------  ----------  ----------
Bovine    alphalc        ----------  -----v----  ----q--a--  ----------
Consensus                ----------  -----h--p-  ----h--p--  ----------
                         MVFLSGNASD  SSNCT-PP-P  VNISKAILLG  VILGGLILFG 41                                                       80
Human     alphalc        ----------  ----------  ----------  ----------
Bovine    alphalc        ----------  ----------  ----------  ----------
Consensus                ----------  ----------  ----------  ----------
                         VLGNILVILS  VACHRHLHSV  THYYIVNLAV  ADLLLTSTVL 81                                                      120
Human     alphalc        ----------  -----v----  i---------  ----------
Bovine    alphalc        ----------  -----i----  v---------  ----------
Consensus                ----------  ----------  ----------  ----------
                         PFSAIFE-LG  YWAFGRVFCN  -WAAVDVLCC  TASIMGLCII 121                                                     160
Human     alphalc        ----------  ----------  r---------  ----------
Bovine    alphalc        ----------  ----------  k---------  ----------
Consensus                ----------  ----------  ----------  ----------
                         SIDRYIGVSY  PLRYPTIVTQ  -RGLMALLCV  WALSLVISIG
```

| FIGURE 6A, | 33/37 |
|---|---|
| FIGURE 6B, | 34/37 |
| FIGURE 6C, | 35/37 |

FIGURE 6B

```
                161
Human   alpha1c  ---------- ---------- ---------- ---------- ----------
Bovine  alpha1c  ---------- ---------- ---------- ---------- ----------
        Consensus PLFGWRQPAP EDETICQINE EPGYVLFSAL GSFY-PL-II
                                                         ----l---a--  200
                                                         ----v--t---

201
Human   alpha1c  ---------- ---------- ---------- ---------- ----------
Bovine  alpha1c  ---------- ---------- ---------- ---------- ----------
        Consensus LVMYCRVYVV AKRESRGLKS GLKTDKSDSE QVTLRIHRKN           240

241
Human   alpha1c  -pa----ma- ---t------ ---------- ----------
Bovine  alpha1c  -qv----vt- ---n------ ---------- ----------
        Consensus A--GGSG--S AK-KTHFSVR LLKFSREKKA AKTLGIVVGC           280

281
Human   alpha1c  ---------- ---------- ---------- -k-------  v-------
Bovine  alpha1c  ---------- ---------- ---------- --r------  a-------
        Consensus FVLCWLPFFL VMPIGSFFPD F-PSETVFKI -FWLGYLNSC           320
```

FIGURE 6C

```
                 321
Human    alpha1c  ----------  ----------  ------c---  ----a-----
Bovine   alpha1c  ----------  ----------  ------r---  ----t-----
Consensus         INPIIYPCSS  QEFKKAFQNV  LRIQCL-RKQ  SSKH-LGYTL 361                                            400
Human    alpha1c  --p--qav--  ---m------  ---r----r-  ------f---
Bovine   alpha1c  --a--hvl--  ---l------  --a---k---  ------i---
Consensus         H-PS---EGQ  HKD-VRIPVG  S-ETFY-ISK  TDGVCEWK-F 401                                            440
Human    alpha1c  --m-------i  t-sk-q-s--  ----------  ------v---
Bovine   alpha1c  --l-------m  a-ar-p-a--  ----------  ------l---
Consensus         SS-PRGSAR-  -V--D-S-CT  TARVRSKSFL  QVCCC-GPST 441                                            467
Human    alpha1c  --ldk---v-  ---v------  ----------  ------*
Bovine   alpha1c  --hge---i-  ---i------  ----------  ------*
Consensus         PS---NHQ-P  TIK-HTISLS  ENGEEV*
```

DNA ENCODING HUMAN α 1 ADRENERGIC RECEPTORS AND USES THEREOF

This application is a divisional of U.S. Ser. No. 08/406,855, filed Aug. 21, 1995, now U.S. Pat. No. 5,861,309, which is a 371 national stage filing of PCT/US 93/09187, filed Sep. 24, 1993, which is a continuation-in-part of U.S. Ser. No. 07/952,798, filed Sep. 25, 1992, now abandoned.

BACKGROUND OF THE INVENTION

Throughout this application various publications are referred to by partial citations within parenthesis. Full citations for these publications may be found at the end of the specification immediately preceding the claims. The disclosures of these publications, in their entireties, are hereby incorporated by reference into this application in order to more fully describe the state of the art to which this invention pertains.

Although adrenergic receptors (ARs) bind the same endogenous catecholamines (epinephrine and norepinephrine, NE) their physiological as well as pharmacological specificity is markedly diverse. This diversity is due primarily to the existence of at least nine different proteins encoding three distinct adrenergic receptors types ($\alpha_1$, $\alpha 2$, and $\beta$). These proteins belong to the super-family of G-protein coupled receptors, and are characterized by a single polypeptide chain which span the plasma membrane seven times, with an extracellular amino terminus, and a cytoplasmic carboxyl terminus. The molecular cloning of three genes encoding $\alpha_1$-ARs supports the existence of pharmacologically and anatomically distinct $\alpha_1$-receptor subtypes. The $\alpha_{1b}$-receptor was originally cloned from a hamster smooth muscle cell line cDNA library, and encodes a 515 a.a. peptide that shows 42–47% homology with other ARs. The message for the $\alpha_{1b}$-receptor is abundant in rat liver, heart, cerebral cortex and kidney, and its gene was localized to human chromosome 5 (4). A second cDNA clone from a bovine brain library was found which encoded a 466-residue polypeptide with 72% homology to the $\alpha_{1b}$-AR gene. It was further distinguished from $\alpha_{1b}$ by the finding that its expression was restricted to human hippocampus, and by its localization to human chromosome 8 and it has been designated as the $\alpha_{1c}$-AR (20). The cloning of an $\alpha_{1a}$-AR has been reported recently. This gene, isolated from a rat brain cDNA library, encodes a 560-residue polypeptide that shows 73% homology with the hamster $\alpha_{1b}$-receptor. The message for this subtype is abundant in rat vas deferens, aorta, cerebral cortex and hippocampus, and its gene has been localized to human chromosome 5 (12).

Pharmacological studies have demonstrated the existence of two $\alpha_1$-adrenergic receptor subtypes. The studies of $\alpha_1$-AR-mediated responses in vascular tissue suggested the possible existence of receptor subtypes, based on the potency and efficacy of adrenergic agonists, as well as differential sensitivity of $\alpha_1$ receptor-mediated responses to extracellular calcium and calcium channel blockers (6, 24). Although radioligand binding studies of brain $\alpha_1$-ARs with either [³H]WB4101 and [³H]prazosin showed good agreement with the potency of α-adrenergic antagonists on vascular responses (23, 10), subsequent binding studies of rat brain $\alpha_1$-ARs provided strong evidence for the existence of receptor heterogeneity, based on the relative affinities for prazosin and WB4101 (15). These observations were supported by the finding that chloroethylclonidine (CEC) inactivated 50% of the $\alpha_1$ sites from rat cerebral cortex and 80% of the binding sites from liver or spleen ($\alpha_{1b}$), but did not inactivate $\alpha_1$-receptors from the hippocampus or vas deferens ($\alpha_{1a}$) (14). Taken together, these results suggested a classification of the $\alpha_{1a}$-subtype as high affinity for WB4101 and insensitive to alkylation by CEC, and $\alpha_{1b}$-subtype as 10 to 20 fold lower affinity for WB4101, but sensitive to inactivation by CEC. Consistent with this evidence the transfection of the hamster $\alpha_{1b}$ gene into COS-7 cells induced the expression of an α1-receptor with high affinity for WB4101, 95% of which could be inactivated by CEC. Conversely, upon expression of the rat $\alpha_{1a}$ receptor gene in COS-7 cells, it showed a 10-fold higher affinity for WB4101 than the $\alpha_{1b}$-receptor, and the binding site was resistant to inactivation by CEC. The existence of the $\alpha_{1c}$ receptor was not predicted from pharmacological data and upon expression it showed 16 and 30 fold higher affinity for WB4101 and phentolamine respectively, than the $\alpha_{1b}$-receptor and was partially inactivated (65%) by CEC.

Molecular cloning and pharmacological studies have demonstrated the existence of at least three $\alpha_1$-adrenergic receptor subtypes. However, it is not clear whether the pharmacological properties of these three cognates might be due also to species differences. This caveat is particularly relevant in the case of the bovine $\alpha_{1c}$ receptor, due to its restricted species and tissue expression. The cloning and expression of the human $\alpha_1$ adrenergic receptors will allow the further characterization of the pharmacology of the individual human $\alpha_1$ receptor subtypes.

SUMMARY OF THE INVENTION

This invention provides and isolated nucleic acid molecule encoding a human $\alpha_1$ adrenergic receptor. This invention further provides an isolated nucleic acid molecule encoding a human $\alpha_{1a}$ receptor. In one embodiment of this invention, the nucleic acid molecule comprises a plasmid pcEXV-$\alpha_{1a}$. This invention also provides an isolated nucleic acid molecule encoding a human $\alpha_{1b}$ receptor. In one embodiment of this invention, the nucleic acid molecule comprises a plasmid pcEXV-$\alpha_{1b}$. This invention further provides an isolated nucleic acid molecule encoding a human $\alpha_{1c}$ receptor. In one embodiment of this invention, the nucleic acid molecule comprises a plasmid pcEXV-$\alpha_{1c}$.

This invention also provides vectors such as plasmids comprising a DNA molecule encoding a human $\alpha_{1a}$ receptor, adapted for expression in a bacterial, a yeast cell, or a mammalian cell which additionally comprise regulatory elements necessary for expression of the DNA in the bacteria, yeast or mammalian cells so located relative to the DNA encoding the human $\alpha_{1a}$ receptor as to permit expression thereof. This invention also provides vectors such as plasmids comprising a DNA molecule encoding a human $\alpha_{1b}$ receptor, adapted for expression in a bacterial, a yeast cell, or a mammalian cell which additionally comprise regulatory elements necessary for expression of the DNA in the bacteria, yeast or mammalian cells so located relative to the DNA encoding the human $\alpha_{1b}$ receptor as to permit expression thereof. This invention also provides vectors such as plasmids comprising a DNA molecule encoding a human $\alpha_{1c}$ receptor, adapted for expression in a bacterial, a yeast cell, or a mammalian cell which additionally comprise regulatory elements necessary for expression of the DNA in the bacteria, yeast or mammalian cells so located relative to the DNA encoding the human $\alpha_{1c}$ receptor as to permit expression thereof.

This invention provides a mammalian cell comprising a DNA molecule encoding a human $\alpha_{1a}$ receptor. This invention also provides a mammalian cell comprising a DNA molecule encoding a human $\alpha_{1b}$ receptor. This invention also provides a mammalian cell comprising a DNA molecule encoding a human $\alpha_{1c}$ receptor.

This invention provides a nucleic acid probe comprising a nucleic acid molecule of at least 15 nucleotides capable of specifically hybridizing with a sequence included within the sequence of a nucleic acid molecule encoding a human $\alpha_{1a}$ receptor. This invention provides a nucleic acid probe comprising a nucleic acid molecule of at least 15 nucleotides capable of specifically hybridizing with a sequence included within the sequence of a nucleic acid molecule encoding a human $\alpha_{1b}$ receptor. This invention provides a nucleic acid probe comprising a nucleic acid molecule of at least 15 nucleotides capable of specifically hybridizing with a sequence included within the sequence of a nucleic acid molecule encoding a human $\alpha_{1c}$ receptor.

This invention provides an antisense oligonucleotide having a sequence capable of specifically binding to any sequences of an mRNA molecule encoding a human $\alpha_{1b}$ receptor so as to prevent translation of the mRNA molecule. This invention provides an antisense oligonucleotide having a sequence capable of specifically binding to any sequences of an mRNA molecule encoding a human $\alpha_{1b}$ receptor so as to prevent translation of the mRNA molecule. This invention provides an antisense oligonucleotide having a sequence capable of specifically binding to any sequences of an mRNA molecule encoding a human $\alpha_{1c}$ receptor so as to prevent translation of the mRNA molecule.

This invention provides method for detecting expression of a specific human $\alpha_1$ adrenergic receptor, which comprises obtaining RNA from cells or tissue, contacting the RNA so obtained with a nucleic acid probe comprising a nucleic acid molecule of at least 15 nucleotides capable of specifically hybridizing with a sequence included within the sequence of a nucleic acid molecule encoding a human $\alpha_1$ receptor under hybridizing conditions, detecting the presence of any mRNA hybridized to the probe, the presence of mRNA hybridized to the probe indicating expression of the specific human $\alpha_1$ adrenergic receptor, and thereby detecting the expression of the specific human $\alpha_1$ adrenergic receptor.

This invention provides a method for detecting the expression of a specific human α1 adrenergic receptor in a cell or tissue by in situ hybridization which comprises, contacting the cell or tissue with a nucleic acid probe comprising a nucleic acid molecule of at least 15 nucleotides capable of specifically hybridizing with a sequence included within the sequence of a nucleic acid molecule encoding a human $\alpha_1$ receptor under hybridizing conditions, detecting the presence of any mRNA hybridized to the probe, the presence of mRNA hybridized to the probe indicating expression of the specific human $\alpha_1$ adrenergic receptor, and thereby detecting the expression of the specific human $\alpha_1$ adrenergic receptor.

This invention provides a method for isolating a nucleic acid molecule encoding a receptor by nucleic acid sequence homology using a nucleic acid probe, the sequence of which is derived from the nucleic acid sequence encoding a human α1 adrenergic receptor.

This invention provides a method for isolating a nucleic acid molecule encoding a human $\alpha_1$ adrenergic receptor which comprises the use of the polymerase chain reaction and oligonucleotide primers, the sequence of which are derived from the nucleic acid sequence encoding a human α1 adrenergic receptor.

This invention provides a method for isolating a human $\alpha_1$ adrenergic receptor protein which comprises inducing cells to express the human $\alpha_1$ adrenergic receptor protein, recovering the human $\alpha_1$ adrenergic receptor from the resulting cells, and purifying the human $\alpha_1$ adrenergic receptor so recovered.

This invention provides an antibody to the human $\alpha_{1a}$ adrenergic receptor. This invention also provides an antibody to the human $\alpha_{1b}$ adrenergic receptor. This invention also provides an antibody to the human $\alpha_{1c}$ adrenergic receptor.

A pharmaceutical composition comprising an amount of a substance effective to alleviate the abnormalities resulting from overexpression of a human $\alpha_{1a}$ adrenergic receptor and a pharmaceutically acceptable carrier is provided by this invention. A pharmaceutical composition comprising an amount of a substance effective to alleviate the abnormalities resulting from overexpression of a human $\alpha_{1b}$ adrenergic receptor and a pharmaceutically acceptable carrier is provided by this invention. A pharmaceutical composition comprising an amount of a substance effective to alleviate the abnormalities resulting from overexpression of a human $\alpha_{1c}$ adrenergic receptor and a pharmaceutically acceptable carrier is provided by this invention.

A pharmaceutical composition comprising an amount of a substance effective to alleviate abnormalities resulting from underexpression of a human $\alpha_{1a}$ adrenergic receptor and a pharmaceutically acceptable carrier is provided by this invention. A pharmaceutical composition comprising an amount of a substance effective to alleviate abnormalities resulting from underexpression of a human $\alpha_{1b}$ adrenergic receptor and a pharmaceutically acceptable carrier is provided by this invention. A pharmaceutical composition comprising an amount of a substance effective to alleviate abnormalities resulting from underexpression of a human $\alpha_{1c}$ adrenergic receptor and a pharmaceutically acceptable carrier is provided by this invention.

This invention provides a transgenic non-human mammal whose genome comprises a nucleic acid molecule encoding a human α1 adrenergic receptor, the DNA molecule so placed as to be transcribed into antisense mRNA complementary to mRNA encoding a human at adrenergic receptor and which hybridizes to mRNA encoding a human $\alpha_1$ adrenergic receptor thereby reducing its translation.

This invention provides a method for determining the physiological effects of varying the levels of expression of a specific human α1 adrenergic receptor which comprises producing a transgenic non-human mammal whose levels of expression of a human $\alpha_1$ adrenergic receptor can be varied by use of an inducible promoter.

This invention provides method for determining the physiological effects of expressing varying levels of a specific human $\alpha_1$ adrenergic receptor which comprises producing a panel of transgenic non-human mammals each expressing a different amount of the human $\alpha_1$ adrenergic receptor.

This invention provides a method for determining whether a ligand not known to be capable of specifically binding to a human $\alpha_1$ adrenergic receptor can bind to a human $\alpha_1$ adrenergic receptor, which comprises contacting a mammalian cell comprising a plasmid adapted for expression in a mammalian cell which further comprises a DNA molecule which expresses a human $\alpha_1$ adrenergic receptor on the cell surface with the ligand under conditions permitting binding of ligands known to bind to a human $\alpha_1$ adrenergic receptor, detecting the presence of any ligand bound to the human $\alpha_1$ adrenergic receptor, the presence of bound ligand thereby determining that the ligand binds to the human $\alpha_1$ adrenergic receptor.

This invention provides a method for screening drugs to identify drugs which interact with, and specifically bind to, a human $\alpha_1$ adrenergic receptor on the surface of a cell, which comprises contacting a mammalian cell which comprises a plasmid adapted for expression in a mammalian cell which further comprises a DNA molecule which expresses a human $\alpha_1$ adrenergic receptor on the cell surface with a plurality of drugs, determining those drugs which bind to the human $\alpha_1$ adrenergic receptor expressed on the cell surface of the mammalian cell, and thereby identifying drugs which interact with, and bind to, the human $\alpha_1$ adrenergic receptor.

This invention provides a method for identifying a ligand which binds to and activates or blocks the activation of, a human $\alpha_1$ adrenergic receptor expressed on the surface of a cell, which comprises contacting a mammalian cell which comprises a plasmid adapted for expression in a mammalian cell which further comprises a DNA molecule which expresses a human $\alpha_1$ adrenergic receptor on the cell surface with the ligand, determining whether the ligand binds to and activates or blocks the activation of the receptor using a bioassay such as a second messenger assays.

This invention also provides a method for identifying a ligand which is capable of binding to and activating or inhibiting a human $\alpha_1$ adrenergic receptor, which comprises contacting a mammalian cell, wherein the membrane lipids have been labelled by prior incubation with a labelled lipid precursor molecule, the mammalian cell comprising a plasmid adapted for expression in a mammalian cell which further comprises a DNA molecule which expresses a human $\alpha_1$ adrenergic receptor with the ligand and identifying an inositol phosphate metabolite released from the membrane lipid as a result of ligand binding to and activating an $\alpha_1$ adrenergic receptor.

This invention also provides a method for identifying a ligand that is capable of binding to and activating or inhibiting a human $\alpha_1$ adrenergic receptor, wherein the binding of ligand to the adrenergic receptor results in a physiological response, which comprises contacting a mammalian cell which comprises a plasmid adapted for expression in a mammalian cell which further comprises a DNA molecule which expresses a human $\alpha_1$ adrenergic receptor with a calcium sensitive fluorescent indicator, removing the indicator that has not been taken up by the cell, contacting the cells with the ligand and identifying an increase or decrease in intracellular $Ca^{+2}$ as a result of ligand binding to and activating or inhibiting $\alpha_1$ adrenergic receptor activity.

This invention provides a method for detecting the presence of a human $\alpha_{1a}$ adrenergic receptor on the surface of a cell, which comprises contacting the cell with an antibody to human $\alpha_{1a}$ adrenergic receptor under conditions which permit binding of the antibody to the receptor, detecting the presence of any of the antibody bound to the human $\alpha 1a$ adrenergic receptor and thereby the presence of a human $\alpha_{1a}$ adrenergic receptor on the surface of the cell.

This invention provides a method for detecting the presence of a human $\alpha_{1b}$ adrenergic receptor on the surface of a cell, which comprises contacting the cell with an antibody to human $\alpha_{1b}$ adrenergic receptor under conditions which permit binding of the antibody to the receptor, detecting the presence of any of the antibody bound to the human $\alpha_{1b}$ adrenergic receptor and thereby the presence of a human $\alpha_{1b}$ adrenergic receptor on the surface of the cell.

This invention provides a method for detecting the presence of a human $\alpha_{1c}$ adrenergic receptor on the surface of a cell, which comprises contacting the cell with an antibody to human $\alpha_{1c}$ adrenergic receptor under conditions which permit binding of the antibody to the receptor, detecting the presence of any of the antibody bound to the human $\alpha_{1c}$ adrenergic receptor and thereby the presence of a human $\alpha_{1c}$ adrenergic receptor on the surface of the cell.

This invention provides a method of treating an abnormal condition related to an excess of activity of a human $\alpha_1$ adrenergic receptor subtype, which comprises administering an amount of a pharmaceutical composition effective to reduce $\alpha_1$ adrenergic activity as a result of naturally occurring substrate binding to and activating a specific $\alpha_1$ adrenergic receptor.

This invention provides a method for treating abnormalities which are alleviated by an increase in the activity of a specific human $\alpha_1$ adrenergic receptor, which comprises administering a patient an amount of a pharmaceutical composition effective to increase the activity of the specific human $\alpha_1$ adrenergic receptor thereby alleviating abnormalities resulting from abnormally low receptor activity.

This invention provides a method for diagnosing a disorder or a predisposition to a disorder associated with the expression of a specific human $\alpha_1$ adrenergic receptor allele which comprises: a.) obtaining DNA from subjects suffering from a disorder; b.) performing a restriction digest of the DNA with a panel of restriction enzymes; c.) electrophoretically separating the resulting DNA fragments on a sizing gel; d.) contacting the gel with a nucleic acid probe labelled with a detectable marker and which hybridizes to the nucleic acid encoding a specific human $\alpha_1$ adrenergic receptor; e.) detecting the labelled bands which have hybridized to the DNA encoding the specific $\alpha_1$ adrenergic receptor labelled with the detectable marker to create a unique band pattern specific to the DNA of subjects suffering with the disorder; f.) preparing DNA for diagnosis by steps a–e; g.)comparing the unique band pattern specific to the DNA of patients suffering from the disorder from step e and DNA obtained for diagnosis from step f to determine whether the patterns are the same or different and to diagnose thereby predisposition to the disorder if the patterns are the same.

This invention provides a method for identifying a substance capable of alleviating the abnormalities resulting from overexpression of a specific human $\alpha_1$ adrenergic receptor which comprises administering a substance to the transgenic non-human mammal comprising the DNA encoding a specific $\alpha_1$ adrenergic receptor and determining whether the substance alleviates the physical and behavioral abnormalities displayed by the transgenic nonhuman mammal as a result of overexpression of the human $\alpha_1$ adrenergic receptor subtype.

This invention provides a method for identifying a substance capable of alleviating the abnormalities resulting from underexpression of a human $\alpha_1$ adrenergic receptor subtype, which comprises administering a substance to a non-human transgenic mammal which is expressing a human $\alpha_1$ adrenergic receptor incapable of receptor activity or is underexpressing the human $\alpha_1$ adrenergic receptor subtype, and determining whether the substance alleviates the physical and behavioral abnormalities displayed by the transgenic nonhuman mammal as a result of underexpression of a human $\alpha_1$ adrenergic receptor subtype.

This invention provides a method of treating abnormalities in a subject, wherein the abnormality is alleviated by the reduced expression of a human $\alpha_1$ adrenergic receptor subtype which comprises administering to a subject an effective amount of the pharmaceutical composition effective to reduce expression of a specific $\alpha_1$ adrenergic receptor subtype.

This invention provides a method of treating abnormalities resulting from underexpression of a human $\alpha_1$ adrenergic receptor which comprises administering to a subject an amount of a pharmaceutical composition effective to alleviate abnormalities resulting from underexpression of the specific human $\alpha_1$ adrenergic receptor.

BRIEF DESCRIPTION OF THE FIGURES

FIGS. 1A–I. Nucleotide Sequence (SEQ ID NO. 1) and Deduced Amino Acid Sequence (SEQ ID NO. 2) of Novel Human Alpha-1a Adrenergic Receptor.

Figure 7A:
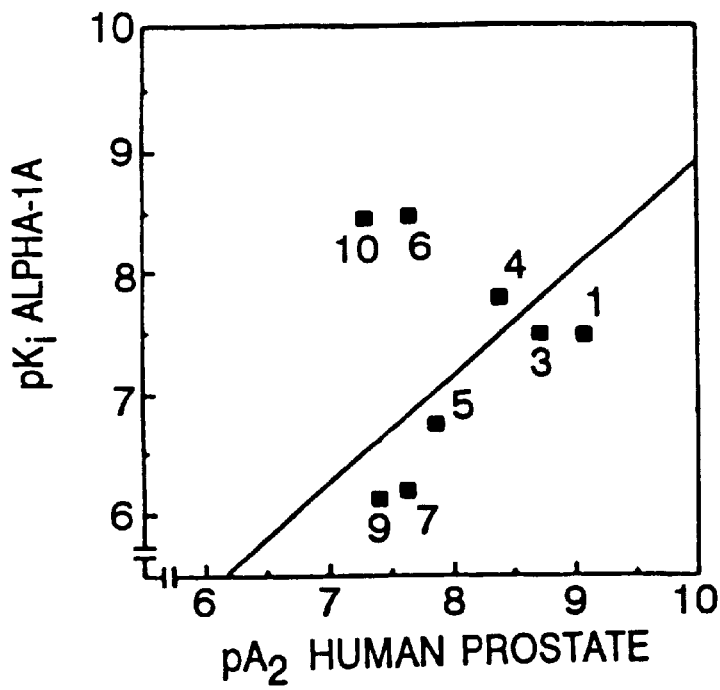

Nucleotides are presented in the 5' to 3' orientation and the coding region is numbered starting from the initiating methionine and ending in the termination codon. Deduced amino acid sequence by translation of a long open reading frame is shown, along with the 5' and 3' untranslated regions. Numbers in the left and right margins represent nucleotide (top line) and amino acid (bottom line) numberings, starting with the first position as the adenosine (A) and the initiating methionine (M), respectively.

FIGS. 2A–H. Nucleotide Sequence (SEQ ID NO. 3) and Deduced Amino Acid Sequence (SEQ ID NO. 4) of Novel Human Alpha-1b Adrenergic Receptor. Nucleotides are presented in the 5' to 3' orientation and the coding region is numbered starting from the initiating methionine and ending in the termination codon. Deduced amino acid sequence by translation of a long open reading frame is shown, along with the 5' and 3' untranslated regions. Numbers in the left and right margins represent nucleotide (top line) and amino acid (bottom line) numberings, starting with the first position as the adenosine (A) and the initiating methionine (M), respectively.

FIGS. 3A–G. Nucleotide Sequence (SEQ ID NO. 5) and Deduced Amino Acid Sequence (NEQ ID NO. 6) of Novel Human Alpha-1c Adrenergic Receptor.

Nucleotides are presented in the 5' to 3' orientation and the coding region is numbered starting from the initiating methionine and ending in the termination codon. Deduced amino acid sequence by translation of a long open reading frame is shown, along with the 5' and 3' untranslated regions. Numbers in the left and right margins represent nucleotide (top line) and amino acid (bottom line) numberings, starting with the first position as the adenosine (A) and the initiating methionine (M), respectively.

FIGS. 4A–D. Alignment of the Human Alpha-1a, H318/3 Alpha-1a, and Rat Alpha-1a Adrenergic Receptors. The deduced amino acid sequence of the human $\alpha_{1a}$ receptor (first line) (SEQ ID NO. 2), from the starting methionine (M) to the stop codon (*), is aligned with the previously published human "$\alpha_{1a}$" adrenergic receptor clone, H318/3 (2) (second line) (SEQ ID NO. 19) and with the rat $\alpha_{1a}$ (12) (third line) (SEQ ID NO. 20). Also shown is a consensus amino acid sequence (fourth line), containing a hyphen at a particular position, when all receptors have the same amino acid or an amino acid at this position, when there is disparity in the three receptors. Dots indicate spaces corresponding to no amino acid at this position. Note that the human and rat $\alpha_{1a}$ receptors have greater homology in the amino (positions 1–90) and carboxyl (positions 440–598) termini than do the previously published "$\alpha_{1a}$" (H318/3) and rat $\alpha_{1a}$ receptors (see text). Dots indicate spaces corresponding to no amino acid at this position. Numbers above amino acid sequences correspond to amino acid positions, starting with the initiating methionine (M) and ending with the termination codon (*).

FIGS. 5A–D. Alignment of the Human Alpha-1b, Hamster Alpha-1b, and Rat Alpha-1b Adrenergic Receptors. The deduced amino acid sequence of the human $\alpha_{1b}$ receptor (third line) (SEQ ID NO. 4), from the starting methionine (M) to the stop codon (*), is aligned with the previously published rat $\alpha_{1b}$ adrenergic receptor clone (25) (first line) (SEQ ID NO. 21) and with the hamster alpha-1b (4) (second line) (SEQ ID NO. 22). Also shown is a consensus amino acid sequence (fourth line), containing a hyphen at a particular position, when all receptors have the same amino acid or an amino acid at this position, when there is disparity in the three receptors. Dots indicate spaces corresponding to no amino acid at this position. Numbers above amino acid sequences correspond to amino acid position, starting with the initiating methionine (M) and ending with the termination codon (*).

FIGS. 6A–C. Alignment of the Human Alpha-1c and Bovine Alpha-1c Adrenergic Receptors. The deduced amino acid sequence of the human $\alpha_{1c}$ receptor (first line) (SEQ ID NO. 6), from the starting methionine (M) to the stop codon (*), is aligned with the previously published bovine $\alpha_{1b}$ adrenergic receptor clone (13) (second line). Also shown is a consensus amino acid sequence (third line) (SEQ ID NO. 23), containing a hyphen at a particular position, when all receptors have the same amino acid or an amino acid at this position, when there is disparity in the three receptors. Dots indicate spaces corresponding to no amino acid at this position. Numbers above amino acid sequences correspond to amino acid position, starting with the initiating methionine (M) and ending with the termination codon (*).

Figure 7B:
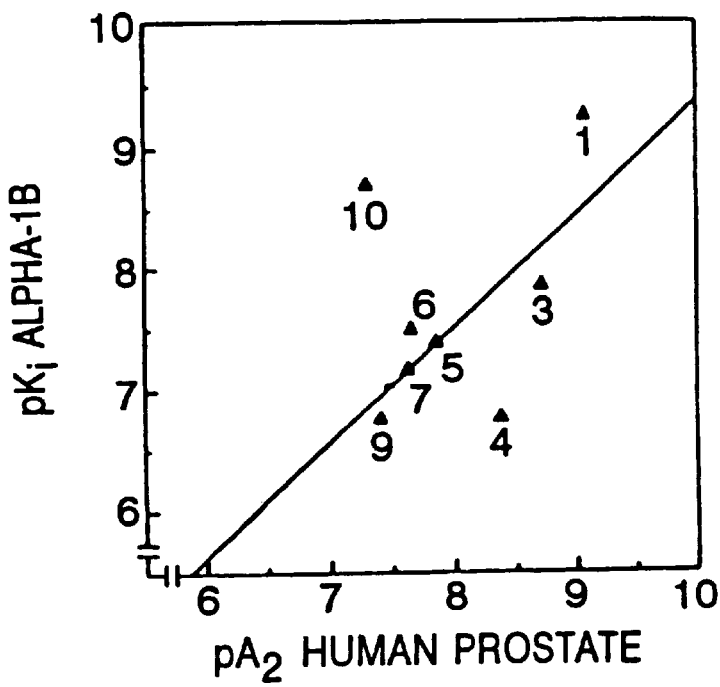
Figure 7C:
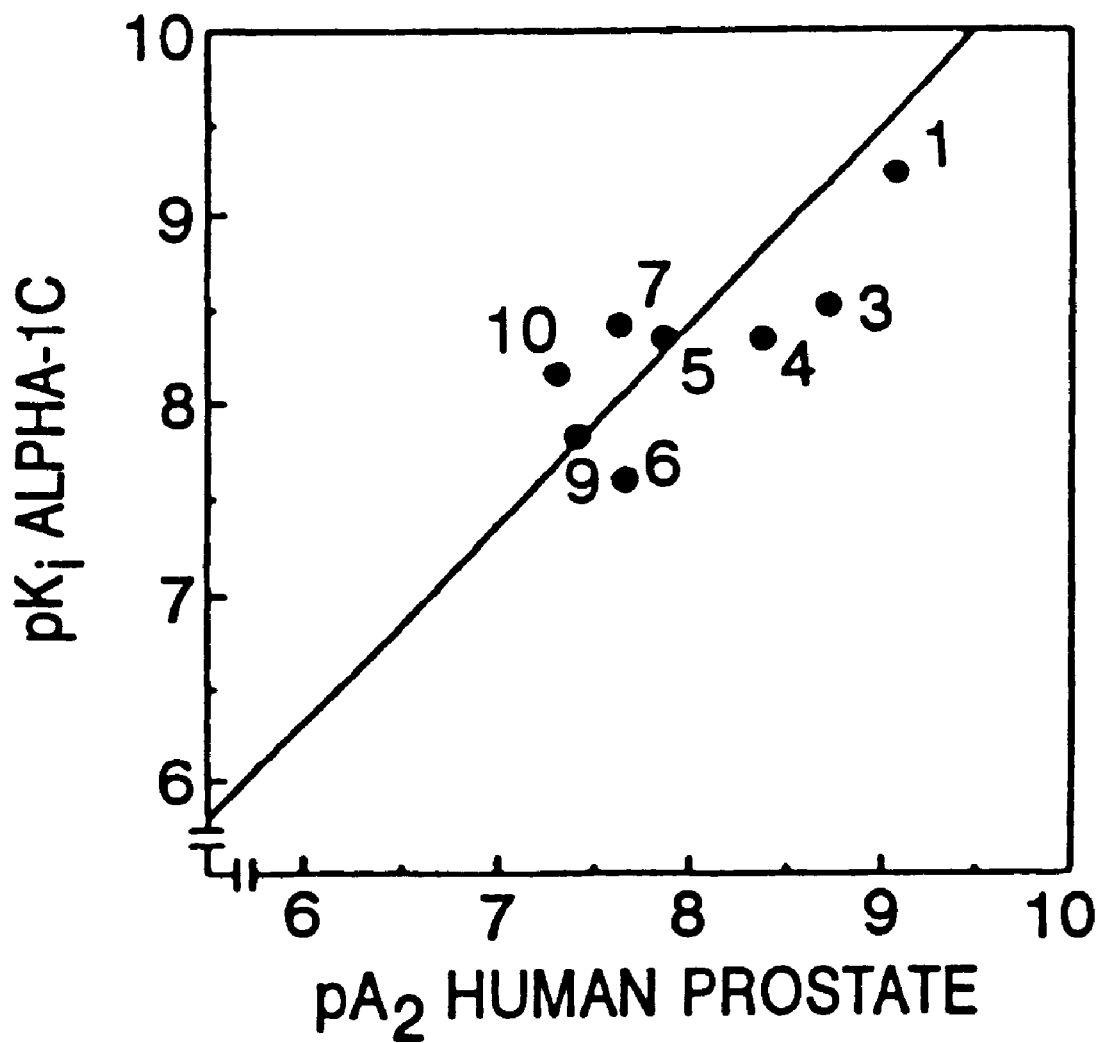

FIG. 7. Illustrates the correlation of inhibition constants (pK$_i$) for a series of $\alpha_1$ antagonists at the cloned human $\alpha_{1A}$, $\alpha_{1B}$, and $\alpha_{1C}$ receptors with efficiency of blocking contraction of human prostate tissue (pA$_2$).

DETAILED DESCRIPTION OF THE INVENTION

This invention provides an isolated nucleic acid molecule encoding a human $\alpha_1$ adrenergic receptor. This invention also provides an isolated nucleic acid molecule encoding a human $\alpha_{1a}$ adrenergic receptor. This invention also provides an isolated nucleic acid molecule encoding a human $\alpha_{1b}$ adrenergic receptor. This invention also provides an isolated nucleic acid molecule encoding a human $\alpha_{1c}$ adrenergic receptor. As used herein, the term "isolated nucleic acid molecule" means a non-naturally occurring nucleic acid molecule that is, a molecule in a form which does not occur in nature. Examples of such an isolated nucleic acid molecule are an RNA, cDNA, or an isolated genomic DNA molecule encoding a human $\alpha_{1a}$, human $\alpha_{1b}$ or human $\alpha_{1c}$ adrenergic receptor. As used herein, the term "$\alpha_{1a}$ receptor", "$\alpha_{1b}$ receptor", or "$\alpha_{1c}$ receptor" means a molecule which is a distinct member of a class of $\alpha_1$ adrenergic receptor molecules which under physiologic conditions, is substantially specific for the catecholamines epinephrine and norepinephrine, is saturable, and having high affinity for the catecholamines epinephrine and norepinephrine. The term "$\alpha_1$ adrenergic receptor subtype" refers to a distinct member of the class of human $\alpha_1$ adrenergic receptors, which may be any one of the human $\alpha_{1a}$, $\alpha_{1b}$ or $\alpha_{1c}$ adrenergic receptors. The term "specific $\alpha_1$ adrenergic receptor" refers to a distinct member of the group or class of human $\alpha_1$ adrenergic receptors, which may be any one of the human $\alpha_{1a}$, $\alpha_{1b}$ or $\alpha_{1c}$ adrenergic receptors. One embodiment of this invention is an isolated human nucleic acid molecule encoding a human $\alpha_{1a}$ adrenergic receptor. Such a molecule may have coding sequences substantially the same as the coding sequence in FIGS. 1A–1I. The DNA molecule of FIGS. 1A–1I encodes the sequence of the human $\alpha_{1a}$ adrenergic receptor. Another, preferred embodiment is an isolated human nucleic acid molecule encoding a human $\alpha_{1b}$ adrenergic receptor. Such a molecule may have coding sequences substantially the same as the coding sequence in FIGS. 2A–2H. The DNA molecule of FIGS. 2A–2H encodes the sequence of the human $\alpha_{1b}$ adrenergic receptor. Another, preferred embodiment is an isolated human nucleic acid molecule encoding a human $\alpha_{1c}$ adrenergic receptor. Such a molecule may have coding sequences substantially the same as the coding sequence in FIGS. 3A–3G. The DNA molecule of FIGS. 3A–3G encodes the sequence of the human $\alpha_{1c}$ adrenergic receptor. One means of isolating a nucleic acid molecule encoding a $\alpha_1$ adrenergic receptor is to screen a genomic DNA or cDNA library with a natural or artificially designed DNA probe, using methods well known in the art. In the preferred embodiment of this invention, $\alpha_1$ adrenergic receptors include the human $\alpha_{1a}$, human $\alpha_{1b}$ and human $\alpha_{1c}$ adrenergic receptors and the nucleic acid molecules encoding them were isolated by screening a human genomic DNA library and by further screening of a human cDNA library to obtain the sequence of the entire human $\alpha_{1a}$, human $\alpha_{1b}$ or human $\alpha_{1c}$ adrenergic receptor. To obtain a single nucleic acid molecule encoding the entire human $\alpha_{1a}$, $\alpha_{1b}$ or $\alpha_{1c}$ adrenergic receptor two or more DNA clones encoding portions of the same receptor were digested with DNA restriction endonuleases and ligated together with DNA ligase in the proper orientation using techniques known to one of skill in the art. DNA or cDNA molecules which encode a human $\alpha_{1a}$, $\alpha_{1b}$ or $\alpha_{1c}$ adrenergic receptor are used to obtain complementary genomic DNA, cDNA or RNA from human, mammalian or other animal sources, or to isolate related cDNA or genomic DNA clones by the screening of cDNA or genomic DNA libraries, by methods described in more detail below. Transcriptional regulatory elements from the 5' untranslated region of the isolated clone, and other stability, processing, transcription, translation, and tissue specificity determining regions from the 3' and 5' untranslated regions of the isolated gene are thereby obtained.

This invention provides an isolated nucleic acid molecule which has been so mutated as to be incapable of encoding a molecule having normal human $\alpha_1$ adrenergic receptor activity, and not expressing native human $\alpha_1$ adrenergic receptor. An example of a mutated nucleic acid molecule provided by this invention is an isolated nucleic acid molecule which has an in-frame stop codon inserted into the coding sequence such that the transcribed RNA is not translated into protein.

This invention provides a cDNA molecule encoding a human $\alpha_{1a}$ adrenergic receptor, wherein the cDNA molecule has a coding sequence substantially the same as the coding sequence shown in FIGS. 1A–1I. This invention also provides a cDNA molecule encoding a human $\alpha_{1b}$ adrenergic receptor, wherein the cDNA molecule has a coding sequence substantially the same as the coding sequence shown in FIGS. 2A–2H. This invention also provides a cDNA molecule encoding a human $\alpha_{1c}$ adrenergic receptor, wherein the cDNA molecule has a coding sequence substantially the same as the coding sequence shown in FIGS. 3A–3G. These molecules and their equivalents were obtained by the means further described below.

This invention provides an isolated protein which is a human $\alpha_1$ adrenergic receptor. In one embodiment of this invention, the protein is a human $\alpha_{1a}$ adrenergic receptor having an amino acid sequence substantially similar to the amino acid sequence shown in FIGS. 1A–1H. In another embodiment of this invention, the protein is a human $\alpha_{1b}$ adrenergic receptor having an amino acid sequence substantially similar to the amino acid sequence shown in FIGS. 2A–2H. In another embodiment of this invention, the protein is a human $\alpha_{1c}$ adrenergic receptor having an amino acid sequence substantially similar to the amino acid sequence shown in FIGS. 3A–3G. As used herein, the term "isolated protein" is intended to encompass a protein molecule free of other cellular components. One means for obtaining an isolated human $\alpha_1$ adrenergic receptor is to express DNA encoding the $\alpha_1$ adrenergic receptor in a suitable host, such as a bacterial, yeast, or mammalian cell, using methods well known to those skilled in the art, and recovering the human $\alpha_1$ adrenergic receptor after it has been expressed in such a host, again using methods well known in the art. The human $\alpha_1$ adrenergic receptor may also be isolated from cells which express it, in particular from cells which have been transfected with the expression vectors described below in more detail.

This invention also provides a vector comprising an isolated nucleic acid molecule such as DNA, RNA, or cDNA, encoding a human $\alpha_{1a}$ receptor. This invention also provides a vector comprising an isolated nucleic acid molecule such as DNA, RNA, or cDNA, encoding a human human $\alpha_{1b}$ adrenergic receptor. This invention also provides a vector comprising an isolated nucleic acid molecule such as DNA, RNA, or cDNA, encoding a human $\alpha_{1c}$ adrenergic receptor. Examples of vectors are viruses such as bacteriophages (such as phage lambda), cosmids, plasmids (such as pUC18, available from Pharmacia, Piscataway, N.J.), and other recombination vectors. Nucleic acid molecules are inserted into vector genomes by methods well known to those skilled in the art. Examples of such plasmids are plasmids comprising cDNA having a coding sequence substantially the same as: the coding sequence shown in FIGS. 1A–1I 2A–2H, and 3A–3G. Alternatively, to obtain these vectors, insert and vector DNA can both be exposed to a restriction enzyme to create complementary ends on both molecules which base pair with each other and are then ligated together with a ligase. Alternatively, linkers can be ligated to the insert DNA which correspond to a restriction site in the vector DNA, which is then digested with the restriction enzyme which cuts at that site. Other means are also available.

This invention also provides vectors comprising a DNA molecule encoding a human $\alpha_{1a}$, vectors comprising a DNA molecule encoding a human $\alpha_{1b}$ adrenergic receptor and vectors comprising a DNA molecule encoding a human $\alpha_{1c}$ adrenergic receptor adapted for expression in a bacterial cell, a yeast cell, or a mammalian cell which additionally comprise the regulatory elements necessary for expression of the DNA in the bacterial, yeast, or mammalian cells so located relative to the DNA encoding a human $\alpha_1$ adrenergic receptor as to permit expression thereof. DNA having coding sequences substantially the same as the coding sequence shown in FIGS. 1A–1I may be inserted into the vectors to express a human $\alpha_{1a}$ adrenergic receptor. DNA having coding sequences substantially the same as the coding sequence shown in FIGS. 2A–2H may be inserted into the vectors to express a human $\alpha_{1b}$ adrenergic receptor. DNA having coding sequences substantially the same as the coding sequence shown in FIGS. 3A–3G may be inserted into the vectors to express a human $\alpha_{1c}$ adrenergic receptor. Regulatory elements required for expression include promoter sequences to bind RNA polymerase and transcription initiation sequences for ribosome binding. For example, a bacterial expression vector includes a promoter such as the lac promoter and for transcription initiation the Shine- Dalgarno sequence and the start codon AUG (Maniatis, et al., Molecular Cloning, Cold Spring Harbor Laboratory, 1982). Similarly, a eukaryotic expression vector includes a heterologous or homologous promoter for RNA polymerase II, a downstream polyadenylation signal, the start codon AUG, and a termination codon for detachment of the ribosome. Such vectors may be obtained commercially or assembled from the sequences described by methods well known in the art, for example the methods described above for constructing vectors in general. Expression vectors are useful to produce cells that express a human $\alpha_1$ adrenergic receptor. Certain uses for such cells are described in more detail below.

In one embodiment of this invention a plasmid is adapted for expression in a bacterial, yeast, or, in particular, a mammalian cell wherein the plasmid comprises a DNA molecule encoding a human $\alpha_{1a}$ adrenergic receptor, a DNA molecule encoding a human $\alpha_{1b}$ adrenergic receptor or a DNA molecule encoding a human $\alpha_{1c}$ adrenergic receptor and the regulatory elements necessary for expression of the DNA in the bacterial, yeast, or mammalian cell so located relative to the DNA encoding a human $\alpha_1$ adrenergic receptor as to permit expression thereof. Suitable plasmids may include, but are not limited to plasmids adapted for expression in a mammalian cell, e.g., pCEXV-3 derived expression vector. Examples of such plasmids adapted for expression in a mammalian cell are plasmids comprising cDNA having coding sequences substantially the same as the coding sequence shown in FIGS. 1A–1I, 2A–2H, and 3A–3G and the regulatory elements necessary for expression of the DNA in the mammalian cell. These plasmids have been designated pcEXV-$\alpha_{1a}$ deposited under ATCC Accession No. 75319, pcEXV-$\alpha_{1b}$ deposited under ATCC Accession No. 75318, and pcEXV-$\alpha_{1c}$ deposited under ATCC Accession No. 75317, respectively. Those skilled in the art will readily appreciate that numerous plasmids adapted for expression in a mammalian cell which comprise DNA encoding human $\alpha_1$ adrenergic receptors and the regulatory elements necessary to express such DNA in the mammalian cell may be constructed utilizing existing plasmids and adapted as appropriate to contain the regulatory elements necessary to express the DNA in the mammalian cell. The plasmids may be constructed by the methods described above for expression vectors and vectors in general, and by other methods well known in the art.

The deposits discussed supra were made pursuant to, and in satisfaction of, the provisions of the Budapest Treaty on the International Recognition of the Deposit of Microorganisms for the Purpose of Patent Procedure with the American Type Culture Collection (ATCC), 12301 Parklawn Drive, Rockville, Md. 20852.

This invention provides a mammalian cell comprising a DNA molecule encoding a human $\alpha_1$ adrenergic receptor, such as a mammalian cell comprising a plasmid adapted for expression in a mammalian cell, which comprises a DNA molecule encoding a human $\alpha_1$ adrenergic receptor and the regulatory elements necessary for expression of the DNA in the mammalian cell so located relative to the DNA encoding a human $\alpha_1$ adrenergic receptor as to permit expression thereof. Numerous mammalian cells may be used as hosts, including, but not limited to, the mouse fibroblast cell NIH3T3, CHO cells, HeLa cells, Ltk$^-$ cells, human embryonic kidney cells, Cos cells, etc. Expression plasmids such as that described supra may be used to transfect mammalian cells by methods well known in the art such as calcium phosphate precipitation, or DNA encoding these human $\alpha_1$ adrenergic receptors may be otherwise introduced into mammalian cells, e.g., by microinjection, to obtain mammalian cells which comprise DNA, e.g., cDNA or a plasmid, encoding a human $\alpha_1$ adrenergic receptor.

This invention provides a nucleic acid probe comprising a nucleic acid molecule of at least 15 nucleotides capable of specifically hybridizing with a sequence included within the sequence of a nucleic acid molecule encoding a human $\alpha_{1a}$ adrenergic receptor, for example with a coding sequence included within the sequence shown in FIGS. 1A–1I. This invention also provides a nucleic acid probe comprising a nucleic acid molecule of at least 15 nucleotides capable of specifically hybridizing with a sequence included within the sequence of a nucleic acid molecule encoding a human $\alpha_{1b}$ adrenergic receptor, for example with a coding sequence included within the sequence shown in FIGS. 2A–2H. This invention also provides a nucleic acid probe comprising a nucleic acid molecule of at least 15 nucleotides capable of specifically hybridizing with a sequence included within the sequence of a nucleic acid molecule encoding a human $\alpha_{1c}$ adrenergic receptor, for example with a coding sequence included within the sequence shown in FIGS. 3A–3G. As used herein, the phrase "specifically hybridizing" means the ability of a nucleic acid molecule to recognize a nucleic acid sequence complementary to its own and to form double-helical segments through hydrogen bonding between complementary base pairs. Nucleic acid probe technology is well known to those skilled in the art who will readily appreciate that such probes may vary greatly in length and may be labeled with a detectable label, such as a radioisotope or fluorescent dye, to facilitate detection of the probe. Detection of nucleic acid encoding a human an adrenergic receptor is useful as a diagnostic test for any disease process in which levels of expression of the corresponding human $\alpha_{1a}$, $\alpha_{1b}$ or $\alpha_{1c}$ adrenergic receptor are altered. DNA probe molecules are produced by insertion of a DNA molecule which encodes a human $\alpha_{1a}$, human $\alpha_{1b}$, or human $\alpha_{1c}$ adrenergic receptor or fragments thereof into suitable vectors, such as plasmids or bacteriophages, followed by insertion into suitable bacterial host cells and replication and harvesting of the DNA probes, all using methods well known in the art. For example, the DNA may be extracted from a cell lysate using phenol and ethanol, digested with restriction enzymes corresponding to the insertion sites of the DNA into the vector (discussed above), electrophoresed, and cut out of the resulting gel. Examples of such DNA molecules are shown in FIGS. 1A–1I, 2A–2H, and 3A–3G. The probes are useful for "in situ" hybridization or in order to identify tissues which express this gene family, or for other hybridization assays for the presence of these genes or their mRNA in various biological tissues. In addition, synthesized oligonucleotides (produced by a DNA synthesizer) complementary to the sequence of a DNA molecule which encodes a human $\alpha_{1a}$ adrenergic receptor, or complementary to the sequence of a DNA molecule which encodes a human $\alpha_{1b}$ adrenergic receptor or complementary to the sequence of a DNA molecule which encodes a human $\alpha_{1c}$ adrenergic receptor are useful as probes for these genes, for their associated mRNA, or for the isolation of related genes by homology screening of genomic or cDNA libraries, or by the use of amplification techniques such as the Polymerase Chain Reaction.

This invention also provides a method for detecting expression of a human $\alpha_{1a}$ adrenergic receptor on the surface of a cell by detecting the presence of mRNA coding for a human $\alpha_{1a}$ adrenergic receptor. This invention also provides a method for detecting expression of a human $\alpha_{1b}$ adrenergic receptor on the surface of a cell by detecting the presence of mRNA coding for a human $\alpha_{1b}$ adrenergic receptor. This invention also provides a method for detecting expression of a human $\alpha_{1c}$ adrenergic receptor on the surface of a cell by detecting the presence of mRNA coding for a human $\alpha_{1c}$ adrenergic receptor. These methods comprise obtaining total mRNA from the cell using methods well known in the art and contacting the mRNA so obtained with a nucleic acid probe as described hereinabove, under hybridizing conditions, detecting the presence of mRNA hybridized to the probe, and thereby detecting the expression of a specific human $\alpha_1$ adrenergic receptor by the cell. Hybridization of probes to target nucleic acid molecules such as mRNA molecules employs techniques well known in the art. However, in one embodiment of this invention, nucleic acids are extracted by precipitation from lysed cells and the mRNA is isolated from the extract using a column which binds the poly-A tails of the mRNA molecules (Maniatis, T. et al., Molecular Cloning; Cold Spring Harbor Laboratory, pp.197–98 (1982)). The mRNA is then exposed to radioactively labelled probe on a nitrocellulose membrane, and the probe hybridizes to and thereby labels complementary mRNA sequences. Binding may be detected by autoradiography or scintillation counting. However, other methods for performing these steps are well known to those skilled in the art, and the discussion above is merely an example.

This invention provides an antisense oligonucleotide having a sequence capable of specifically binding with any sequences of an mRNA molecule which encodes a human $\alpha_{1a}$ adrenergic receptor so as to prevent translation of the human $\alpha_{1a}$ adrenergic receptor. This invention also provides an antisense oligonucleotide having a sequence capable of specifically binding with any sequences of an mRNA molecule which encodes a human $\alpha_{1b}$ adrenergic receptor so as to prevent translation of the human $\alpha_{1b}$ adrenergic receptor. This invention also provides an antisense oligonucleotide having a sequence capable of specifically binding with any sequences of an mRNA molecule which encodes a human $\alpha_{1c}$ adrenergic receptor so as to prevent translation of the human $\alpha_{1c}$ adrenergic receptor. As used herein, the phrase "specifically binding" means the ability of an antisense oligonucleotide to recognize a nucleic acid sequence complementary to its own and to form double-helical segments through hydrogen bonding between complementary base pairs. The antisense oligonucleotide may have a sequence capable of specifically binding with any sequences of the cDNA molecules whose sequences are shown in FIGS. 1A–1I, 2A–2H or 3A–3G. A particular example of an antisense oligonucleotide is an antisense oligonucleotide comprising chemical analogues of nucleotides which are known to one of skill in the art.

This invention also provides a pharmaceutical composition comprising an effective amount of the oligonucleotide described above effective to reduce expression of a human $\alpha_{1a}$ adrenergic receptor, by passing through a cell membrane and specifically binding with mRNA encoding the human $\alpha_{1a}$ adrenergic receptor in the cell so as to prevent its translation and a pharmaceutically acceptable hydrophobic carrier capable of passing through a cell membrane. This invention also provides a pharmaceutical composition comprising an effective amount of the oligonucleotide described above effective to reduce expression of a human $\alpha_{1b}$ adrenergic receptor in the cell so as to prevent its translation and a pharmaceutically acceptable hydrophobic carrier capable of passing through a cell membrane. This invention further provides a pharmaceutical composition comprising an effective amount of the oligonucleotide described above effective to reduce expression of a human $\alpha_{1c}$ adrenergic receptor in the cell so as to prevent its translation and a pharmaceutically acceptable hydrophobic carrier capable of passing through a cell membrane. As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The oligonucleotide may be coupled to a substance which inactivates mRNA, such as a ribozyme. The pharmaceutically acceptable hydrophobic carrier capable of passing through cell membranes may also comprise a structure which binds to a transporter specific for a selected cell type and is thereby taken up by cells of the selected cell type. The structure may be part of a protein known to bind a cell-type specific transporter, for example an insulin molecule, which would target pancreatic cells. DNA molecules having coding sequences substantially the same as the coding sequence shown in FIGS. 1A–1I, 2A–2H, or 3A–3G may be used as the oligonucleotides of the pharmaceutical composition.

This invention also provides a method of treating abnormalities which are alleviated by reduction of expression of a human $\alpha_1$ adrenergic receptor. This method comprises administering to a subject an effective amount of the pharmaceutical composition described above effective to reduce expression of the human $\alpha_1$ adrenergic receptor by the subject. This invention further provides a method of treating an abnormal condition related to $\alpha_1$ adrenergic receptor activity which comprises administering to a subject an amount of the pharmaceutical composition described above effective to reduce expression of the human $\alpha 1$ adrenergic receptor by the subject. Examples of such an abnormal condition include but are not limited to benign prostatic hypertrophy, coronary heart disease, hypertension, urinary retention, insulin resistance, atherosclerosis, sympathetic dystrophy syndrome, glaucoma, cardiac arrythymias erectile dysfunction, and Renaud's syndrome.

Antisense oligonucleotide drugs inhibit translation of mRNA encoding the human $\alpha 1a$, human $\alpha 1b$ or human $\alpha 1c$ adrenergic receptors. Synthetic antisense oligonucleotides, or other antisense chemical structures are designed to bind to mRNA encoding the human $\alpha 1a$ adrenergic receptor, to mRNA encoding the human $\alpha 1b$ adrenergic receptor or to mRNA encoding the human $\alpha 1c$ adrenergic receptor and inhibit translation of mRNA and are useful as drugs to inhibit expression of the human $\alpha_{1a}$ adrenergic receptor, the human $\alpha_{1b}$ adrenergic receptor or the human $\alpha_{1c}$ adrenergic receptor in patients. This invention provides a means to therapeutically alter levels of expression of the human $\alpha_{1a}$ adrenergic receptor, the human $\alpha_{1b}$ adrenergic receptor or the human $\alpha_{1c}$ adrenergic receptor by the use of a synthetic antisense oligonucleotide drug (SAOD) which inhibits translation of mRNA encoding these $\alpha_1$ adrenergic receptors. Synthetic antisense oligonucleotides, or other antisense chemical structures designed to recognize and selectively bind to mRNA, are constructed to be complementary to portions of the nucleotide sequences shown in FIGS. 1A–1I, 2A–2H, or 3A–3G of DNA, RNA or of chemically modified, artificial nucleic acids. The SAOD is designed to be stable in the blood stream for administration to patients by injection, or in laboratory cell culture conditions, for administration to cells removed from the patient. The SAOD is designed to be capable of passing through cell membranes in order to enter the cytoplasm of the cell by virtue of physical nd chemical properties of the SAOD which render it capable of passing through cell membranes (e.g., by designing small, hydrophobic SAOD chemical structures) or by virtue of specific transport systems in the cell which recognize and transport the SAOD into the cell. In addition, the SAOD can be designed for administration only to certain selected cell populations by targeting the SAOD to be recognized by specific cellular uptake mechanisms which bind and take up the SAOD only within certain selected cell populations. For example, the SAOD may be designed to bind to a transporter found only in a certain cell type, as discussed above. The SAOD is also designed to recognize and selectively bind to the target mRNA sequence, which may correspond to a sequence contained within the sequences shown in FIGS. 1A–1I, 2A–2H, or 3A–3G by virtue of complementary base pairing to the mRNA. Finally, the SAOD is designed to inactivate the target mRNA sequence by any of three mechanisms: 2) by binding to the target mRNA and thus inducing degradation of the mRNA by intrinsic cellular mechanisms such as mRNA target by interfering with the binding of translation-regulating factors or of other chemical structures, such as ribozyme sequences or reactive chemical groups. which either degrade or chemically modify the target mRNA. Synthetic antisense oligonucleotide drugs have been shown to be capable of the properties described above when directed against mRNA targets (J. S. Cohen, Trends in Pharm. Sci 10, 435 (1989); H. M. Weintraub, Sci. AM. January (1990) p. 40). In addition, coupling of ribozymes to antisense oligonucleotides is a promising strategy for inactivating target mRNA (N. Sarver et al., Science 247, 1222 (1990)). An SAOD serves as an effective therapeutic agent if it is designed to be administered to a patient by injection, or if the patient's target cells are removed, treated with the SAOD in the laboratory, and replaced in the patient. In this manner, an SAOD serves as a therapy to reduce human $\alpha_1$ adrenergic receptor expression in particular target cells of a patient, in any clinical condition which may benefit from reduced expression of a specific human $\alpha_1$ adrenergic receptor.

This invention provides an antibody directed to a human $\alpha_{1a}$ adrenergic receptor. This antibody may comprise, for example, a monoclonal antibody directed to an epitope of a human $\alpha_{1a}$ adrenergic receptor present on the surface of a cell, the epitope having an amino acid sequence substantially the same as an amino acid sequence for a cell surface epitope of the human $\alpha_{1a}$ adrenergic receptor included in the amino acid sequence shown in FIGS. 1A–1I. This invention also provides an antibody directed to a human $\alpha_{1b}$ adrenergic receptor. This antibody may comprise, for example, a monoclonal antibody directed to an epitope of a human $\alpha_{1b}$ adrenergic receptor present on the surface of a cell, the epitope having an amino acid sequence substantially the same as an amino acid sequence for a cell surface epitope of the human $\alpha_{1b}$ adrenergic receptor included in the amino acid sequence shown in FIGS. 2A–2H. This invention also provides an antibody directed to a human $\alpha_{1c}$ adrenergic receptor. This antibody may comprise, for example, a monoclonal antibody directed to an epitope of a human α1c adrenergic receptor present on the surface of a cell, the epitope having an amino acid sequence substantially the same as an amino acid sequence for a cell surface epitope of the human α1c adrenergic receptor included in the amino acid sequence shown in FIGS. 3A–3G. Amino acid sequences may be analyzed by methods well known to those skilled in the art to determine whether they produce hydrophobic or hydrophilic regions in the proteins which they build.

In the case of cell membrane proteins, hydrophobic regions are well known to form the part of the protein that is inserted into the lipid bilayer which forms the cell membrane, while hydrophilic regions are located on the cell surface, in an aqueous environment. Therefore antibodies to the hydrophilic amino acid sequences shown in FIGS. 1A–1I will bind to a surface epitope of the human α1a adrenergic receptor, antibodies to the hydrophilic amino acid sequences shown in FIGS. 2A–2H will bind to a surface epitope of a human α1b adrenergic receptor, and antibodies to the hydrophilic amino acid sequences shown in FIGS. 3A–3G will bind to a surface epitope of a human α1c adrenergic receptor as described. Antibodies directed to human α1 adrenergic receptors may be serum-derived or monoclonal and are prepared using methods well known in the art. For example, monoclonal antibodies are prepared using hybridoma technology by fusing antibody producing B cells from immunized animals with myeloma cells and selecting the resulting hybridoma cell line producing the desired antibody. Cells such as NIH3T3 cells or Ltk$^-$ cells may be used as immunogens to raise such an antibody. Alternatively, synthetic peptides may be prepared using commercially available machines and the amino acid sequence shown in FIGS. 1A–1I, 2A–2H, and 3A–3G. As a still further alternative DNA, such as a cDNA or a fragment thereof, may be cloned and expressed and the resulting polypeptide recovered and used as an immunogen. These antibodies are useful to detect the presence of human α1 adrenergic receptors encoded by the isolated DNA, or to inhibit the function of α1 adrenergic receptors in living animals, in humans, or in biological tissues or fluids isolated from animals or humans.

This invention provides a pharmaceutical composition which comprises an effective amount of an antibody directed to an epitope of a human $\alpha_{1a}$ adrenergic receptor and a pharmaceutically acceptable carrier. A monoclonal antibody directed to an epitope of a human $\alpha_{1a}$ adrenergic receptor present on the surface of a cell which has an amino acid sequence substantially the same as an amino acid sequence for a cell surface epitope of the human $\alpha_{1a}$ adrenergic receptor present on the surface of a cell which has an amino acid sequence substantially the same as an amino acid sequence for a cell surface epitope of the human $\alpha_{1a}$ adrenergic receptor included in the amino acid sequence shown in FIGS. 1A–1I is useful for this purpose. This invention also provides a pharmaceutical composition which comprises an effective amount of an antibody directed to an epitope of a human $\alpha_{1b}$ adrenergic receptor, effective to block binding of naturally occurring substrates to the human $\alpha_{1b}$ adrenergic receptor and a pharmaceutically acceptable carrier. A monoclonal antibody directed to an epitope of a human $\alpha_{1b}$ adrenergic receptor present on the surface of a cell which has an amino acid sequence substantially the same as an amino acid sequence for a cell surface epitope of the human $\alpha_{1b}$ adrenergic receptor included in the amino acid sequence shown in FIGS. 2A–2H is useful for this purpose. This invention provides a pharmaceutical composition which comprises an effective amount of an antibody directed to an epitope of a human $\alpha_{1c}$ adrenergic receptor effective to block binding of naturally occurring substrates to the human $\alpha_{1c}$ adrenergic receptor and a pharmaceutically acceptable carrier. A monoclonal antibody directed to an epitope of a human $\alpha_{1c}$ adrenergic receptor present on the surface of the cell which has an amino acid sequence substantially the same as an amino acid sequence for a cell surface epitope of the human $\alpha_{1c}$ adrenergic receptor included in the amino acid sequence shown in FIGS. 3A–3G is useful for this purpose.

This invention also provides a method of treating abnormalities in a subject which are alleviated by reduction of expression of a specific human $\alpha_1$ adrenergic receptor. The method comprises administering to the subject an effective amount of the pharmaceutical composition described above effective to block binding of naturally occurring substrates to the human $\alpha_1$ adrenergic receptor and thereby alleviate abnormalities resulting from overexpression of the human $\alpha_1$ adrenergic receptor. Binding of the antibody to the human $\alpha_1$ adrenergic receptor from functioning, thereby neutralizing the effects of overexpression. The monoclonal antibodies described above are useful for this purpose. This invention additionally provides a method of treating an abnormal condition related to an excess of a specific human $\alpha_1$ adrenergic receptor activity which comprises administering to a subject an amount of the pharmaceutical composition described above effective to block binding of naturally occurring substrates to the human $\alpha 1$ adrenergic receptor and thereby alleviate the abnormal condition. Examples of such an abnormal condition include but are not limited to benign prostatic hypertrophy, coronary heart disease, insulin resistance, atherosclerosis, sympathetic dystrophy syndrome, glaucoma, cardiac arrythymias, hypertension, urinary retention, erectile dysfunction, and Renaud's syndrome.

This invention provides methods of detecting the presence of a specific human $\alpha 1$ adrenergic receptor on the surface of a cell which comprises contacting the cell with an antibody directed to a specific human $\alpha 1$ adrenergic receptor, under conditions permitting binding of the antibody to the human $\alpha 1$ adrenergic receptor, under conditions permitting binding of the antibody to the human $\alpha 1$ adrenergic receptor, detecting the presence of any antibody bound to the $\alpha 1$ adrenergic receptor, and thereby the presence of the specific human $\alpha 1$ adrenergic receptor on the surface of the cell. Such methods are useful for determining whether a given cell is defective in expression of a specific human $\alpha 1$ adrenergic receptor. Bound antibodies are detected by methods well known in the art, for example by binding fluorescent markers to the antibodies and examining the cell sample under a fluorescence microscope to detect fluorescence on a cell indicative of antibody binding. The monoclonal antibodies described above are useful for this purpose.

This invention provides a transgenic nonhuman mammal comprising DNA encoding DNA encoding a human $\alpha_{1a}$ adrenergic receptor. This invention also provides a transgenic nonhuman mammal comprising DNA encoding a human $\alpha_{1b}$ adrenergic receptor. This invention also provides a transgenic nonhuman mammal comprising DNA encoding a human $\alpha_{1c}$ adrenergic receptor.

This invention also provides a transgenic nonhuman mammal comprising DNA encoding a human $\alpha_{1a}$ adrenergic receptor so mutated as to be incapable of normal human $\alpha_{1a}$ adrenergic receptor activity, and not expressing native human $\alpha 1a$ adrenergic receptor activity, and not expressing native human $\alpha 1a$ adrenergic receptor. This invention also provides a transgenic nonhuman mammal comprising DNA encoding a human $\alpha_{1b}$ adrenergic receptor so mutated as to be incapable of normal human $\alpha 1b$ adrenergic receptor activity, and not expressing native human $\alpha 1b$ adrenergic receptor. This invention also provides a transgenic nonhuman mammal comprising DNA encoding a human $\alpha_{1c}$ adrenergic receptor so mutated as to be incapable of normal human $\alpha 1c$ adrenergic receptor activity, and not expressing native human $\alpha 1c$ adrenergic receptor.

This invention provides a transgenic non-human animal whose genome comprises DNA encoding a human $\alpha_{1a}$ adrenergic receptor so placed as to be transcribed into antisense mRNA which is complementary to mRNA encoding a human $\alpha_{1a}$ adrenergic receptor thereby reducing its translation. This invention also provides a transgenic non-human mammal whose genome comprises DNA encoding a human $\alpha_{1b}$ adrenergic receptor so placed as to be transcribed into antisense mRNA which is complementary to mRNA encoding the human $\alpha_{1b}$ adrenergic receptor and which hybridizes to mRNA encoding a human $\alpha_{1b}$ adrenergic receptor thereby reducing its translation. This invention provides a transgenic non-human animal whose genome comprises DNA encoding a human $\alpha_{1c}$ adrenergic receptor so placed as to be transcribed into antisense mRNA which is complementary to mRNA encoding a human $\alpha_{1c}$ adrenergic receptor and which hybridizes to mRNA encoding the human $\alpha_{1c}$ adrenergic receptor thereby reducing its translation. The DNA may additionally comprise an inducible promoter or additionally comprise tissue specific regulatory elements, so that expression can be induced, or restricted to specific cell types. Examples of DNA are DNA or cDNA molecules having a coding sequence substantially the same as the coding sequences shown in FIGS. 1A–1I, 2A–2H, or 3A–3G. An example of a transgenic animal is a transgenic mouse. Examples of tissue specificity-determining regions are the metallothionein promoter (Low, M. J., Lechan, R. M., Hammer, R. E. et al. Science 231:1002–1004 (1986) and the L7 promoter (Oberdick, J., Smeyne, R. J., Mann, J. R., Jackson, S. and Morgan, J. I. Science 248:223–226 (1990)).

Animal model systems which elucidate the physiological and behavioral roles of human $\alpha_1$ adrenergic receptors are produced by creating transgenic animals in which the increased or decreased, or the amino acid sequence of the expressed $\alpha_1$ adrenergic receptor is altered, by a variety of techniques. Examples of these techniques include, but are not limited to: 1) Insertion of normal or mutant versions of DNA encoding a human $\alpha_1$ adrenergic receptor or homologous animal versions of these genes, by microinjection, retroviral infection or other means well known to those skilled in the art, into appropriate fertilized embryos in order to produce a transgenic animal (Hogan B et al., Manipulating the Mouse Embryo, A Laboratory Manual, Cold Spring Harbor Laboratory (1986)) or, 2) Homologous recombination (Capecchi M. R. Science 244:1288–1292 (1989); Zimmer, A. and Gruss, P. Nature 338:150–153 (1989)) of mutant or normal, human or animal version of the genes encoding $\alpha 1$ adrenergic receptors with the native gene locus in transgenic animals to alter the regulation of expression or the structure $\alpha 1$ of these $\alpha 1$ adrenergic receptors. The technique of homologous $\alpha_1$ adrenergic receptors. The technique of homologous recombination is well known in the art. It replaces the native gene with the inserted gene and so is useful for producing an animal that cannot express native $\alpha_1$ adrenergic receptor but does express, for example an inserted mutant human $\alpha_1$ adrenergic receptor, which has replaced the native $\alpha_1$ adrenergic receptor in the animal's genome by recombination, resulting in underexpression of the $\alpha_1$ adrenergic receptor. Microinjection adds genes to the genome, but does not remove them, and so is useful for producing an animal which expresses its own and added $\alpha_1$ adrenergic receptors, resulting in overexpression of the $\alpha_1$ adrenergic receptor.

One means available for producing a transgenic animal, with a mouse as an example, is as follows: Female mice are mated, and the resulting fertilized eggs are dissected out of their oviducts. The eggs are stored in an appropriate medium such as M2 medium (Hogan B et al., Manipulating the Mouse Embryo, A Laboratory Manual, Cold Spring Harbor Laboratory (1986)). DNA or cDNA encoding a human $\alpha_1$ adrenergic receptor is purified from a vector (such as plasmids pCEXV-$\alpha_{1b}$, or pCEXV-$\alpha_{1c}$ described above) by methods well known in the art. Inducible promoters may be fused with the coding region of the DNA to provide an experimental means to regulate expression of the trans-gene. Alternatively or in addition, tissue specific regulatory elements may be fused with the coding region to permit tissue-specific expression of the trans-gene. The DNA, in an appropriately buffered solution, is put into a microinjection needle (which may be made from capillary tubing using a pipet puller) and the egg to be injected is put in a depression slide. The needle is inserted into the pronucleus of the egg, and the DNA solution is injected. The injected egg is then transferred into the oviduct of a pseudopregnant mouse (a mouse stimulated by the appropriate hormones to maintain pregnancy but which is not actually pregnant), where it proceeds to the uterus, implants, and develops to term. As noted above, microinjection is not the only method for inserting DNA into the egg cell, and is used here only for exemplary purposes.

Since the normal action of $\alpha_1$ adrenergic-specific drugs is to activate or to inhibit the $\alpha_1$ adrenergic receptor, the transgenic animal model systems described above are useful for testing the biological activity of drugs directed against specific human $\alpha_1$ adrenergic receptors even before such drugs become available. These animal model systems are useful for predicting or evaluating possible therapeutic applications of drugs which activate or inhibit these human $\alpha_1$ adrenergic receptors by inducing or inhibiting expression of the native or transgene and thus increasing or decreasing expression of normal or mutant human $\alpha_1$ adrenergic receptor in the living animal. Thus, a model system is produced in which the biological activity of drugs directed against these human $\alpha_1$ adrenergic receptors are evaluated before such drugs become available. The transgenic animals which over or under produce a specific human $\alpha_1$ adrenergic over or under produce a specific human $\alpha_1$ adrenergic over or under produce a specific human $\alpha_1$ adrenergic receptor indicate by their physiological state whether over or under production of the human $\alpha_1$ adrenergic receptor is therapeutically useful. It is therefore useful to evaluate drug action based on the transgenic model system. One use is based on the fact that it is well known in the art that a drug such as an antidepressant acts by blocking neurotransmitter uptake, and thereby increases the amount of neurotransmitter in the synaptic cleft. The physiological result of this action is to stimulate the production of less human $\alpha_1$ adrenergic receptor by the affected cells, leading eventually to underexpression. Therefore, an animal which underexpresses human $\alpha_1$ adrenergic receptor is useful as a test system to investigate whether the actions of such drugs which result in under expression are in fact therapeutic. Another use is that if overexpression is found to lead abnormalities, then a drug which down-regulates or acts as an antagonist to the human $\alpha_1$ adrenergic receptor is indicated as worth developing, and if a promising therapeutic application is uncovered by these animal model systems, activation or inhibition of the specific human $\alpha_1$ adrenergic receptor or antagonist drugs directed against these human $\alpha_1$ adrenergic receptors or by any method which increases or decreases the expression of these $\alpha_1$ adrenergic receptors in man.

Further provided by this invention is a method of determining the physiological effects of expressing varying levels of a human $\alpha_1$ adrenergic receptor which comprises producing a transgenic nonhuman animal whose levels of $\alpha_1$ adrenergic receptor expression are varied by use of an inducible promoter which regulates human $\alpha_1$ adrenergic receptor expression. This invention also provides a method for determining the physiological effects of expressing varying levels of human $\alpha_1$ adrenergic receptors which comprise producing a panel of transgenic nonhuman animals each expressing a different amount of a human $\alpha_1$ adrenergic receptor. Such animals may be produced by introducing different amounts of DNA encoding a human $\alpha_1$ adrenergic receptor into the oocytes from which the transgenic animals are developed.

This invention also provides a method for identifying a substance capable of alleviating abnormalities resulting from overexpression of a human $\alpha_1$ adrenergic receptor comprising administering the substance to a transgenic nonhuman mammal expressing at least one artificially introduced DNA molecule encoding a human $\alpha_1$ adrenergic receptor and determining whether the substance alleviates the physical and behavioral abnormalities displayed by the transgenic nonhuman mammal as a result of overexpression of a human $\alpha_1$ adrenergic receptor. As used herein, the term "substance" means a compound or composition which may be natural, synthetic, or a product derived from screening. Examples of DNA molecules are DNA or cDNA molecules having a coding sequence substantially the same as the coding sequences shown in FIGS. 1A–1I, 2A–2H, or 3A–3G.

This invention provides a pharmaceutical composition comprising an amount of the substance described supra effective to alleviate the abnormalities resulting from overexpression of a human $\alpha_{1a}$ adrenergic receptor and a pharmaceutically acceptable carrier. This invention provides a pharmaceutical composition comprising an amount of the substance described supra effective to alleviate the abnormalities resulting from overexpression of a human $\alpha_{1b}$ adrenergic receptor and a pharmaceutically acceptable carrier. This invention also provides a pharmaceutical composition comprising an amount of the substance described supra effective to alleviate the abnormalities resulting from overexpression of a human $\alpha_{1c}$ adrenergic receptor and a pharmaceutically acceptable carrier.

This invention further provides a method for treating the abnormalities resulting from overexpression of a human $\alpha_1$ adrenergic receptor which comprises administering to a subject an amount of the pharmaceutical composition described above effective to alleviate the abnormalities resulting from overexpression of the human $\alpha_1$ adrenergic receptor.

This invention provides a method for identifying a substance capable of alleviating the abnormalities resulting from underexpression of a human $\alpha_1$ adrenergic receptor comprising administering the substance to the transgenic nonhuman mammal described above which expresses only a nonfunctional human $\alpha_1$ adrenergic receptor and determining whether the substance alleviates the physical and behavioral abnormalities displayed by the transgenic nonhuman mammal as a result of underexpression of the human $\alpha_1$ adrenergic receptor.

This invention also provides a pharmaceutical composition comprising an amount of a substance effective to alleviate abnormalities resulting from underexpression of a human $\alpha_1$ adrenergic receptor and a pharmaceutically acceptable carrier.

This invention also provides a method for treating the abnormalities resulting from underexpression of a human $\alpha_1$ adrenergic receptor which comprises administering to a subject an amount of the pharmaceutical composition described above effective to alleviate the abnormalities resulting from underexpression of a human $\alpha_1$ adrenergic receptor.

This invention provides a method for diagnosing a predisposition to a disorder associated with the expression of a specific human $\alpha_1$ adrenergic receptor allele which comprises: a) obtaining DNA of subjects suffering from the disorder; b) performing a restriction digest of the DNA with a panel of restriction enzymes; c) electrophoretically separating the resulting DNA fragments on a sizing gel; d) contacting the resulting gel with a nucleic acid probe capable of specifically hybridizing to DNA encoding a human $\alpha_1$ adrenergic receptor and labelled bands which have hybridized to the DNA encoding a human $\alpha^1$ adrenergic receptor labelled with a detectable marker to create a unique band pattern specific to the DNA of subjects suffering from the disorder; f) preparing DNA obtained for diagnosis by steps a–e; and g) comparing the unique band pattern specific to the DNA of subjects suffering from the disorder from step e and the DNA obtained for diagnosis from step f to determine whether the patterns are the same or different and thereby to diagnose predisposition to the disorder if the patterns are the same. This method may also be used to diagnose a disorder associated with the expression of a specific human $\alpha_1$ adrenergic receptor allele.

This invention provides a method of preparing an isolated human $\alpha_1$ adrenergic receptor which comprises inducing cells to express the human $\alpha_1$ adrenergic receptor, recovering the $\alpha_1$ adrenergic receptor from the resulting cells, and purifying the $\alpha_1$ adrenergic receptor so recovered. An example of an isolated human $\alpha_{1a}$ adrenergic receptor is an isolated protein having substantially the same amino acid sequence as the amino acid sequence shown in FIGS. 1A–1I. An example of an isolated human $\alpha_{1b}$ adrenergic receptor is an isolated protein having substantially the same amino acid sequence as the amino acid sequence shown in FIGS. 1A–1I. An example of an isolated human $\alpha_{1b}$ adrenergic receptor is an isolated protein having substantially the same amino acid sequence shown in FIGS. 2A–2H. An example of an isolated human $\alpha_{1c}$ adrenergic receptor is an isolated protein having substantially the same amino acid sequence shown in FIGS. 3A–3G. For example, cells can be induced to express human $\alpha_1$ adrenergic receptor by exposure to substances such as hormones. The cells can then be homogenized and the human $\alpha_1$ adrenergic receptor isolated from the homogenate using an affinity column comprising, for example, epinephrine, norepinephrine, or another substance which is known to bind to the human $\alpha_1$ adrenergic receptor. The resulting fractions can then be purified by contacting them with an ion exchange column, and determining which fraction contains human $\alpha_1$ adrenergic receptor activity or binds anti-human $\alpha_1$ adrenergic receptor activity or binds anti-human $\alpha 1$ adrenergic receptor antibodies.

This invention provides a method of preparing the isolated human $\alpha_{1a}$ adrenergic receptor which comprises inserting nucleic acid encoding the human $\alpha_{1a}$ adrenergic receptor in a suitable vector, inserting the resulting vector in a suitable host cell, recovering the $\alpha_{1a}$ adrenergic receptor produced by the resulting cell, and purifying the $\alpha_{1a}$ adrenergic receptor so recovered. An example of an isolated human $\alpha_{1a}$ adrenergic receptor is an isolated protein having substantially the same amino acid sequence as the amino acid sequence shown in FIGS. 1A–1I. This invention also provides a method of preparing the isolated human $\alpha_{1b}$ adrenergic receptor which comprises inserting nucleic acid encoding the human $\alpha_{1b}$ adrenergic receptor in a suitable vector, inserting the resulting vector in a suitable host, recovering the $\alpha_{1b}$ adrenergic receptor produced by the resulting cell, and purifying the $\alpha_{1c}$ adrenergic receptor so recovered. These methods for preparing human $\alpha_1$ adrenergic receptor uses recombinant DNA technology methods well known in the art. For example, isolated nucleic acid encoding a human $\alpha_1$ adrenergic receptor is inserted in a suitable vector, such as an expression vector. A suitable host cell, such as a bacterial cell, or a eukaryotic cell such as a yeast cell is transfected with the vector. The human $\alpha_1$ adrenergic receptor is isolated from the culture medium by affinity purification or by chromatography or by other methods well known in the art.

This invention provides a method of determining whether a ligand not known to be capable of binding to a human $\alpha_1$ adrenergic receptor can bind to a human $\alpha_1$ adrenergic receptor, which comprises contacting a mammalian cell comprising a plasmid adapted for expression in a mammalian cell which further comprises a DNA molecule which expresses a human $\alpha_1$ adrenergic receptor on the cell surface with the ligand under conditions permitting binding of ligands known to bind to the human $\alpha_1$ adrenergic receptor, detecting the presence of any ligand bound to the human $\alpha_1$ adrenergic receptor. The DNA in the cell may have a coding sequence substantially the same as the coding sequences shown in FIGS. 1A–1I, 2A–2h, or 3A–3G, preferably, the mammalian cell is nonneuronal in origin. An example of a nonneuronal mammalian cell is a Cos7 cell. The preferred method for determining whether a ligand is capable of binding to the human $\alpha_1$ adrenergic receptor comprises contacting a transfected nonneuronal mammalian cell (i.e. a cell that does not naturally express any type of human $\alpha_1$ adrenergic receptor, thus will only express such human $\alpha_1$ adrenergic receptor if it is transfected into the cell) expressing a human $\alpha_1$ adrenergic receptor on it surface, or contacting $\alpha_1$ membrane preparation derived from such a transfected cell, with the ligand under conditions which are known to prevail, and thus be associated with in vivo binding of the substrates to a human $\alpha_1$ adrenergic receptor, detecting the presence of any of the ligand being tested bound to the human $\alpha_1$ adrenergic receptor on the surface of the cell, and thereby determining whether the ligand binds to the human $\alpha_1$ adrenergic receptor. This response system is obtained by transfection of isolated DNA into a suitable host cell. Such a host system might be isolated from pre-existing cell lines, or can be generated by inserting appropriate components into existing cell lines. Such a transfection system provides a complete response system for investigation or assay of the functional activity of human $\alpha_1$ adrenergic receptors with ligands as described above. Transfection systems are useful as living cell cultures for competitive binding assays between known or candidate drugs and substrates which bind to the human $\alpha_1$ adrenergic receptor and which are labeled by radioactive, spectroscopic or other reagents. Membrane preparations containing the transporter isolated from transfected cells are also useful for these competitive binding assays. A transfection system constitutes a "drug discovery system" useful for the identification of natural or synthetic compounds with potential for drug development that can be further modified or used directly as therapeutic compounds to activate or inhibit the natural functions of a specific human $\alpha_1$ adrenergic receptor. The transfection system is also useful for determining the affinity and efficacy of known drugs at human $\alpha_1$ adrenergic receptor binding sites.

This invention provides a method for identifying a ligand which interacts with, and activates or blocks the activation of, a human $\alpha_1$ adrenergic receptor on the surface of the cell, which comprises contacting a mammalian cell which comprises a plasmid adapted for expression in a mammalian cell which further comprises a DNA molecule which expresses a human $\alpha_1$ adrenergic receptor on the cell surface with the ligand, determining whether the ligand activates or blocks the activation of the receptor using a bioassay such as a second messenger assays, and thereby identifying a ligand which interacts with, and activates or blocks the activation of, a human $\alpha_1$ adrenergic receptor.

This invention provides functional assays for identifying ligands and drugs which bind to and activate or inhibit a specific human $\alpha 1$ adrenergic receptor activity.

This invention provides a method for identifying a ligand which is capable of binding to and activating or inhibiting a human $\alpha_1$ adrenergic receptor, which comprises contacting a mammalian cell, wherein the membrane lipids have been labelled by prior incubation with a labelled myo-inositol phosphate molecule, the mammalian cell comprising a plasmid adapted for expression in a mammalian cell which further comprises a DNA molecule which expresses a human $\alpha_1$ adrenergic receptor with the ligand and identifying an inositol phosphate metabolite released from the membrane lipid as a result of ligand binding to and activating an $\alpha_1$ adrenergic receptor.

This invention provides method for identifying a ligand that is capable of binding to and activating or inhibiting a human $\alpha_1$ adrenergic receptor, where in the binding of ligand to the adrenergic receptor results in a physiological response, which comprises contacting a mammalian cell which further comprises a DNA molecule which expresses a human $\alpha_1$ adrenergic receptor with a calcium sensitive fluorescent indicator, removing the indicator that has not been taken up by the cell, contacting the cells with the ligand and identifying an increase or decrease in intracellular $Ca^{+2}$ as a result of ligand binding to and activating receptors.

Transformed mammalian cell s for identifying the ligands and drugs that affect the functional properties of the human a adrenergic receptor include 292-$\alpha 1\alpha$-10, C-$\alpha 1b$-6 and C-$\alpha 1c$-7.

This invention also provides a method of screening drugs to identify drugs which interact with, and bind to, a human $\alpha_1$ adrenergic receptor on the surface of a cell, which comprises contacting a mammalian cell which comprises a plasmid adapted for expression in a mammalian cell which further comprises a DNA molecule which expresses a human $\alpha_1$ adrenergic receptor on the cell surface with a plurality of drugs, determining those drugs which bind to the human $\alpha_1$ adrenergic receptor expressed on the cell surface of the mammalian cell, and thereby identifying drugs which interact with, and bind to, the human $\alpha_1$ adrenergic receptor. Various methods of detection may be employed. The drugs may be "labeled" by association with a detectable marker substance (e.g., radiolabel or a non-isotopic label such as biotin). The DNA in the cell may have a coding sequence substantially the same as the coding sequences shown in FIGS. 1A–1I, 2A–2H or 3A–3G.

Preferably, the mammalian cell is nonneuronal in origin. An example of a nonneuronal mammalian cell is a Cos7 cell. Drug candidates are identified by choosing chemical compounds which bind with high affinity to the human $\alpha_1$ adrenergic receptor expressed on the cell surface in transfected cells, using radioligand binding methods well known in the art, examples of which are shown in the binding assays described herein. Drug candidates are also screened for selectivity by identifying compounds which bind with high affinity to one particular human $\alpha_1$ adrenergic receptor subtype but do not bind with high affinity to any other human $\alpha_1$ adrenergic receptor subtype or to any other known receptor site. Because selective, high affinity compounds interact primarily with the target human $\alpha_1$ adrenergic site after administration to the patient, the chances of producing a drug with unwanted side effects are minimized by this approach. This invention provides a pharmaceutical composition comprising a drug identified by the method described above and a pharmaceutically acceptable carrier. As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. Once the candidate drug has been shown to be adequately bio-available following a particular route of administration, for example orally or by injection (adequate therapeutic concentrations must be maintained at the site of action for an adequate period to gain the desired therapeutic benefit), and has been shown to be non-toxic and therapeutically effective in appropriate disease models, the drug may be administered to patients by that route of administration determined to make the drug bio-available, in an appropriate solid or solution formulation, to gain the desired therapeutic benefit. This invention also provides a method for treating an abnormal condition related to an excess of activity of a human $\alpha_1$ adrenergic receptor subtype, which comprises administering a patient an amount of a pharmaceutical composition described above, effective to reduce $\alpha_1$ adrenergic activity as a result of naturally occurring substrate binding to and activating a specific $\alpha_1$ adrenergic receptor. Examples of such abnormalities related to an excess of activity of a human $\alpha_1$ adrenergic receptor subtype include but are limited to benign prostatic hypertrophy, coronary heart disease, hypertension, urinary retention, insulin resistance, atherosclerosis, sympathetic dystrophy syndrome, glaucoma, cardiac arrythymias erectile dysfunction, and Renaud's syndrome.

This invention also provides a method of treating abnormalities which are alleviated by an increase in the activity of a specific human $\alpha_1$ adrenergic receptor, which comprises administering a patient an amount of a pharmaceutical composition described above, effective to increase the activity of the specific human $\alpha_1$ adrenergic receptor thereby alleviating abnormalities resulting from abnormally low receptor activity. Examples of such abnormalities related to a decrease in the activity of a specific human $\alpha_1$ adrenergic receptor include but are not limited to congestive heart failure, urinary incontinence, nasal congestion and hypotension.

Applicants have identified individual human $\alpha_1$ adrenergic receptor subtypes and have described methods for the identification of pharmacological compounds for therapeutic treatments. Pharmacological compounds which are directed against a specific human adrenergic receptor subtype provide effective new therapies with minimal side effects.

Elucidation of the molecular structures of the neuronal human $\alpha_1$ adrenergic receptors transporters is an important step in the understanding of $\alpha$-adrenergic neurotransmission. This disclosure reports the isolation, the nucleic acid sequence, and functional expression of DNA clones isolated from human brain which encode human $\alpha_1$ adrenergic receptor. The identification of these human $\alpha_1$ adrenergic receptor will play a pivotal role in elucidating the molecular mechanisms underlying $\alpha$-adrenergic transmission, and should also aid in the development of novel therapeutic agents.

DNA clones encoding human $\alpha_1$ adrenergic receptor have been isolated from human brain, and their functional properties have been examined in mammalian cells.

This invention identifies for the first time three new human $\alpha_1$ adrenergic receptor, their amino acid sequences, and their human genes. The information and experimental tools provided by this discovery are useful to generate new therapeutic agents, and new therapeutic or diagnostic assays for these new human receptors, their associated mRNA molecules or their associated genomic DNAs. The information and experimental tools provided by this discovery will be useful to generate new therapeutic agents, and new therapeutic or diagnostic assays for these new human receptors, their associates mRNA molecules, or their associated genomic DNAs.

Specifically, this invention relates to the first isolation of human DNA clones encoding three $\alpha_1$-adrenergic receptor. In addition, the human $\alpha_1$ adrenergic receptor have been expressed in mammalian cells by transfecting the cells with the plasmids pcEXV-$\alpha_{1a}$, pcEXV-$\alpha_{1c}$. The pharmacological binding properties of these receptor proteins have been determined, and these binding properties classify these receptor proteins as $\alpha_1$ adrenergic receptor. Mammalian cell lines expressing the human $\alpha_1$ adrenergic receptor on the cell surface have been constructed, thus establishing the first well-defined, cultured cell lines with which to study human $\alpha_1$ adrenergic receptor. Examples of transformed mammalian cells, expressing human $\alpha_1$ adrenergic receptor are L-$\alpha$-1a, expressing a human $\alpha$1a adrenergic receptor, L-$\alpha$1b expressing a human $\alpha$1b adrenergic receptor, and L-$\alpha$1c expressing a human $\alpha$1c adrenergic receptor. These cells are suitable for studying the pharmacological properties of the human $\alpha$1 adrenergic receptor and for the screening of ligands and drugs that specifically bind to human $\alpha$1 adrenergic receptor subtypes.

The invention will be better understood by reference to the Experimental Details which follow, but those skilled in the art will readily appreciate that the specific experiments detailed are only illustrative, and are not meant to limit the invention as described herein, which is defined by the claims which follow thereafter.

MATERIALS AND METHODS

Cloning and Sequencing $\alpha$1a: A human lymphocyte genomic library in $\xi$ dash II ($\approx$1.5$\times$10$^6$ total recombinants; Stratagene, LaJolla, Calif.) was screened using a cloned rat PCR fragment (RBNC2) as a probe. RBNC2 was obtained by amplifying randomly primed rat brain cDNA with degenerate primers designed to conserved regions of transmembrane (Tm) regions 2 and 6 of serotonin receptors. The sequence of one PCR product, RBNC2, exhibited strong homology to the $\alpha$1 AR family.

The probe was labeled with [$^{32}$ P] by the method of random priming (5) (Prime-It Random Primer kit, Strategene, LaJolla, Calif.). Hybridization was performed at 40° C. in a solution containing 50% formamide, 10% dextran sulfate, 5$\times$ SSC (1$\times$ SSC is 0.15M sodium choloride, 0.015M sodium citrate), 1$\times$ Denhardt's solution (0.02% polyvinylpyrrolidone, 0.02% Ficoll, 0.02% bovine serum albumin), and 200 $\mu$g/$\mu$l sonicated salmon sperm DNA. The filters were washed at 50° C. in 0.1$\times$ SSC containing 0.5% sodium dodecyl sulfate and exposed at –70° C. to Kodak XAR film in the presence of an intensifying screen. Lambda phage clones hybridizing with the probe were plaque purified and DNA was prepared for Southern blot analysis (22, 17). For subcloning and further Southern blot analysis, DNA was cloned into pUC18 (Pharmacia, Piscataway, N.J.) or pBluescript (Stratagene, LaJolla, Calif.). Nucleotide sequence analysis was accomplished by the Sanger dideoxy nucleotide chain termination method (18) on denatured double-stranded plasmid templates, using Sequenase (US Biochemcial Corp., Cleveland, Ohio), Bst DNA sequencing kit (Bio-Rad Laboratories, Richmond, Calif.), or TaqTrack sequencing kit (Promega Corporation, Madison, Wis.).

In order to isolate a full-length clone, human cDNA libraries were screened by polymerase chain reaction (PCR) with 1 $\mu$M each of specific oligonucleotide primers designed off the isolated genomic clone: from the sense strand (nucleotide 598–626), 5' CACTCAAGTACCCAGCCAT-CATGAC 3' (SEQ ID NO. 7) and from the antisense stand (nucleotide 979–1003), 5' CGGAGAGCGAGCTGCG-GAAGGTGTG 3' (SEQ ID NO. 8) (see FIGS. 1A01I). The primers were from non-conserved portions of the receptor gene, specifically in the Tm3-Tm3 loop and in the Tm5–Tm6 loop regions for the upstream and downstream primers, respectively. One to 2 $\mu$l of phage DNA from cDNA libraries ($\xi$ ZapII; Stratagene, LaJolla, Calif.), representing $\approx$10$^6$–10$^7$ pfu, were amplified in 10 mM Tris-HCl, pH 8.3, 50 mM KCl, 1.5 mM MgCl$_2$, 0.01% gelatin, 200 $\mu$M each dATP, dCTP, dTTP, 2.5 units of Thermus aquaticus DNA polymerase (Taq polymerase; Perkin-Elmer-Cetus, Norwalk, Conn.). The amplification profile was run for 30 cycles: a 5 min. initial (i.e. 1 cycle denaturation at 95° C., followed by 2 min. at 94° C., 2 min at 68° C., and 3 min at 72° C., with a 3 sec. extension, followed by a final 10 min. extension at 72° C. PCR products were analyzed by ethidium bromide (EtBr) stained agarose gels and any sample exhibiting a band on the EtBr stained gel was considered positive.

A positive library was then plated and screened with overlapping 45-mer oligonucleotide probes, filled-in using [$\alpha$-$^{32}$P]dCTP and [$\alpha$-$^{32}$P]dATP and Klenow fragment of DNA polymerase. This probe was internal to the amplification primers discussed above from the sense strand (nucleotide 890–934), 5' GCAAGGCCTCCGAGGTGGT-GCTGCGCATCCACTGTCGCGGCGCGG 3' (SEQ ID NO. 9), and from the anti-sense strand (nucleotide 915–961), 5' TGCCGTGCGCCCCGTCGGCGCCCGTG-GCCGCGCCGCGACAGTGGATG 3' (SEQ ID NO. 10) (see FIGS. 1A–1I). Positive cDNA phage clones were plaque certified and pBluescript recombinant DNAs were excision-rescued from $\xi$ Zap II using helper phage R408, as described by manufacturer's protocol (Stratagene, LaJolla, Calif.). Insert size was confirmed by restriction enzyme digest analysis and recombinants were sequences as described above.

$\alpha$1b: A human placenta genomic library in $\lambda$ dash II ($\approx$1.5$\times$10$^6$ total recombinants; Stratagene, LaJolla, Calif.) was screened using overlapping 45-mer oligonucleotides radiolabeled as described above and directed to the third, fifth and sixth transmembrane regions of serotonin 5HT1D$\beta$ receptor gene. Hybridization and washing conditions were identical, to that described for cla above except lower stringency hybridization nd washes were conducted; specifically, hybridization in 25% formamide and washes at 40° C.

Positive-hybridizing $\lambda$ phage clones were plaque-purified, analyzed by Southern blot analysis, subcloned and sequenced, as described above for $\alpha$1a. In order to isolate full-length clones, human cDNA libraries in $\lambda$ Zap II (Strategene, LaJolla, Calif.) were screened by polymerase chain reaction as described above. The upstream and downstream PCR primers used were from the Tm40Tm5 loop and the Tm5–Tm6 loop, respectively: from the sense strand (nucleotide 567–593), 5' CAACGATGACAAGGA GTGCGGGGTCAC 3' (SEQ ID NO. 11), and from the antisense strand (nucleotide 822–847), 5' TTTGACAGC- TATGGAACTCCTGGGG 3' (SEQ ID NO. 12) (see FIG. 2). PCR, library screen, plaque purification excision-rescue from λ Zap II, restriction digestions and sequencing were accomplished as described above for α1a. The internal probe was: from the sense strand (nucleotide 745–789), 5' AAGGAGCTGACCCTGAGGATCCATTC-CAAGAACTTTC ACGAGGAC 3' (SEQ ID NO. 13), and from the anti-sense strand (nucleotide 770–814), 5' CCT-TGGCCTTGGTACTGCTAAGGGTGTCCTCGTGAAA GTTCTTGG 3' (SEQ ID NO. 14) (see FIGS. 2A–2H).

α1c: A human lymphocyte genomic library in λ dash II ($\approx 1.5 \times 10^6$ total recombinants; Stratagene, LaJolla, Calif.) was screened using overlapping 45-mer oligonucleotides radiolabeled as described for α1a and directed to the third, fifth and sixth transmembrane regions of serotonin 5HT1A receptor gene. Hybridization and washing conditions were identical to that described for α1b. Positive-hybridizing λ phage clones were plaque-purified, analyzed by. Southern blot analysis, subcloned and sequenced, as described above for α1a. Identification and isolation of full=length clones by PCR and screening cDNA libraries were accomplished as described for α1b. The upstream and downstream PCR primers used were from the Tm3–Tm4 loop and the Tm5–Tm6 loop, respectively: from the sense strand (nucleotide 403–425), 5' CCAACCATCGTCACCCAGAG-GAG 3' (SEQ ID NO. 15), and from the antisense strand (nucleotide 775–802), 5' TCTCCCGGG AGAACTTGAG-GAGCCTCAC 3' (SEQ ID NO. 16) (see FIGS. 3A–3G). The internal probe was: from the sense strand (nucleotide 711–745), 5' TCCGCATCCATCGGAAAAACGCCCCG-GCAGGAGGC AGCGGGATGG 3' (SEQ ID NO. 17), and from the anti-sense strand (nucleotide 726–771), 5' GAAGTGCGTCTTGGTCTTGGCGCT GGCCATC-CCGCTGCCTCCTGCC 3' (SEQ ID NO. 18) (see FIGS. 3A–3G). PCR, library screen, plaque purification excision-rescue from λ Zap II, restriction digestions and sequencing were accomplished as described above for α1a.

Expression

α1a: The entire coding region of α1a (1719 bp), including 150 basepairs of 5' untranslated sequence (5' UT) and 300 bp of 3' untranslated sequence (3' UT), was cloned into the BamHI and ClaI sites of the polylinker-modified eukaryotic expression vector pCEXV-3 (13), called EXJ.HR (unpublished data). The construct involved the ligation of partial overlapping human lymphocyte genomic and hippoc-ampp$\alpha_1$ cDNA clones: 5' sequences were contained on a 1.2 kb SmaI-XhoI genomic fragment (the vector-derived BamHI site was used for subcloning instead of the internal insert-derived SmaI site) and 3' sequences were contained on an 1.3 kb XhoI-ClaI cDNA fragment (the ClaI site was from the vector polylinker). Stable cell lines were obtained by cotransfection with the plasmid α1a/EXJ (expression vector containing the α1a receptor gene) and the plasmid pGCcos3neo (plasmid containing the aminoglycoside transferase gene) into IM(tk−), CHO, NIH3T3 cells, and 293 cells using calcium phosphate technique. The cells were grown, in a controlled environment (37° C., 5% $CO_2$), as monolayers in Dulbecco's modified Eagle's Medium (GIBCO, Grand Island, N.Y.) containing 25 mM glucose and supplemented with 10% bovine calf serum, 100 units/ml penicillin G, and 100 μg/ml streptomycin sulfate. Stable clones were then selected for resistance to the antibiotic G-418 (1 mg/ml) as described previously (26) and membranes were harvested and assayed for their ability to bind [$^3$H]prazosin as described below (see "Radioligand Binding Assays").

α1b: The entire coding region of α1b (1563 bp), including 200 basepairs of 5' untranslated sequence (5' UT) and 600 bp of 3' untranslated sequence (3' UT), was cloned into the EcoRI site of pCEXV-3 eukaryotic expression vector (13). The construct involved ligating the full-length containing EcoRI brainstem cDNA fragment from λ Zap II into the expression vector. Stable cell lines were selected as described above.

α1c: The entire coding region of α1c (1401 bp), including 400 basepairs of 5' untranslated sequence (5' UT) and 200 bp of 3' untranslated sequence (3' UT), was cloned into the KpnI site of the polylinker-modified pCEXV-3-derived (13) eukaryotic expression vector, EXJ.RH (unpublished data). The construct involved ligating three partial overlapping fragments: a 5' 0.6 kb HincII genomic clone, a central 1.8 EcoRI hippocamppal cDNA clone, and a 3' 0.6 kb PstI genomic clone. The hippocamppal cDNA fragment overlaps with the 5' and 3' genomic clones so that the HincII and PstI sites at the 5' and 3' ends of the cDNA clones, respectively, were utilized for ligation. This full-length clone was cloned into the KpnI sites of the fragment, derived from vector (ie pBluescript) and 3' untranslated sequences, respectively. Stable cell lines were selected as described above.

Radioligand Binding Assays

Transfected cells from culture flasks were scraped into 5 ml of 5 mM tris-HCl, 5 mM EDTA, pH 7.5, and lysed by sonication. The cell lysates were centrifuged at 1000 rpm for 5 min at 4° C. The pellet was suspended in 50 mM Tris-HCl, 1 mM $MgCl_2$, and 0.1% ascorbic acid at pH 7.5. Binding of the α1 antagonist [$^3$H]prazosin (0.5 nM, specific activity 76.2 Ci/mmol) to membrane preparations of LM(tk−) cells was done in a final volume of 0.25 ml and incubated at 37° C. for 20 min. Nonspecific binding was determined in the presence of 10 μM phentolamine. The reaction was stopped by filtration through GF/B filters using a cell harvester. Data were analyzed by a computerized non-linear regression program.

Measurement of [$^3$H]Inositol Phosphates (IP) Formation

Cells were suspended in Dulbecco's phosphate buffered saline (PBS), and incubated with 5 μCi/ml [$^3$H]m-inositol for 60 min at 37° C., the reaction was stopped by adding $CHCl_3$:Methanol: HCl (2/1/0.01 v/v). Total [$^3$H]IP were separated by ion exchange chromatography and quantified as described by Forray and El-Fakahany (7).

Calcium Measurements

Intracellular calcium levels ([$Ca^{2+}$]i) were determined with the calcium-sensitive dye fura-2, and microspectrofluorometry, essentially as previously described (1,3). Briefly, cells were plated into polylysine-coated coverslip bottom dishes (MatTek Corporation, Ashland Mass.). To lead with fura-2, cells were washed 3× with HEPES-buffered saline (HBS, in mM: HEPES, 20; NaCl, 150; KCl, 5; $CaCl_2$, 1; $MgCl_2$, 1; glucose, 10; pH 7.4) and incubated for 30 minutes at room temperature with fura-2 loading solution (5 uM fura-2/AM, 0.03% pluronic F-127, and 2% heat-inactivated fetal calf serum, in HBS). After loading, cells were washed 3× with HBS, 1 ml of HBS was added, and the dish was placed on the microscope for determination of [$Ca^{2+}$]$_i$. [$Ca^{2+}$]$_i$ was measured with a Leitz Fluovert microscope equipped for UV-transmission epifluorescence. Fura-2 fluorescence was alternately excited at 340 and 380 nm (0.25 sec), and a pair of readings (500 nm long pass) was taken every two seconds, and recorded by a personal computer interfaced to a data acquisition and control unit from Kinetek (Yonkers, N.Y.). To determine [$Ca^{2+}$]$_i$ from the experimental data the background fluorescence was subtracted, and the corrected ratios were converted to [$Ca^{2+}$]$_i$ by comparison with buffers containing saturating and low free calcium, assuming a $K_D$ of 400 nM (3).

Results

α1a: We screened a human genomic lymphocyte library with a rat PCR fragment that exhibited homology with the α1-AR family. A total of six clones were isolated and characterized by Southern blot analysis. One clone, h13, contained a 4.0 kb XbaI fragment which hybridized with the radiolabeled rat PCR fragment and was subsequently subcloned into pUC vector. DNA sequence analysis indicated greatest homology to human α1a and rat α1a ARs. This clone contained the initiating methionine through Tm6 with ≈1.0–1.5 kb 5' UT region. Subsequent Southern blot, analysis, subcloning and sequencing analysis indicated the presence of a SmaI site ≈150 nts. 5' to the initiating methionine codon. The homology between h13 and rat α1a adrenergic gene breaks just downstream of Tm6, indicating an intron which is located in an analogous region in the α1b- and α1c-AR genes (4,20). In order to obtain a full-length clone, aliquots of human cDNA libraries totaling ≈1.5×10$^6$ recombinants was screened by polymerase chain reaction using specific oligonucleotide primers from sequence determined off the genomic clone (see Materials and Methods). A positive-containing human hippocamppal cDNA library (Stratagene, LaJolla, Calif.) in λ Zap II (≈1.5×10$^6$ recombinants) was screened using traditional plaque hybridization with an internal probe (see Materials and Methods) and resulted in the isolation of two positive cDNA clones, one containing the upstream sequences (from 5' UT through the 5–6 loop; hH22) and the other containing downstream sequences (from within Tm5 through ≈200 nts. with a common XhoI site being present within this common region.

The complete full-length gene was constructed by splicing together two restriction fragments, one being the 3' cDNA (hH14) and the other being the 5' genomic clone (h13), using a unique restriction site (XhoI) present in the overlapping region. In addition, another construct was accomplished by ligating the two cDNA clones (hH14 and hH22), using the overlapping XhoI site; however, since this construct produced the same pharmacology as the genomic/cDNA construct, we will not discuss this recombinant (unpublished observation). The genomic/cDNA construct contains an open reading frame of 1719 bp and encoding a protein of 572 aa in length, having a relative molecular mass of ≈63,000 daltons. Hydropathy analysis of the protein is consistent with a putative topography of seven transmembrane domains, indicative of the G protein-coupled receptor family. Initial sequence analysis revealed that clone α1a/EXJ was most related to an AR since it contained a number of conserved structural features/residues found among the members of the adrenergic receptor family, including conserve cysteines in the second and third extracellular loops, a conserved glycine residue in Tm1, aspartic acid residues in Tm regions II and III, conserved valine residues in TmIII, the DRY sequence at the end of TmIII, the conserved proline residues of Tm regions II, IV, V, VI and VII, and the consensus D-V-L-X-X-T-X-S-I-X-X-L-C IN Tm3 and the consensus G-Y-X-N-S-X-X-N-P-X-I-Y in the Tm VII, both consensus unique to the adrenergic receptor family (2,26). Other features of this human α1a receptor gene are the presence of two potential sites for N-linked glycosylation in the amino terminus (asparagine residues 65 and 82; FIGS. 1a–1I) and the presence of several serines and threonines in the carboxyl terminus and intracellular loops, which may serve as sites for potential phosphorylation by protein kinases.

α$_{1b}$: We screened a human genomic placenta library with probes derived from Tm3, 5 and 6 regions of serotonin 5HT1D$_B$ under low stringency. Out of several hundred positive clones pursued by Southern blot analysis, subcloning and sequencing, one resembled the α$_1$ adrenergic family of receptors. This genomic fragment contained Tm3 through Tm6 of a receptor which was most closely related to rat and hamster α$_{1b}$ receptors. In order to obtain a full-length clone, several human cDNA libraries were screened by PCR using primers derived from the 5–6 loop region of the genomic clone (see Materials and Methods). A positive-containing human brainstem cDNA library (Stratagene, LaJolla, Calif.) in λ ZAPII (≈2×10$^6$ recombinants) was screened using traditional plaque hybridization with an internal probe, resulting in the isolation of two identical cDNA clones, containing an insert size of 2.4 kb. Upon sequencing, this clone was found to contain the initiating MET aa, Tm1 through Tm7, and 5' and 3' UT sequences, suggesting a full-length clone on a single EcoRI fragment. This cDNA clone contains an open reading frame of 1563 bp and encodes a protein of 520 aa in length, having a relative molecular mass of ≈57,000 daltons. Hydropathy analysis of the protein is consistent with a putative topography of seven transmembrane domains, indicative of the G protein-coupled receptor family.

Sequence analysis revealed that clone α$_{1b}$/pCEXV was most related to adrenergic receptor since it contained a number of conserved structural features found among the adrenergic receptor family, as described for α$_{1a}$ receptor (see above). This human α$_{1b}$ receptor contains potential sites for N-linked glycosylation in the amino terminus (asparagine residues 10, 24, 29, 34 in FIGS. 2A–2H), consistent with the finding that the α$_1$ AR is glycosylated (4,19).

α$_{1c}$: We screened a human genomic lymphocyte library with probes derived from the third, fifth and sixth transmembrane regions of serotonin 5HT1A under low stringency. Out of several hundred positive clones analyzed by Southern blot analysis, subcloning and sequencing (see Materials and Methods), one phage clone resembled a novel α$_1$ AR. This genomic fragment contained Tm1 through Tm6 of a receptor with high homology to the bovine α$_{1c}$ receptor and thus suggesting the presence of an intron downstream of Tm6, as shown for the α$_1$ receptor family (4,12,20). In order to obtain a full-length clone, several human cDNA libraries were screened by PCR, as described for α$_{1b}$ (also see Materials and Methods). A positive-containing human hippocamppal cDNA library (Stratagene, LaJolla, Calif.) in λ ZAPII (≈2×10$^6$ recombinants) was screened, as described for α$_{1b}$. A positive clone (hH 20) was identified which contained a 1.7 kb EcoRI cDNA fragment insert. However, this cDNA clone lacked both the amino end of the receptor (the 5' end of the clone terminated at the 5' end of Tm2) and part of the carboxyl tail (the 3' end of the clone corresponded to 40 aa upstream from the "putative" stop codon). Since an alternative genomic subclone which contained the initiating MET codon in addition to Tm1 through Tm6 was available, we needed to obtain the complete 3' carboxyl tail in order to complete the construct of the full-length clone. This was accomplished by using overlapping 45-mer oligonucleotide primers (corresponding to nts. 1142–1212 in FIG. 3), designed within the carboxyl tail of the receptor (at the 3' end of the hH20 cDNA clone), to screen a human lymphocyte genomic library in order to isolate a genomic clone containing the carboxyl tail that includes the termination codon. Two identical positive human lymphocyte genomic clones were isolated from this library. A 0.6 kb PstI fragment was subcloned and shown to contain most of the carboxyl tail (≈20 aa downstream of Tm7) through the termination codon and ≈200 bp of 3' UT sequence.

The complete full-length gene was constructed by splicing together three restriction fragments: A 0.6 kb HincII fragment from the genomic clone, containing ≈0.4 kb of 5' UT sequence and the initiating MET codon through Tm2; the 0.8 kb HincII-PstI fragment from the hH cDNA clone, which contains Tm2 through part of the carboxyl tail, overlapping with the 5' genomic clone by 20 nts. (sharing the unique HincII site at position 196 in FIG. 3); and a 0.6 kb PstI fragment from the second hl genomic clone, which contains the carboxyl tail, the stop codon and ≈0.2 kb of 3' UT sequence, and overlapping with the hH cDNA clone (sharing the unique Pst I site within the carboxyl tail at position 1038 in FIGS. 3A–3G).

The resulting genomic/cDNA/genomic construct contains an open reading frame of 1401 bp and encoding a protein of 466 aa in length, having a molecular weight of ≈51,000 daltons. Hydropathy analysis of the protein is consistent with a putative topography of seven transmembrane domains, as indicated for the previously described human $\alpha_{1a}$ and $\alpha_{1b}$ receptors and indicative of the G protein-coupled receptor family. Sequence analysis revealed that clone $\alpha_{1c}$/EXJ was most related to adrenergic receptor because it contained the structural features commonly found among the adrenergic receptor family of receptors, as described for the $\alpha_{1a}$ receptor above. Other features of this human $\alpha_{1c}$ receptor gene is the presence of three potential sites for N-linked glycosylation in the amino terminus, at the same position described for the bovine $\alpha_{1c}$ receptor (asparagine residues 7, 13 and 22 in FIGS. 3A–3G) (20). Several threonines and serines exist in the second and third cytoplasmic loops of this $\alpha_{1c}$ receptor, which may serve as potential sites for protein kinases and phosphorylation.

TABLE 1

Competition of adrenergic agonists and antagonists for the binding of [$^3$H]prazosin to membranes prepared from LM(tk$^-$) cells expressing the human $\alpha_{1a}$, $\alpha_{1b}$, and $\alpha_{1c}$-adrenergic receptor cDNA. Membrane preparations from stably transfected cell lines increasing concentrations of various agonists or antagonists as described under "Materials and Methods". Data is shown as the mean ± S.E.M. of the binding parameters estimated by a computerized non-linear regression analysis obtained in three independent experiments each performed in triplicate.

| | pKi | | |
|---|---|---|---|
| | $\alpha_{1a}$ | $\alpha_{1b}$ | $\alpha_{1c}$ |
| AGONISTS | | | |
| Norepinephrine | 6.633 ± 0.12 | 5.614 ± 0.09 | 5.747 ± 0.18 |
| Epinephrine | 6.245 ± 0.10 | 5.297 ± 0.15 | 5.511 ± 0.13 |
| Oxymetazoline | 5.903 ± 0.16 | 5.919 ± 0.07 | 7.691 ± 0.10 |
| Naphazoline | 6.647 ± 0.18 | 6.155 ± 0.04 | 6.705 ± 0.22 |
| Xylometazoline | 5.913 ± 0.20 | 6.096 ± 0.30 | 7.499 ± 0.19 |
| ANTAGONISTS | | | |
| Prazosin | 9.479 ± 0.19 | 9.260 ± 0.23 | 9.234 ± 0.13 |
| WB-4101 | 8.828 ± 0.12 | 7.909 ± 0.13 | 9.080 ± 0.09 |
| (+) Niguldipine | 6.643 ± 0.10 | 6.937 ± 0.12 | 8.693 ± 0.18 |
| Indoramin | 6.629 ± 0.09 | 7.347 ± 0.17 | 8.341 ± 0.25 |
| 5-Methyl Urapidil | 7.795 ± 0.15 | 6.603 ± 0.09 | 8.160 ± 0.11 |
| HEAT | 7.857 ± 0.13 | 8.474 ± 0.10 | 8.617 ± 0.10 |
| Urapidil | 6.509 ± 0.18 | 5.932 ± 0.11 | 6.987 ± 0.14 |
| Rauwolscine | 5.274 ± 0.12 | 4.852 ± 0.08 | 4.527 ± 0.11 |

Pharmacological Analysis:

To further assess the functional identity of the cloned cDNA the coding regions were subcloned into the pCEXV-3 expression vector, and LM(tk−) cell lines stably expressing the human cDNA encoding each of the three $\alpha_1$-ARs were established. Membrane preparations of these cell lines showed high affinity binding of [$^3$H]prazosin, with Kd values of 0.21±0.03 nM (Bmax=0.72±0.04 pmol/mg prot), 0.88±0.1 nM (Bmax=4.59±0.21 pmol/mg prot) and 0.39±0.08 nM (Bmax=1.9±0.04 pmol/mg prot) for the cells expressing the $\alpha_{1a}$, $\alpha_{1b}$, and $\alpha_{1c}$-ARts respectively. In contrast in competition binding experiments rauwolscine showed extremely low affinity at the three cloned receptors (Table 1), consistent with their identity as $\alpha_1$-AR. The α-adrenergic agonists NE and epinephrine were found to be 6 and 5-fold respectively, more potent at the human $\alpha_{1a}$-AR, conversely the imidazoline derivatives such as oxymetazoline and xylometazoline showed 52-fold higher potency at the $\alpha_{1c}$-AR. Similarly, several antagonists showed marked differences in their potency to inhibit [$^3$H]prazosin binding from the cloned human $\alpha_1$ receptors subtypes. The selective antagonists WB-4101 and 5-methyl-urapidil showed high affinity for the human $\alpha_{1c}$ subtype (0.8 and 7 nM respectively), followed by less than 2-fold lower potency at the human $\alpha_{1a}$ and at least an order of magnitude (15 and 36-fold respectively) lower potency at the human $\alpha_{1b}$-AR. Similarly, indoramin was 50 and 10-fold more potent at the $\alpha_{1c}$ than at the $\alpha_{1a}$ and $\alpha_{1b}$ respectively. The calcium channel blocker (+)-niguldipine showed the highest selectivity for the three $\alpha_1$-AR subtypes, displacing [$^3$H]prazosin 112 and 57-fold more potently from the $\alpha_{1c}$ than from $\alpha_{1a}$ and $\alpha_{1b}$ transfected cells respectively.

TABLE 2

Receptor-mediated formation of [$^3$H]IP in cell lines transfected with the human $\alpha_1$-adrenergic receptors cDNA.
Cell lines stably expressing the human $\alpha_1$-adrenergic receptors were obtained and the IP formation was measured in the absence or presence of 10 μM norepinephrine (NE) in the presence of 10 mM LiCl as described under "Material and Methods". Data are shown as mean ± S.E.M. of three independent experiments performed in triplicate.

| Cell Line | [$^3$H]IP dpm/dish | Fold Stimulation | Receptor[a] Density pmol/mg Prot |
|---|---|---|---|
| 293 $\alpha_{1a}$ | | | 3.30 |
| Control | 288 ± 29 | | |
| NE | 3646 ± 144 | 13 | |
| CHO $\alpha_{1b}$ | | | 0.49 |
| Control | 1069 ± 26 | | |
| NE | 5934 ± 309 | 6 | |
| NIH3T3 $\alpha_{1c}$ | | | 0.24 |
| Control | 722 ± 61 | | |
| NE | 13929 ± 1226 | 19 | |

[a] Determined by [$^3$H]Prazosin binding.

The formation of [$^3$H]IP was measured in 293, CHO, and NIH3T3 cell stably expressing the cloned human $\alpha_{1a}$, $\alpha_{1b}$, $\alpha_{1c}$-ARs respectively, to assess the functional coupling of these receptors with the activation of phosphatidyl-inositol specific phospholipase C (PI-PLC). As shown in Table 2, the adrenergic agonist NE (10 μM) activated the formation of IP by 13-fold in cells expressing the $\alpha_{1a}$ receptor, and by 5 and 15-fold in cells expressing the $\alpha_{1a}$, $\alpha_{1b}$ and $\alpha_{1c}$ receptors respectively. Furthermore, when cells expressing $\alpha_{1b}$ and $\alpha_{1c}$ receptors were incubated in the presence of 10 μM NE, a rapid increase of cytosolic calcium was observed. The response was characterized by an early peak, followed by a plateau that slowly declined towards resting calcium levels (FIG. 7). The concentration of [Ca$^{2+}$]$_i$, was increased by 172±33 (n=6), 170±48 (n=6) and 224±79 nM (n=6) in cell lines transfected with the $\alpha_{1a}$, $\alpha_{1b}$ and $\alpha_{1a}$ receptors respectively. The changes in [Ca$^{2+}$]$_i$ induced by NE were suppressed by preincubation of the cells with 10 nM prazosin, indicating that the calcium response was mediated by $\alpha_1$-ARs.

We have cloned DNA representing three $\alpha_1$-ARs subtypes ($\alpha_{1a}$, $\alpha_{1b}$ and $\alpha_{1c}$) from human brain cDNA and genomic DNA. Of all known G protein-coupled receptor sequences (EMBL/Genbank Data Base), the greatest homology was found between $\alpha_{1a}$/EXJ and the rat $\alpha_{1a}$ AR (12), rat $\alpha_{1d}$ AR (16) and a previously reported putative human "$\alpha_{1a}$" adrenergic receptor (H318/3) (2). Comparison of the human $\alpha_{1a}$ deduced aa sequence with known $\alpha_{1a}$ ARs indicates the greatest concentration of identical aa to be in the transmembrane domains. In these Tm regions, the percentage of identity for the human $\alpha_{1a}$ AR is 98% compared to rat $\alpha_{1a}$ AR (12) (this is approximately the same for rat $\alpha_{1d}$ since rat $\alpha_{1d}$ AR is the same as rat $\alpha_{1a}$ AR, except for two amino acid differences), 100% with the previously reported H318/3, 78% with the human $\alpha_{1b}$ receptor (see below), and 69% with the human $\alpha_{1c}$ receptor (see below), which is typical among subtypes. When considering the full-length proteins, the percent identity drops and is only 50% for the human $\alpha_{1b}$ and 49% for the human $\alpha_{1c}$ receptor. Both the alignment (see FIG. 4) and percent identity of this human $\alpha_{1a}$ sequence, relative to other members of the AR family strongly suggest that this is a new receptor and is the human species homolog of the rat $\alpha_{1a}$ receptor.

FIG. 4 shows a comparison between the deduced aa sequence of $\alpha_{1a}$/EXJ and the sequences of rat $\alpha_{1a}$ and HAR. An overall homology of 83.5% aa identity with at $\alpha_{1a}$ and 86.5% aa identity with the previously published H318/3 clone was observed, suggesting that our human $\alpha_{1a}$ receptor is not any more related to the previously published putative human "$\alpha_{1a}$" than it is to the rat $\alpha_{1a}$ receptor. In fact, in support of this conclusion, is the fact that the overall aa homology of rat $\alpha_{1a}$ receptor with our human $\alpha_{1a}$ receptor is 83.5% but is only 72% compared to the H318/3 receptor. The main differences between our human $\alpha_{1a}$ receptor and the previously reported "$\alpha_{1a}$" receptor in relation to the rat $\alpha_{1a}$ are indicated in FIG. 4. Most notably are the differences observed at both the amino and carboxyl ends of the receptor. Specifically, both our human $\alpha_{1a}$ and rat $\alpha_{1a}$ use the starting MET aa at position 1 (see FIG. 4) whereas the previously published H318/3 uses the starting MET 48 aa downstream. Also, the amino terminus of the H318/3 clone is completely divergent from either rat $\alpha_{1a}$ or our human $\alpha_{1a}$ receptor until about 12 aa upstream of Tm1 where significant homology begins. Similarly, in the carboxyl tail, the homology of H318/3 diverges ≈90 aa upstream from the stop codon of either rat or our human $\alpha_{1a}$ receptor and instead, uses a stop codon 30 aa upstream from the stop codon on either of these receptors. Finally, the H318/3 clone has an amino terminal extracellular region that does not contain potential sites for N-linked glycosylation (2), in contrast to the rat $\alpha_{1a}$ or our human $\alpha_{1a}$ receptor, which contains two potential sites (12, see also FIG. 1 and above). Thus, these data strongly suggest that our human $\alpha_{1a}$ receptor is different in sequence from the previously reported putative human "$\alpha_{1a}$" (H318/3) but is more related to the previously published rat $\alpha_{1a}$ receptor. Interestingly, the rat $\alpha_{1a}$ aa sequence diverges from both human $\alpha_{1a}$ receptors for ≈65 aa in the carboxyl tail (position 434–508 in FIG. 1); however, homology is seen again in our human $\alpha_{1a}$ receptor but not with H318/3, downstream from this region.

The cloning of different $\alpha_1$ receptor subtypes permits analysis of both the pharmacological and functional properties of adrenergic receptors. The human $\alpha_{1b}$/pcEXV clone exhibited the greatest homology with the rat and hamster $\alpha_{1b}$ receptors, out of all known G protein-coupled receptor clones (EMBL/Genbank Data Bank). Comparison of the human $\alpha_{1b}$ deduced aa sequence with known $\alpha_1$ ARs indicates the greatest homology in the transmembrane regions. In these Tm regions, the percent identity for the human $\alpha_{1b}$ AR is 99% compared to either rat (25) or hamster (4)$\alpha_{1b}$ receptor, 78% with human $\alpha_{1a}$ receptor and 75% with human $\alpha_{1c}$ receptor, which is typical among subtypes. When analyzing the full-length proteins, the percent identity slightly drops and is 94.5% compared to rat $\alpha_{1b}$, 95.5% compared to hamster $\alpha_{1b}$ receptor, 50% compared to human $\alpha_{1a}$ and 51% compared to human $\alpha_{1c}$ receptor. Both the alignment (see FIG. 5) and percent identity of this human $\alpha_{1b}$ sequence, relative to other members of the AR family, strongly suggest that this clone represents a new receptor and is the human species homologue of the rat/hamster $\alpha_{1b}$ receptor. FIG. 5 shows a comparison between the deduced amino acid sequence of $\alpha_{1b}$/pcEXV and the aa sequence of rat $\alpha_{1b}$ and hamster $\alpha_{1b}$ receptors.

A third human adrenergic receptor clone, $\alpha_{1c}$/EXJ, showed the greatest homology with the bovine $\alpha_{1c}$ AR gene (20), from all known G protein-coupled receptor sequences (EMBL/Genbank Data Bank). Comparison of the human $\alpha_{1c}$ deduced aa sequence with the $\alpha_1$ ARs indicates the greatest homology to be in the transmembrane regions. In these Tm regions, the percent identity for the human $\alpha_{1c}$ AR is 97% compared to the bovine $\alpha_{1c}$ AR (20), 75% with human $\alpha_{1b}$ receptor and 69% with human $\alpha_{1a}$ receptor, which is typical among subtypes. When one examines the full-length proteins, the percent identity drops and is only 51% compared to either the human $\alpha_{1b}$ or human $\alpha_{1a}$ receptor. FIG. 6 shows a comparison between the deduced amino acid sequence of $\alpha_{1c}$/EXJ and the aa sequence of bovine $\alpha_{1c}$. An overall homology of 92% aa identity with bovine $\alpha_{1c}$ receptor was observed. Both the alignment (see FIG. 6) and percent identity of this human $\alpha_{1c}$ sequence, relative to other members of the AR family, strongly suggest that this clone represents a new receptor and is the human species homologue of the bovine a receptor.

The stable expression of the three cloned human $\alpha_1$ receptors enabled the characterization of their pharmacological as well as their functional properties and allowed identification of certain unique features of the human receptors, not predicted from previous data. The rank-order of potency of known $\alpha$-adrenergic agonists and antagonists to compete with [$^3$H]prazosin in binding assays, confirmed that the cloned cDNAs encode three human receptors of the $\alpha_1$-AR family. Moreover, the potencies of selective antagonists such as WB-4101 and 5-methyl-urapidil at the three human $\alpha_1$-receptors were found to be in close agreement with the potencies of these antagonists at the cloned rat $\alpha_{1a}$, hamster $\alpha_{1b}$, and bovine $\alpha_{1c}$ (4, 12, 20). These results suggest that the sequence homology between the three mammalian $\alpha_1$ receptors resulted in a conservation of their pharmacological properties across different species. In the past the pharmacological characterization of $\alpha_1$-adrenergic receptors took advantage of the existence of selective antagonists such as WB-4101 and 5-methyl-urapidil that bind with high affinity to a subset of $\alpha_1$-receptors classified as $\alpha_{1a}$ (9, 15). our results using these selective antagonists indicate that these antagonists bind with similar affinity to both human $\alpha_{1a}$ and $\alpha$1c-receptors, and that they can only discriminate between either of these two subtypes and the $\alpha_{1b}$ receptor. The calcium channel blocker (+)-niguldipine was found to bind with high affinity to a subset of $\alpha_1$-receptors also labeled by [$^3$H]5-methyl-urapidil in rat brain, thus defining this antagonist as $\alpha_{1a}$ selective (8). The high affinity of the human $\alpha_{1c}$ receptor for (+)-niguldipine and the fact that it binds to the human $\alpha_{1a}$ and $\alpha_{1b}$ subtypes, with at least an order of magnitude lower affinity, strongly supports the notion that the human $\alpha_{1c}$ gene encodes the pharmacological $\alpha_{1a}$-receptor subtype. The possibility that this also holds true in the rat, is suggested by the fact that the potency of (+)niguldipine for the rat $\alpha_{1a}$ clone is also at least an order of magnitude lower than that found for this antagonist in rat tissues. Moreover in spite of the earlier reports on the absence of the bovine $\alpha_{1c}$ cognate in rat tissues (20), (24,21) pharmacological evidence suggests that this species express an $\alpha_1$ receptor similar to the cloned $\alpha_{1c}$ receptor. These data altogether indicate that in trying to match the pharmacological subclassification of the $\alpha_1$-ARs with the evidence from molecular cloning studies, the initial assignment of the cloned rat $\alpha_{1a}$ receptor with the $\alpha_{1a}$ receptor subtype was inadequate. Recently, a rat cDNA clone 99.8% homologous to the rat $\alpha_{1a}$-receptor, was described as a novel $\alpha_{1d}$ subtype (16); however, this incorrect classification was due to the poor correlation between the affinities of $\alpha_{1a}$-selective antagonists in tissue preparations versus the cloned rat $\alpha_{1a}$ receptor.

The three human $\alpha_1$ receptor subtypes were able to induce the formation of IP, consistent with the known functional coupling of $\alpha_1$-ARs, through a GTP-dependent protein to the activation of PI-PLC. In addition we demonstrated that upon receptor activation by adrenergic agonists, the human $\alpha_1$ subtypes induced transient changes three in $[Ca^{2+}]_i$. Consistent with the mobilization of calcium from intracellular stores by inositol-1,3,5 triphosphate, released by the receptor-mediated activation of PI-PLC.

We have cloned and expressed three human cDNA that encode functional $\alpha_1$-ARs. These three transcripts display significant pharmacologic as well as molecular features to constitute distinct $\alpha_1$-AR subtypes. In sharp contrast with the restricted expression of the rat and bovine transcripts, our findings indicate that species homologs of the three $\alpha_1$-ARs are expressed in human tissues. These findings together with recent reports on the dissimilar tissue distribution of the $\alpha_{1b}$ and $\alpha_{1c}$ receptor cognates between animal species such as rat and rabbit (21), commonly used in the development of novel $\alpha_1$-adrenergic agents, emphasize the need to study the pharmacological properties of the human $\alpha_1$-receptors. In this regard, the results from this study on the selectivity of clinically effective antihypertensives such as indoramin, as well as vasoconstrictors such as oxymetazoline and xylometazoline for the human $\alpha_{1c}$-AR, suggest a potential role for this $\alpha_1$-receptor subtype in the physiological control of vascular tone in the human. Thus, the availability of cell lines expressing each of the human $\alpha_1$-receptor subtypes constitute a unique tool in the design of subtype specific agonists and antagonists, that can be targeted to selective therapeutic applications. Of specific interest for therapeutics are subtype selective alpha-1 antagonists for the treatment of Benign Prostatic Hypertrophy, coronary heart disease, insulin resistance, atherosclerosis, sympathetic dystrophy syndrome, glaucoma, cardiac arrythymias, erectile dysfunction, Reynaud's syndrome, hypertension and urinary retention (44, 27,31,32,33,34,35,48). Further interest exists for subtype selective alpha-1 agonists for the treatment of congestive heart failure, nasal congestion, urinary incontinence and hypotension (45,46,47,48). In each case, a more selective drug is expected to reduce the side effects which presently limit this avenue of therapy.

The following compounds were synthesized in order to evaluate their ability to act as antagonists of $\alpha_1$-receptor function in human prostrate. The synthetic methods used to synthesize are provided herein.

The following Experimental Details are set forth to aid in an understanding of the invention, and are not intended, and should not be construed, to limit in any way the invention set forth in the claims which follow thereafter.

Experimental Details

Prazosin and 5-methylurapidil were obtained from Research Biochemicals, Inc. A30360 (4-fluoro-4-(8-fluoro-1,3,4,5-tetrahydro-2H-pyrido[4,3-b]indol-2-yl) butyrophenone hydrochloride) was obtained from Aldrich Chemical Co. Other compounds were prepared according to the examples which follow.

EXAMPLE 1

Synthesis of Terazosin Hydrochloride
N-(2-Furoyl)piperazine

This compound and its preparation has been described in Great Britain Patents 1,390,014 and 1,390,015. Piperazine hexahydrate (194 g, 1 mole) was dissolved in 250 ml $H_2O$. The solution was acidified to pH 4.5 with 6 N HCl. Furoyl chloride (130.5 g, 1 mole, Aldrich) was added along with 10% NaOH solution at such a rate that the pH was maintained at 4.5. After 1 hour, the solution was made basic (pH=8.5) with NaOH solution. The reaction mixture was continuously extracted with chloroform for 36 hours. The $CHCl_3$ extract was dried over $MgSO_4$, and filtered. Distillation gave 108.2 g product (60%), b.p. 132°–138° C./0.6 mm Hg, m.p. 69°–70° C.

N-(Tetrahydro-2-furoyl)piperazine

The furoylpiperazine of Example 1 was converted to the hydrobromide salt (m.p. 173°–175° C.). This salt (39.0 g) in 250 ml methyl alcohol and 9.0 g Raney nickel was hydrogenated at 3 atm. After uptake of $H_2$ ceased, the catalyst was filtered, the solvent concentrated, and the residue crystallized from isopropyl alcohol to give 35.2 g. tetrahydrofuroylpiperazine HBr, m.p. 152°–156° C. This was suspended in 20 ml $H_2O$. Then 10.5 g 50%, NaOH solution was added slowly followed by 2.0 g solid $Na_2CO_3$. This was extracted with 4×100 ml portions of warm $CHCl_3$. The $CHCl_3$ extractions were distilled to give 22.5 g tetrahydrofurolylpiperazine, b.p. 120°–125° C./0.2 mm Hg.

2[4-(Tetrahydro-2-furoyl)piperazinyl]-4-amino-6,7-dimethoxyquinazoline hydrochloride To 7.00 g 2-chloro-4-amino-6,7-dimethoxyquinazoline (Lancaster Synthesis) in 50 ml methoxyethanol was added 10.8 g, tetrahydrofurolylpiperazine, and the mixture refluxed 3 hours. The clear solution was concentrated and an aqueous solution of potassium bicarbonate was added. The resultant solid that formed was filtered and washed with water. It was then added to methanol and the resulting suspension was acidified with a solution of hydrogen chloride in isopropyl alcohol. The resulting solution was concentrated and the residue crystallized from isopropyl alcohol giving 8.12 g. of product, m.p. 278°–279° C.

EXAMPLE 2

Preparation of Indoramin
4-Benzamido-1-[2-(3-indolyl)ethylpyridinium Bromide

A solution of 4-benzamidopyridine (1.98 g) and 3-(2-bromoethyl)indole (2.24 g) in EtOH (15 ml) was refluxed for 2 hours, and the crystallized product (3.13 g, mp 264–266° C.) was collected by filtration from the hot reaction mixture. Recyrstallization gave the hydrate.

3-[2-4-Benzamidopiperid-1-yl)ethyl]indole (Indoramin)

4-Benzamido-1-[2-(3-indolyl)ethyl]pyridinium bromide (3.0 g) in 91% EtOH (300 ml) containing $Et_3N$ (0.8 g) was hydrogenated in the presence of freshly prepared W-7 Raney Ni catalyst (ca. 3 g) at 28.12 kg/cm² and 50° for 4 hours. After filtering off the catalyst, the filtrate was evaporated and the residue was shaken with $CHCl_3$ and 2 N NaOH. The resulting insoluble material (1.61 g, mp 203–206° C.) was collected and dried. Recrystallization from EtOH gave the product (1.34 g), as colorless needles.

EXAMPLE 3

Preparation of 1-(3-banzoylpropyl)-4-benzamidopiperidine (Compound 9)

A mixture of 4-chlorobutyrophenone (447 mg, 2.45 mmol), 4-benzamidopiperidine (500 mg, 2.45 mmol) and $K_2CO_3$ (338 mg, 2.45 mmol) was heated up in boiling water bath for 1 hour. The reaction mixture was portioned between water and $CHCl_3$. The organic layer was separated and dried over $Na_2SO_4$. After filtration and removal of solvent, the residue was purified by chromatography ($SiO_2$, $MeOH:CHCl_3$, 5:95). Recrystallization from AcOEt/hexane gave a white powder (78 mg, 8.2%). mp 143–144° C.; $^1H$ NMR ($CD_3OD$, 400 MHz) δ 1.65 (dq, $J_1$=3.16 Hz, $J_2$=11.9 Hz, 2H), 1.90–2.00 (m, 4H), 2.18 (t, J=11.9 Hz, 2H), 2.48 (m, 2H), 3.00–3.10 (m, 4H), 3.88 (m, 1H), 7.40–8.00 (m, 10H); Mass spectrum $(M+1)^+$ at m/z 351.

EXAMPLE 4

Preparation of 1-[3-(4-chlorobenzoyl)propyl]-4-benzamidopiperidine (Compound 7)

A mixture of 3-(4-chlorobenzol)propyl bromide (640 mg, 2.45 mmol), 4-benzamidopiperidine (500 mg, 2.45 mmol) and $K_2CO_3$ (1.01 g, 7.34 mmol) in 50 ml of acetone was heated up to refluxing condition for 48 hours. The solid was removed by filtration. Concentration of filtrate in vacuo gave a yellowish solid, which was purified by chromatography ($SiO_2$, $MeOH:CHCl_3$, 5:95). 320 mg (33.9%) of white powder was obtained $^1H$ NMR ($CDCl_3$, 300 mHz) δ 1.46 (dq, $J_1$=1.0 Hz, $J_2$=8.4 Hz, 2H), 1.90–2.10 (m, 4H), 2.16 (m, 2H), 2.43 (t, J=6.9 Hz, 2H), 2.80–2.90 (m, 2H), 2.97 (t, J=6.9 Hz, 2H), 3.97 (m, 1H), 5.92 (d, J=7.8 Hz, 1H, N-H), 7.40–8.00 (m, 9H); Product was converted to HCl salt and recrystallized with $MeOH/Et_2O$, mp 243–244° C.; Calcd for $C_{22}H_{25}ClN_2O_2 \cdot HCl \cdot H_2O$: C 60.15, H 6.37, N 6.37; Found: C 60.18, H 6.34, N6.29.

EXAMPLE 5

Preparation of SKF-104856
1-[(4-Chlorophenyl)thio)-2-propanone

Chloroacetone (32.3 g, 0.347 mol) was added to a mixture of 4-chlorothiophenol (50 g, 0.347 mmol) and sodium hydroxide (14 g, 0.347 mol) in water (400 ml) and the mixture was stirred at 25° C. for 1 hour. The mixture was extracted with ethyl ether and the organic phase was washed with water, dried with magnesium sulfate and concentrated to give 69 g (99%) of 1-[(4-chlorophenyl)thio]-2-propanone.

5-Chloro-3-methylbenzo(b)thiophene

1-[(4-Cholorophenyl)thio)-2-propanone (50 g, 0.25 mol) was added to polyphosphoric acid (300 g) and the mixture was stirred as the temperature was gradually raised to 120° C. as an exotherm started. The mixture was stirred at 130° C. for 1 hour, diluted with water, extracted with ethyl ether and the organic phase was dried and concentrated. The residue was stirred in methanol (200 ml), filtered and the filtrate concentrated to give 17.5 g (40%) of 5-chloro-3-methylbenzo(b)thiophene: bp 120° C. (0.6 mm Hg).

Ethyl5-chloro-3-methylbenzo(b)thiophene-2-carboxylate n-Butyllithium in hexane (2.6 M, 2.3 ml) was added to a solution of 5-chloro-3-methylbenzo(b)thiophene (1,0 g, 6 mmol) in ethyl ether (20 ml) stirred at 0° C. under argon. The mixture was stirred for 30 minutes and transferred slowly under argon pressure to a stirred solution of ethyl chloroformate (0.63 g, 6 mmol) in ethyl ether (20 ml). The mixture was stirred at 0° C. for 30 minutes and at 25° C. for 1.5 hours. The mixture was treated with water and the organic phase was dried, concentrated and triturated with hexane to give 1.0 g (67%) of ethyl 5-chloro-3-methylbenzo(b) thiophene-2-carboxylate: mp 92.5–94° C.

Ethyl 3-bromomethyl-5-chlorobenzo(b)thiophene-2-carboxylate

A mixture of ethyl 5-chloro-3-methylbenzo(b)thiophene-2-carboxylate (9.0 g, 0.035 mol), N-bromosuccinimide (6.53 g, 0.037 mol) and benzoyl peroxide (130 mg) in carbon tetrachloride (150 ml) was refluxed and illuminated with sunlamp for 2 hours. The resulting suspension was cooled, filtered and the filter cake was triturated with methanol to give 9.9 g, (85%) of the methanol-insoluble ethyl 3-bromomethyl-5-chlorobenzo(b)thiophene-2-carboxylate: mp 148–150° C.

Ethyl 5-Chloro-3-[N-(2,2-dimethoxyethyl)-N-methyl (aminomethyl)]benzo(b)thiophene-2-carboxylate A mixture of ethyl 3-bromomethyl-5-chlorobenzo(b) thiophene-2-carboxylate (11 g, 0.033 mol), methylaminoacetaldehyde dimethyl acetal (4.76 g, 0.04 mol) and potassium carbonate (11.4 g, 0.8 mol) in dry acetone (200 ml) was stirred for 48 hours, filtered and the filtrate concentrated to give 11.8 g, (96%) of ethyl 5-chloro-3-(N-2,2-dimethoxyethyl)-N-methyl(aminomethyl)benzol(b) thiophene-2-carboxylate.

Ethyl 7-chloro-3,4-dihydro-4-methylthieno[4,3,2-ef]-[3] benzazepine-2-carboxylate Ethyl 5-chloro-3-[N-(2,2-dimethoxyethyl)-N-methyl (aminomethyl)]benzo[b]thiophene-2-carboxylate (3.0 g, 8.1 mmol) was added in portions to trifluoromethanesulfonic acid (10 ml) stirred at 0° C. under argon. The mixture was stirred at 25° C. for 45 minutes and diluted with water. The mixture was basified with aqueous sodium hydroxide and extracted with ethyl ether to give ethyl 7-chloro-3,4-dihydro-4-methylthieno-[4,3,2-ef][3]benzazepine-2-carboxylate.

Ethyl 7-chloro-3,4,5,6-tetrahydro-4-mothylthieno[4,3,2-ef][3]benzazepine-2-carboxylate Diborane in tetrahydrofuaran (1 M, 40 ml) was added to a solution of ethyl 7-chloro-3,4-dihydro-4-methylthieno[4, 3,2-ef][3]benzazepine-2-carboxylate (2.8 g) in tetrahydrofuran (30 ml) stirred at 0° C. The mixture was refluxed for 3 hours and stirred at 25° C. for 18 hours, cooled, treated with methanol (50 ml), refluxed for 18 hours and concentrated. The residue was triturated with ethyl ether-hexane (3:1) to give 1.6 g (84%) of ethyl 7-chloro-3,4,5,6-tetrahydro-4-methylthieno[4,3,2-ef][3]benzazepine-2-carboxylate:mp 138–140° C. The free base was treated with hydrogen chloride to give ethyl 7-chloro-3,4,5,6-tetrahydro-4-methylthieno[4,3,2-ef][3]benzazepine-2-carboxylate hydrochloride: mp 240° C.

7-Chloro-3,4,5,6-tetrahydro-4-methylthieno[4,3,2-ef][3] benzazepine-2-methanol

A solution of ethyl 7-chloro-3,4,5,6-tetrahydro-4-methylthieno(4.3.2-ef][3]benzazepine-2-carboxylate (4.0 g, 12.9 mmol), in ethyl ether (48 ml) was treated with lithium aluminum hydride (0.53 g, 14 mmol). The mixture was stirred for 1.5 hours, cooled and treated carefully with water (2.0 ml), 10% sodium hydroxide (1.0 ml) and water (2.0 ml).

The resulting mixture was filtered and the solvent evaporated to give 1.9 g (57%) of 7-chloro-3,4,5,6-tetrahydro-4-methylthieno[4,3,2-ef][3]benzazepine-2-methanol: mp 184–185° C.

7-Chloro-3,4,5,6-tetrahydro-4-methylthieno-4,3,2-ef][3] benzazepine-2-carboxaldehyde A solution of 7-chloro-3,4,5,6-tetrahydro-4-methylthieno [4,3,2-ef][3]benzazepine-2-methanol (1.6 g, 6 mmol) in dichloromethane (150 ml) was stirred under argon with activated manganese dioxide (8.3 g) for 2 hours. The mixture was filtered through Celite™ and the filtrate was dried with magnesium sulfate and concentrated to give a 63% yield of 7-chloro-3,4,5,6-tetrahydro-4-methylthieno[4,3,2-ef[[3]benzazepine-2-carboxaldehyde.

7-Chloro-2-ethenyl-3,4,5,6-tetrahdyro-4-methylthieno[4,3,2-ef][3]benzazepine (SKF-104856)

Sodium hydride (60% dispersion in mineral oil. 3.8 mmol) was added to a stirred solution of methyltriphenylphosphonium bromide (1.35 g, 3.8 mmol) in dry tetrahydrofuran (30 ml) and stirred for 15 minutes. The mixture was treated with a solution of 7-chloro-3,4,5,6-tetrahydro-4-methylthieno[4,3,2-ef][3]-benzazepine-2-carboxaldehyde, prepared as in Example 3, (0.5 g, 1.9 mmol) in dimethylformamide (4 ml), stirred at 25° C. for 16 hours, quenched with ice and extracted with ethyl acetate. The organic phase was washed, dried and concentrated and the residue was chromatographed on silica gel eluted with a gradient of methylene chloride to methanol-methylene chloride (3.5:96.5). The product was treated with hydrogen chloride to give 0.2 g (35%) of 7-chloro-2-ethenyl-3,4,5,6-tetrahydro-4-methylthieno [4,3,2-ef][3]benzazepine hydrochloride: mp 234–236° C.

The following is an example of the use of the cloned Human $\alpha_1$ adrenergic receptors to identify the relevant $\alpha_1$-Receptor subtype for the therapy of Benign Prostatic Hypertrophy.

EXAMPLE 6

Protocol for the Determination of the Potency of $\alpha_1$ Antagonists

The activity of compounds at the different human receptors was determined in vitro using cultured cell lines that selectively express the receptor of interest. These cell lines were prepared by transfecting the cloned cDNA or cloned genomic DNA or constructs containing both genomic DNA and cDNA encoding the human $\alpha$-adrenergic, serotonin, histamine, and dopamine receptors as follows:

$\alpha_{1A}$ Human Adrenergic Receptor: The entire coding region of $\alpha$1A (1719 bp), including 150 basepairs of 5' untranslated sequence (5' UT) and 300 bp of 3' untranslated sequence (3' UT), was cloned into the BamHI and ClaI sites of the polylinker-modified eukaryotic expression vector pCEXV-3, called EXJ.HR. The construct involved the ligation of partial overlapping human lymphocyte genomic and hippocampal cDNA clones: 5' sequence were contained on a 1.2 kb SmaI-XhoI genomic fragment (the vector-derived BamHI site was used for subcloning instead of the internal insert-derived SmaI site) and 3' sequences were contained on an 1.3 kb XhoI-ClaI cDNA fragment (the ClaI site was from the vector polylinker). Stable cell lines were obtained by cotransfection with the plasmid $\alpha$1A/EXJ (expression vector containing the $\alpha$1A receptor gene) and the plasmid pGCcos3neo (plasmid containing the aminoglycoside transferase gene) into LM(tk$^-$), CHO, and NIH3T3 cells, using calcium phosphate technique. The cells were grown, in a controlled environment (37° C., 5% $CO_2$), as monolayers in Dulbecco's modified Eagle's Medium (GIBCO, Grand Island, N.Y.) containing 25 mM glucose and supplemented with 10% bovine calf serum, 100 units/ml penicillin g, and 100 $\mu$g/ml streptomycin sulfate. Stable clones were then selected for resistance to the antibiotic G-418 (1 mg/ml), and membranes were harvested and assayed for their ability to bind [$^3$H]prazosin as described below (see "Radioligand Binding assays").

$\alpha_{1B}$ Human Adrenergic Receptor:

The entire coding region of $\alpha$1B (1563 bp), including 200 basepairs and 5' untranslated sequence (5' UT) and 600 bp of 3' untranslated sequence (3' UT), was cloned into the EcoRI site of pCEXV-3 eukaryotic expression vector. The construct involved ligating the full-length containing EcoRI brainstem cDNA fragment from λ ZapII into the expression vector. Stable cell lines were selected as described above.

$\alpha_{1C}$ Human Adrenergic Receptor:

The entire coding region of $\alpha_{1C}$ (1401 bp), including 400 basepairs of 5' untranslated sequence (5' UT) and 200 bp of 3' untranslated sequence (3' UT), was cloned into the KpnI site of the polylinker-modified pCEXV-3-derived eukaryotic expression vector, EXJ.RH. The construct involved ligating three partial overlapping fragments: a 5' 0.6 kb HincII genomic clone, a central 1.8 EcoRI hippocampal cDNA clone, and a 3' 0.6Kb PstI genomic clone. The hippocampal cDNA fragment overlaps with the 5' and 3' genomic clones so that the HincII and PstI sites at the 5' and 3' ends of the cDNA clone, respectively, were utilized for ligation. This full-length clone was cloned into the KpnI site of the expression vector, using the 5' and 3' KpnI sites of the fragment, derived from vector (i.e., pBluescript) and 3'-untranslated sequences, respectively. Stable cell lines were selected as described above.

Radioligand Binding Assays:

Transfected cells from culture flasks were scraped into 5 ml of 5 mM Tris-HCl, 5 mM EDTA, pH 7.5, and lysed by sonication. The cell lysates were centrifuged at 1000 rpm for 5 min at 4° C., and the supernatant was centrifuged at 30,000×g for 20 min at 4° C. The pellet was suspended in 50 mM Tris-HCl, 1 mM $MgCl_2$, and 0.1% ascorbic acid at pH 7.5. Binding of the $\alpha$1 antagonist [$^3$H]prazosin (0.5 nM, specific activity 76.2 Ci/mmol) to membrane preparations of LM(tk-) cells was done in a final volume of 0.25 ml and incubated at 37° C. for 20 min. Nonspecific binding was determined in the presence of 10 $\mu$M phentolamine. The reaction was stopped by filtration through GF/B filters using a cell harvester. Inhibition experiments, routinely consisting of 7 concentrations of the tested compounds, were analyzed using a non-linear regression curve-fitting computer program to obtain Ki values.

EXAMPLE 7

Functional Properties of $\alpha_1$ Antagonists in the Human Prostate

The efficacy of $\alpha_1$ adrenergic antagonists for the treatment of benign prostatic hyperplasia (BPH) is related to their ability to elicit relaxation of prostate smooth muscle. An index of this efficacy can be obtained by determining the potency of $\alpha_1$ antagonists to antagonize the contraction of human prostatic tissue induced by an $\alpha_1$ agonist "in vitro". Furthermore, by comparing the potency of subtype selective $\alpha_1$ antagonists in binding assays using human $\alpha_1$ receptors with their potency to inhibit agonist-induced smooth muscle contraction, it is possible to determine which of the $\alpha_1$ adrenergic receptor subtypes is involved in the contraction of prostate smooth muscle.

Methods:

Prostatic adenomas were obtained at the time of surgery from patients with symptomatic BPH. These were cut into longitudinal strips of 15 mm long and 2–4 mm wide, and suspended in 5 ml organ baths containing Krebs buffer (pH 7.4). The baths were maintained at 37° C. and continuously oxygenated with 5% $CO_2$ and 95% $O_2$. Isometric tension was measured with a Grass Instrument FT03 force transducer interfaced with a computer. Tissue strips were contracted with varying concentrations of phenylephrine after incubating for 20 minutes in the absence and presence of at least three different concentrations of antagonist. Dose-response curves for phenylephrine were constructed, and the antagonist potency ($pA_2$) was estimated by the dose-ratio method. The concentration of some antagonists in the tissue bath was assessed by measuring the displacement of [3H] prazosin by aliquots of the bath medium, using membrane preparations of the cloned human $\alpha_{1C}$ receptor. This control was necessary to account for losses of antagonist due to adsorption to the tissue bath and/or metabolism during the time the antagonists were equilibrated with the prostate tissue.

Results:

Table 3 shows that the $pA_2$ values measured for a series of $\alpha_1$ antagonists in human prostate tissue correlate closely (r=0.76) with the corresponding $pK_i$ values measured in the $\alpha_{1C}$ receptor assays. In contrast, the human prostate $pA_2$ values correlate poorly with the $pK_i$ values measured at the $\alpha_{1A}$ (r=−0.06) and $\alpha_{1B}$ (r=−0.24) adrenergic receptors. (See FIG. 7.) Thus, antagonists which are more potent at blocking the $\alpha_{1C}$ adrenergic receptor are more effective at blocking the contraction of the human prostate than antagonists which are more potent at the $\alpha_{1A}$ or $\alpha_{1B}$ adrenergic receptors. In addition, antagonists which are selective for the $\alpha_{1C}$ receptor will have a better therapeutic ratio than nonselective $\alpha$ antagonists.

TABLE 3

COMPARISON OF THE BINDING POTENCY ($pK_1$) OF ALPHA-1 ANTAGONISTS IN CLONED HUMAN RECEPTORS AND THEIR PROTENCY ($pA_2$) TO INHIBIT PROSTATE SMOOTH MUSCLE CONTRACTION

| | Compound | Human Alpha-1 Adrenergic ($pK_1$) | | | Human Prostate (PA) |
|---|---|---|---|---|---|
| | | a1A | a1B | a1C | |
| 1 | Prazosin | 9.48 | 9.26 | 9.Z3 | 9.08 |
| 3 | A-30360 | 7.49 | 7.86 | 8.52 | 8.72 |
| 4 | 5-Methyl-Urapidil | 7.79 | 6.77 | 8.35 | 8.38 |
| 5 | Indoramin | 6.74 | 7.39 | 8.35 | 7.86 |
| 6 | SKF-104856 | 8.48 | 7.50 | 7.60 | 7.66 |
| 7 | Compound 7 | 6.82 | 7.18 | 8.42 | 7.63 |
| 9 | Compound 9 | 6.12 | 6.76 | 7.83 | 7.41 |
| 10 | Terazosin | 8.46 | 8.71 | 8.16 | 7.30 |

References

1. Borden, L. A., Maxfield, F. R., Goldman, J. E., and Shelanski, M. L., Neurobiol. Aging., 13, 33–38, 1991.
2. Bruno, J. F., J. Whittaker, J. Song, and M. Berelowitz. Biochem. Biophys. Res. Comm. 179, 1485–1490 (1991).
3. Bush, A. W., Borden, L. A., Greene, L. A., and Maxfield, F. R., J. Neurochem. 57, 562–574, 1991.
4. Cotecchia, S., Schwinn, D. A., Randall, R. R., Lefkowitz, R. J., Caron, M. G., and Kobilka, B. K., Proc. Natl. Acad. Sci. USA, 85, 7159–7163, 1988.
5. Feinberg, A. P., and B. Vogelstein. Anal. Biochem. 132, 6–13 (1983).
6. Flavahan, N. A. and Vanhoutte, P. M., In: The Alpha-1 Adrenergic Receptors, (ed. by R. R. Ruffolo, Jr., Humana Press, Clifton N.J.) pp. 351–403, 1987.
7. Forray, C., and El-Fakahany, E. E., Mol. Pharmacol., 37, 893–902, 1990.
8. Graziadei, I., Zernig, G., Boer, R., and Glossman, H., Eur. J. Pharmacol. 172, 329–337, 1989.
9. Gross, G., Hanft, G., and Rugevics, C., Eur. J. Pharmacol., 151,333–335, 1989.
10. Hieble, J. P., Sarau, H. M., Foley, J. J., DeMarinis, R. M., and Pendleton, P. G., Naunyn-Schmiedeberg's Arch. Pharmacol., 318, 267–273, 1982.
11. Langer, S. Z., Pharmacol. Rev., 32, 377–360, 1980.
12. Lomasney, J. W., Cotecchia, S., Lorenz, W., Leung, W.-Y., Schwinn, D. A., Yang-Feng, T. L., Brownstein, M., Lefkowitz, R. J., and Caron, M., J. Biol. Chem., 266, 6365–6369, 1991.
13. Miller, J. and R. N. Germain. J. Exp. Med. 164, 1478–1489 (1986).
14. Minneman, K. P., Pharmacol. Rev., 40, 87–119, 1988.
15. Morrow, A. L., and Creese, I., Mol. Pharmacol., 29, 321–330, 1986.
16. Perez, D. M., M. T. Piascik, and R. M. Graham. Mol. Pharmacol. 40, 876–883 (1991).
17. Sambrook, J., Fritsch, E. F., and Maniatis, T., In: Molecular Cloning: A Laboratory Manual, $2^{nd}$ Edition (Cold Spring Harbor Lab., Cold Spring Harbor, N.Y.), 1989.
18. Sanger, S. Proc. Natl. Acad. Sci. USA 74, 5463–5467 (1977).
19. Sawutz, D. G., S. M. Lanier, C. D. Warren, and R. M. Graham. Mol. Pharmacol. 32, 565–571 (1987).
20. Schwinn, D. A., Lomasney, J. W., Lorenz, W., Szklut, P. J., Fremeau, R. T., Yang-Feng, T. L., Caron, M. G., Lefkowitz, R. J. and Cotecchia, S., J. Biol. Chem., 265, 8183–8189, 1990.
21. Schwinn, D. A., Page, S. A., Middleton, J. P., Lorenz, W., Liggett, S. B., Yamamoto, E., Lapetina, E. G., Caron, M. G., Lefkowitz, R. J., and Cotecchia, S., Mol. Pharmacol., 40, 619–626, 1991.
22. Southern, E. M. J. Mol. Biol. 98,503–505 (1975). Starke, S., Rev. Physiol. Biochem. Pharmacol., 88, 199–236, 1981.
23. Timmermans, P. B. M. W. M., Karamat Ali, F., Kwa, H. Y., Schoop, A. M. C., Slothorst-Grisdijk, F. P., and van Zwieten, P. A., Mol. Pharmacol., 20, 295–301, 1981.
24. Timmermans, P. B. M. W. M., and Thoolen. M. J. M. C., In: The Alpha-1 Adrenergic Receptors, (ed. by R. R. Ruffolo, Jr., Humana Press, Clifton N.J.) pp. 113–187, 1987.
25. Voigt, M. M., J. Kispert, and H. Chin. Nucleic Acid Res. 18, 1053 (1990).
26. Weinshank, R. L., Zgombick, J. M., Macchi, M., Adham, N., Lichtblau, H., Branchek, T. A., and Hartig, P. R., Mol. OPharmacol., 38, 681–688, 1990.
27. Cohen, J., (1993) J. Clin. Pharmacol., 33, 272–278.
28. Manning, A. S. and Hearse, D. J., (1984) J. Mol. Cell Cardiol., 16: 497–518.
29. Benfey, B. G., (1992) Can. J. Physiol. Pharmacol., 71: 103–111.
30. Cubeddu, L. X., (1984) American Heart Journal, 116: 133–161.
31. Nishimura, K., Kuwayama, Y., Matsugi, T., Sun, N., and Shirasawa, E., (1993) Investigative Ophthal. & Visual Sci., 34: 1761–1765.
32. Kincaid-Smith, P., (1989) Journal of Human Hypertension, 2743: 75–83.

33. Ames, R. P. and Kiyasu, J. Y., (1989) J. Clin. Pharmacol., 29: 123–127.
34. Pool, J. L., (1991) Am. Heart J., 121: 251–260.
35. Christ, G. J., Schwartz, C. B., Stone, B. A., Parker, M., Janis, M., Gondre, M., Valcic, M., and Melman, A., (1992) Amer. Physiological Soc., H15–H20.
36. Rosenthal, J., (1989) Journal of Human Hypertension, 3: 85–91.
37. Kowala, M. C. and Nicolosi, R. J., (1989) Journal of Cardiovascular Pharm., 13: 545–549.
38. Nash, D. T., (1990) Clin. Cardiol., 13: 764–772.
39. Waite, M. A., (1991) Journal of Internal Medicine, 229: 113–117.
40. Achari, R. and Laddu, A., (1992) J. Clin. Pharm., 32: 520–523.
41. Kowala, M. C., Nunnari, J. J., Durham, S. K., and Nicolosi, R. J., (1991) Athersclerosis, 91: 35–39.
42. Krupp, M. N., Hoover, K. W., and Valentine, J. J., (1989) Journal of Cardiovascular Pharm., 13: 511–519.
43. Jansen, H., Lammers, R., Baggen, M. G. A., and Birkenhager, J. C., (1989) Journal of Cardiovascular Pharm., 13: S5–S10.
44. Joint National Committee on Detection, Evaluation, and Treatment of High Blood Pressure, (1993) Archives of Internal Medicine, 163: 164–183.
45. Sourander, L. B., (1990) Gerontology, 36: 19–25.
46. Empey, D. W. and Medder, K. T., (1988) Drugs, 35: 438–443.
47. Andersson, K. E., (1988) Drugs, 35: 477–494.
48. MacDonald, E., Ruskoaho, H., Scheinen, M. and Virtanen, R., (1988) Annals of Clin. Res., 20: 298–310.
49. Lepor, H., R. Tan, S. Meretyk, and E. Shapiro. Alpha$_1$ adrenoceptor subtypes in the human prostate. J. Urol. 149:640–642 (1993).
50. Lepor, H., S. Auerbach, A Puras-Baez, P. Narayan, M. Soloway, F. Lowe, T. Moon, G. Leifer, and P. Madsen. A randomized, placebo-controlled multicenter study of the efficacy and safety of teazosin in the treatment of benign porstatic hyperplasia. J. Urol. 148:1467–4174 (1992).
51. Price, D. T., R. J. Lefkowitz, M. G. Caron, and D. A. Schwinn. Alpha$_1$-adrenergic receptor mRNA expression in human tissues. FASEB J. 7:A141 (1993).

What is claimed:

1. A process for identifying a chemical compound which specifically binds to a human $\alpha_{1C}$ adrenergic receptor which comprises contacting cells expressing on their cell surface the $\alpha_{1C}$ adrenergic receptor, with the compound under conditions suitable for binding, and detecting specific binding of the chemical compound to the $\alpha_{1C}$ adrenergic receptor, wherein such cells do not normally express the $\alpha_{1C}$ adrenergic receptor.

2. A process for identifying a chemical compound which specifically binds to a human $\alpha_{1C}$ adrenergic receptor which comprises contacting a membrane fraction from cells expressing on their cell surface the $\alpha_{1C}$ adrenergic receptor, with the compound under conditions suitable for binding, and detecting specific binding of the chemical compound to the $\alpha_{1C}$ adrenergic receptor, wherein such cells do not normally express the $\alpha_{1C}$ adrenergic receptor.

3. A process for determining whether a chemical compound is a human $\alpha_{1C}$ adrenergic receptor agonist which comprises contacting cells transfected with and expressing DNA encoding the $\alpha_{1C}$ adrenergic receptor with the compound under conditions permitting the activation of the $\alpha_{1C}$ adrenergic receptor, and detecting an increase in $\alpha_{1C}$ adrenergic receptor activity, so as to thereby determine whether the compound is an $\alpha_{1C}$ adrenergic receptor agonist.

4. A process for determining whether a chemical compound is a human $\alpha_{1C}$ adrenergic receptor agonist which comprises contacting a membrane fraction from cells transfected with and expressing DNA encoding the $\alpha_{1C}$ adrenergic receptor, with the compound under conditions permitting the activation of the $\alpha_{1C}$ adrenergic receptor, and detecting an increase in $\alpha_{1C}$ adrenergic receptor activity, so as to thereby determine whether the compound is an $\alpha_{1C}$ adrenergic receptor agonist.

5. A process for determining whether a chemical compound is a human $\alpha_{1C}$ adrenergic receptor antagonist which comprises contacting cells transfected with and expressing DNA encoding the $\alpha_{1C}$ adrenergic receptor with the compound in the presence of a known $\alpha_{1C}$ adrenergic receptor agonist, under conditions permitting the activation of the $\alpha_{1C}$ adrenergic receptor, and detecting a decrease in $\alpha_{1C}$ adrenergic receptor activity, so as to thereby determine whether the compound is an $\alpha_{1C}$ adrenergic receptor antagonist.

6. A process for determining whether a chemical compound is a human $\alpha_{1C}$ adrenergic receptor antagonist which comprises contacting a membrane fraction from cells transfected with and expressing DNA encoding the $\alpha_{1C}$ adrenergic receptor, with the compound under conditions permitting the activation of the $\alpha_{1C}$ adrenergic receptor, and detecting a decrease in $\alpha_{1C}$ adrenergic receptor activity, so as to thereby determine whether the compound is an $\alpha_{1C}$ adrenergic receptor antagonist.

7. The process of any one of claim 1, 2, 3, 4, 5 or 6, wherein the cells are mammalian cell.

8. The process of claim 7, wherein the mammalian cells are nonneurbnal in origin.

9. The process of claim 8, wherein the nonneuronal cells are COS-7 cells, 293 human embryonic kidney cells, CHO cells, NIH-3T3 cells or LM(tk$^-$) cells.

10. A process involving competitive binding for identifying a chemical compound which specifically binds to a human $\alpha_{1C}$ adrenergic receptor which comprises contacting cells expressing on their cell surface the $\alpha_{1C}$ adrenergic receptor, with both the chemical compound and a second chemical compound known to bind to the receptor, and separately with only the second chemical compound, under conditions suitable for binding of both compounds, and detecting specific binding of the chemical compound to the $\alpha_{1C}$ adrenergic receptor, a decrease in the binding of the second chemical compound to the $\alpha_{1C}$ adrenergic receptor in the presence of the chemical compound indicating that the chemical compound binds to the $\alpha_{1C}$ adrenergic receptor wherein such cells do not normally express the $\alpha_{1C}$ adrenergic receptor.

11. A process involving competitive binding for identifying a chemical compound which specifically binds to a human $\alpha_{1C}$ adrenergic receptor which comprises contacting a membrane fraction from cells expressing on their cell surface the $\alpha_{1C}$ adrenergic receptor, with both the chemical compound and a second chemical compound known to bind to the receptor, and separately with only the second chemical compound, under conditions suitable for binding of both compounds, and detecting specific binding of the chemical compound to the $\alpha_{1C}$ adrenergic receptor, a decrease in the binding of the second chemical compound to the $\alpha_{1C}$ adrenergic receptor in the presence of the chemical compound indicating that the chemical compound binds to the $\alpha_{1C}$ adrenergic receptor wherein such cells do not normally express the $\alpha_{1C}$ adrenergic receptor.

12. A process for determining whether a chemical compound specifically binds to and activates a human $\alpha_{1C}$ adrenergic receptor, which comprises contacting cells producing a second messenger response and expressing on their cell surface the $\alpha_{1C}$ adrenergic receptor, with the chemical compound under conditions suitable for activation of the $\alpha_{1C}$ adrenergic receptor, and measuring the second messenger response in the presence and in the absence of the chemical compound, a change in the second messenger response in the presence of the chemical compound indicating that the compound activates the $\alpha_{1C}$ adrenergic receptor wherein such cells do not normally express the $\alpha_{1C}$ adrenergic receptor.

13. A process for determining whether a chemical compound specifically binds to and activates a human $\alpha_{1C}$ adrenergic receptor, which comprises contacting a membrane fraction from cells producing a second messenger response and expressing on their cell surface the $\alpha_{1C}$ adrenergic receptor with the chemical compound under conditions suitable for activation of the $\alpha_{1C}$ adrenergic receptor, and measuring the second messenger response in the presence and in the absence of the chemical compound, a change in the second messenger response in the presence of the chemical compound indicating that the compound activates the $\alpha_{1C}$ adrenergic receptor, wherein such cells do not normally express the $\alpha_{1C}$ adrenergic receptor.

14. A process for determining whether a chemical compound specifically binds to and inhibits activation of a human $\alpha_{1C}$ adrenergic receptor which comprises contacting cells producing a second messenger response and expressing on their cell surface the $\alpha_{1C}$ adrenergic receptor with both the chemical compound and a second chemical compound known to activate the $\alpha_{1C}$ adrenergic receptor, and separately with only the second chemical compound, under conditions suitable for activation of the $\alpha_{1C}$ adrenergic receptor, and measuring the second messenger response in the presence of only the second chemical compound and in the presence of both the second chemical compound and the chemical compound, a smaller change in the second messenger response in the presence of both the chemical compound and the second chemical compound than in the presence of only the second chemical compound indicating that the chemical compound inhibits activation of the $\alpha_{1C}$ adrenergic receptor, wherein such cells do not normally express the $\alpha_{1C}$ adrenergic receptor.

15. A process for determining whether a chemical compound specifically binds to and inhibits activation of a human $\alpha_{1C}$ adrenergic receptor which comprises contacting a membrane fraction from cells producing a second messenger response and expressing on their cell surface the $\alpha_{1C}$ adrenergic receptor with both the chemical compound and a second chemical compound known to activate the $\alpha_{1C}$ adrenergic receptor, and separately with only the second chemical compound, under conditions suitable for activation of the $\alpha_{1C}$ adrenergic receptor, and measuring the second messenger response in the presence of only the second chemical compound and in the presence of both the second chemical compound and the chemical compound, a smaller change in the second messenger response in the presence of both the chemical compound and the second chemical compound than in the presence of only the second chemical compound indicating that the chemical compound inhibits activation of the $\alpha_{1C}$ adrenergic receptor, wherein such cells do not normally express the $\alpha_{1C}$ adrenergic receptor.

16. The process of claim 12, wherein the second messenger response comprises intracellular calcium levels and the change in second messenger response is an increase in intracellular calcium levels.

17. The process of claim 12 or 13, wherein the second messenger response comprises inositol phospholipid hydrolysis and the change in second messenger response is an increase in inositol phospholipid hydrolysis.

18. The process of claim 14, wherein the second messenger response comprises intracellular calcium levels, and the change in second messenger response is a smaller increase in the intracellular calcium levels in the presence of both the chemical compound and the second chemical compound than in the presence of only the second chemical compound.

19. The process of claim 14 or 15, wherein the second messenger response comprises inositol phospholipid hydrolysis, and the change in second messenger response is a smaller increase in inositol phospholipid hydrolysis in the presence of both the chemical compound and the second chemical compound than in the presence of only the second chemical compound.

20. A method of screening a plurality of chemical compounds not known to bind to a human $\alpha_{1C}$ adrenergic receptor to identify a compound which specifically binds to the $\alpha_{1C}$ adrenergic receptor, which comprises (a) contacting cells transfected with and expressing DNA encoding the $\alpha_{1C}$ adrenergic receptor with a compound known to bind specifically to the $\alpha_{1C}$ adrenergic receptor;

(b) contacting the preparation of step (a) with the plurality of compounds not known to bind specifically to the $\alpha_{1C}$ adrenergic receptor, under conditions permitting binding of compounds known to bind the $\alpha_{1C}$ adrenergic receptor;

(c) determining whether the binding of the compound known to bind to the $\alpha_{1C}$ adrenergic receptor is reduced in the presence of the compounds, relative to the binding of the compound in the absence of the plurality of compounds; and if so (d) separately determining the binding to the $\alpha_{1C}$ adrenergic receptor of each compound included in the plurality of compounds, so as to thereby identify the compound which specifically binds to the $\alpha_{1C}$ adrenergic receptor.

21. A method of screening a plurality of chemical compounds not known to bind to a human $\alpha_{1C}$ adrenergic receptor to identify a compound which specifically binds to the $\alpha_{1C}$ adrenergic receptor, which comprises (a) contacting a membrane fraction from cells transfected with and expressing DNA encoding the $\alpha_{1C}$ adrenergic receptor, with a compound known to bind specifically to the $\alpha_{1C}$ adrenergic receptor;

(b) contacting the preparation of step (a) with the plurality of compounds not known to bind specifically to the $\alpha_{1C}$ adrenergic receptor, under conditions permitting binding of compounds known to bind the $\alpha_{1C}$ adrenergic receptor;

(c) determining whether the binding of the compound known to bind to the $\alpha_{1C}$ adrenergic receptor is reduced in the presence of the compounds, relative to the binding of the compound in the absence of the plurality of compounds; and if so (d) separately determining the binding to the $\alpha_{1C}$ adrenergic receptor of each compound included in the plurality of compounds, so as to thereby identify the compound which specifically binds to the $\alpha_{1C}$ adrenergic receptor.

22. A method of screening a plurality of chemical compounds not known to activate a human $\alpha_{1C}$ adrenergic receptor to identify a compound which activates the $\alpha_{1C}$ adrenergic receptor which comprises (a) contacting cells transfected with and expressing the $\alpha_{1C}$ adrenergic receptor with the plurality of compounds not known to activate the $\alpha_{1C}$ adrenergic receptor, under conditions permitting activation of the $\alpha_{1C}$ adrenergic receptor;

(b) determining whether the activity of the $\alpha_{1C}$ adrenergic receptor is increased in the presence of the compounds; and if so (c) separately determining whether the activation of the $\alpha_{1C}$ adrenergic receptor is increased by each compound included in the plurality of compounds, so as to thereby identify the compound which activates the $\alpha_{1C}$ adrenergic receptor.

23. A method of screening a plurality of chemical compounds not known to activate a human $\alpha_{1C}$ adrenergic receptor to identify a compound which activates the $\alpha_{1C}$ adrenergic receptor which comprises (a) contacting a membrane fraction from cells transfected with and expressing DNA encoding the $\alpha_{1C}$ adrenergic receptor, with a plurality of compounds not known to activate the $\alpha_{1C}$ adrenergic receptor, under conditions permitting activation of the $\alpha_{1C}$ adrenergic receptor;

(b) determining whether the activity of the $\alpha_{1C}$ adrenergic receptor is increased in the presence of the compounds; and if so (c) separately determining whether the activation of the $\alpha_{1C}$ adrenergic receptor is increased by each compound included in the plurality of compounds, so as to thereby identify the compound which activates the $\alpha_{1C}$ adrenergic receptor.

24. A method of screening a plurality of chemical compounds not known to inhibit the activation of a human $\alpha_{1C}$ adrenergic receptor to identify a compound which inhibits the activation of the $\alpha_{1C}$ adrenergic receptor, which comprises:

(a) contacting cells transfected with and expressing the $\alpha_{1C}$ adrenergic receptor with the plurality of compounds in the presence of a known $\alpha_{1C}$ adrenergic receptor agonist, under conditions permitting activation of the $\alpha_{1C}$ adrenergic receptor;

(b) determining whether the activation of the $\alpha_{1C}$ adrenergic receptor is reduced in the presence of the plurality of compounds, relative to the activation of the $\alpha_{1C}$ adrenergic receptor in the absence of the plurality of compounds; and if so (c) separately determining the inhibition of activation of the $\alpha_{1C}$ adrenergic receptor for each compound included in the plurality of compounds, so as to thereby identify the compound which inhibits the activation of the $\alpha_{1C}$ adrenergic receptor.

25. A method of screening a plurality of chemical compounds not known to inhibit the activation of a human $\alpha_{1C}$ adrenergic receptor to identify a compound which inhibits the activation of the $\alpha_{1C}$ adrenergic receptor, which comprises:

(a) contacting a membrane fraction from cells transfected with and expressing DNA encoding the $\alpha_{1C}$ adrenergic receptor, with the plurality of compounds in the presence of a known $\alpha_{1C}$ adrenergic receptor agonist, under conditions permitting activation of the $\alpha_{1C}$ adrenergic receptor;

(b) determining whether the activation of the $\alpha_{1C}$ adrenergic receptor is reduced in the presence of the plurality of compounds, relative to the activation of the $\alpha_{1C}$ adrenergic receptor in the absence of the plurality of compounds; and if so (c) separately determining the inhibition of activation of the $\alpha_{1C}$ adrenergic-receptor for each compound included in the plurality of compounds, so as to thereby identify the compound which inhibits the activation of the $\alpha_{1C}$ adrenergic receptor.

26. A method of any one of claim 3, 4, 5, 6, 22, 23, 24 or 25, wherein activation of the $\alpha_{1C}$ adrenergic receptor is determined by a second messenger assay.

27. The method of claim 26, wherein the second messenger is intracellular calcium, or an inositol phospholipid.

28. A method of any one of claims 20, 21, 22, 23 or 24, wherein the cells are mammalian cell.

29. A method of claim 28, wherein the mammalian cells are non-neuronal in origin.

30. The method of claim 29, wherein the non-neuronal cells are COS-7 cells, 293 human embryonic kidney cells, CHO cells, LM(tk$^-$) cells or NIH-3T3 cells.

31. A method of preparing a pharmaceutical composition which comprises determining whether a compound is an $\alpha_{1C}$ adrenergic receptor agonist or antagonist using the method of any of claim 3–6 and admixing said compound with a pharmaceutically acceptable carrier.

* * * * *

SEQUENCE LISTING (1) GENERAL INFORMATION:

(iii) NUMBER OF SEQUENCES: 23

(2) INFORMATION FOR SEQ ID NO:1:

(i) SEQUENCE CHARACTERISTICS:
      (A) LENGTH: 2140 base pairs
      (B) TYPE: nucleic acid
      (C) STRANDEDNESS: single
      (D) TOPOLOGY: unknown (ii) MOLECULE TYPE: DNA (genomic)

(iii) HYPOTHETICAL: N (iv) ANTI-SENSE: N (ix) FEATURE:
      (A) NAME/KEY: CDS
      (B) LOCATION: 178..1893
      (D) OTHER INFORMATION:

(xi) SEQUENCE DESCRIPTION: SEQ ID NO:1:

```
CCGGGCCAGG CACGTCCGCT CTCGGACAGC CGCTCCGCGT CACAGGAACT TGGGCAGGAC        60

CCGACGGGAC CCGTGCGCGG AGCTGCATCT GGAGCCCCGC GGCTATGCCC TGTGCTCCCC       120

TCCTGCCGGC CGCTCGTTCT GTGCCCCCGG CCCGGCCACC GACGGCCGCG CGTTGAG         177

ATG ACT TTC CGC GAT CTC CTG AGC GTC AGT TTC GAG GGA CCC CGC CCG       225
Met Thr Phe Arg Asp Leu Leu Ser Val Ser Phe Glu Gly Pro Arg Pro
 1               5                  10                  15

GAC AGC AGC GCA GGG GGC TCC AGC GCG GGC GGC GGC GGG GGC AGC GCG       273
Asp Ser Ser Ala Gly Gly Ser Ser Ala Gly Gly Gly Gly Gly Ser Ala
             20                  25                  30

GGC GGC GCG GCC CCC TCG GAG GGC CCG GCG GTG GGC GGC GTG CCG GGG       321
Gly Gly Ala Ala Pro Ser Glu Gly Pro Ala Val Gly Gly Val Pro Gly
         35                  40                  45

GGC GCG GGC GGC GGC GGC GGC GTG GTG GGC GCA GGC AGC GGC GAG GAC       369
Gly Ala Gly Gly Gly Gly Gly Val Val Gly Ala Gly Ser Gly Glu Asp
     50                  55                  60
```

```
AAC CGG AGC TCC GCG GGG GAG CCG GGG AGC GCG GGC GCG GGC GGC GAC        417
Asn Arg Ser Ser Ala Gly Glu Pro Gly Ser Ala Gly Ala Gly Gly Asp
 65              70                  75                  80

GTG AAT GGC ACG GCG GCC GTC GGG GGA CTG GTG GTG AGC GCG CAG GGC        465
Val Asn Gly Thr Ala Ala Val Gly Gly Leu Val Val Ser Ala Gln Gly
             85                  90                  95

GTG GGC GTG GGC GTC TTC CTG GCA GCC TTC ATC CTT ATG GCC GTG GCA        513
Val Gly Val Gly Val Phe Leu Ala Ala Phe Ile Leu Met Ala Val Ala
             100                 105                 110

GGT AAC CTG CTT GTC ATC CTC TCA GTG GCC TGC AAC CGC CAC CTG CAG        561
Gly Asn Leu Leu Val Ile Leu Ser Val Ala Cys Asn Arg His Leu Gln
             115                 120                 125

ACC GTC ACC AAC TAT TTC ATC GTG AAC CTG GCC GTG GCC GAC CTG CTG        609
Thr Val Thr Asn Tyr Phe Ile Val Asn Leu Ala Val Ala Asp Leu Leu
 130                 135                 140

CTG AGC GCC ACC GTA CTG CCC TTC TCG GCC ACC ATG GAG GTT CTG GGC        657
Leu Ser Ala Thr Val Leu Pro Phe Ser Ala Thr Met Glu Val Leu Gly
145                 150                 155                 160

TTC TGG GCC TTT GGC CGC GCC TTC TGC GAC GTA TGG GCC GCC GTG GAC        705
Phe Trp Ala Phe Gly Arg Ala Phe Cys Asp Val Trp Ala Ala Val Asp
                 165                 170                 175

GTG CTG TGC TGC ACG GCC TCC ATC CTC AGC CTC TGC ACC ATC TCC GTG        753
Val Leu Cys Cys Thr Ala Ser Ile Leu Ser Leu Cys Thr Ile Ser Val
             180                 185                 190

GAC CGG TAC GTG GGC GTG CGC CAC TCA CTC AAG TAC CCA GCC ATC ATG        801
Asp Arg Tyr Val Gly Val Arg His Ser Leu Lys Tyr Pro Ala Ile Met
             195                 200                 205

ACC GAG CGC AAG GCG GCC GCC ATC CTG GCC CTG CTC TGG GTC GTA GCC        849
Thr Glu Arg Lys Ala Ala Ala Ile Leu Ala Leu Leu Trp Val Val Ala
 210                 215                 220

CTG GTG GTG TCC GTA GGG CCC CTG CTG GGC TGG AAG GAG CCC GTG CCC        897
Leu Val Val Ser Val Gly Pro Leu Leu Gly Trp Lys Glu Pro Val Pro
225                 230                 235                 240

CCT GAC GAG CGC TTC TGC GGT ATC ACC GAG GAG GCG GGC TAC GCT GTC        945
Pro Asp Glu Arg Phe Cys Gly Ile Thr Glu Glu Ala Gly Tyr Ala Val
                 245                 250                 255

TTC TCC TCC GTG TGC TCC TTC TAC CTG CCC ATG GCG GTC ATC GTG GTC        993
Phe Ser Ser Val Cys Ser Phe Tyr Leu Pro Met Ala Val Ile Val Val
             260                 265                 270

ATG TAC TGC CGC GTG TAC GTG GTC GCG CGC AGC ACC ACG CGC AGC CTC       1041
Met Tyr Cys Arg Val Tyr Val Val Ala Arg Ser Thr Thr Arg Ser Leu
             275                 280                 285

GAG GCA GGC GTC AAG CGC GAG CGA GGC AAG GCC TCC GAG GTG GTG CTG       1089
Glu Ala Gly Val Lys Arg Glu Arg Gly Lys Ala Ser Glu Val Val Leu
 290                 295                 300

CGC ATC CAC TGT CGC GGC GCG GCC ACG GGC GCC GAC GGG GCG CAC GGC       1137
Arg Ile His Cys Arg Gly Ala Ala Thr Gly Ala Asp Gly Ala His Gly
305                 310                 315                 320

ATG CGC AGC GCC AAG GGC CAC ACC TTC CGC AGC TCG CTC TCC GTG CGC       1185
Met Arg Ser Ala Lys Gly His Thr Phe Arg Ser Ser Leu Ser Val Arg
                 325                 330                 335

CTG CTC AAG TTC TCC CGT GAG AAG AAA GCG GCC AAG ACT CTG GCC ATC       1233
Leu Leu Lys Phe Ser Arg Glu Lys Lys Ala Ala Lys Thr Leu Ala Ile
             340                 345                 350

GTC GTG GGT GTC TTC GTG CTC TGC TGG TTC CCT TTC TTC TTT GTC CTG       1281
Val Val Gly Val Phe Val Leu Cys Trp Phe Pro Phe Phe Phe Val Leu
             355                 360                 365

CCG CTC GGC TCC TTG TTC CCG CAG CTG AAG CCA TCG GAG GGC GTC TTC       1329
Pro Leu Gly Ser Leu Phe Pro Gln Leu Lys Pro Ser Glu Gly Val Phe
             370                 375                 380
```

-continued

| | | | | | | | | | | | | | |
|---|---|---|---|---|---|---|---|---|---|---|---|---|---|
| AAG | GTC | ATC | TTC | TGG | CTC | GGC | TAC | TTC | AAC | AGC | TGC | GTG | AAC | CCG | CTC | 1377 |
| Lys | Val | Ile | Phe | Trp | Leu | Gly | Tyr | Phe | Asn | Ser | Cys | Val | Asn | Pro | Leu | |
| 385 | | | | 390 | | | | | 395 | | | | | 400 | | |

```
AAG GTC ATC TTC TGG CTC GGC TAC TTC AAC AGC TGC GTG AAC CCG CTC           1377
Lys Val Ile Phe Trp Leu Gly Tyr Phe Asn Ser Cys Val Asn Pro Leu
385                 390                 395                 400

ATC TAC CCC TGT TCC AGC CGC GAG TTC AAG CGC GCC TTC CTC CGT CTC           1425
Ile Tyr Pro Cys Ser Ser Arg Glu Phe Lys Arg Ala Phe Leu Arg Leu
                    405                 410                 415

CTG CGC TGC CAG TGC CGT CGT CGC CGG CGC CGC CGC CCT CTC TGG CGT           1473
Leu Arg Cys Gln Cys Arg Arg Arg Arg Arg Arg Arg Pro Leu Trp Arg
                420                 425                 430

GTC TAC GGC CAC CAC TGG CGG GCC TCC ACC AGC GGC CTG CGC CAG GAC           1521
Val Tyr Gly His His Trp Arg Ala Ser Thr Ser Gly Leu Arg Gln Asp
            435                 440                 445

TGC GCC CCG AGT TCG GGC GAC GCG CCC CCC GGA GCG CCG CTG GCC CTC           1569
Cys Ala Pro Ser Ser Gly Asp Ala Pro Pro Gly Ala Pro Leu Ala Leu
        450                 455                 460

ACC GCG CTC CCC GAC CCC GAC CCC GAA CCC CCA GGC ACG CCC GAG ATG           1617
Thr Ala Leu Pro Asp Pro Asp Pro Glu Pro Pro Gly Thr Pro Glu Met
465                 470                 475                 480

CAG GCT CCG GTC GCC AGC CGT CGA AAG CCA CCC AGC GCC TTC CGC GAG           1665
Gln Ala Pro Val Ala Ser Arg Arg Lys Pro Pro Ser Ala Phe Arg Glu
                    485                 490                 495

TGG AGG CTG CTG GGG CCG TTC CGG AGA CCC ACG ACC CAG CTG CGC GCC           1713
Trp Arg Leu Leu Gly Pro Phe Arg Arg Pro Thr Thr Gln Leu Arg Ala
                500                 505                 510

AAA GTC TCC AGC CTG TCG CAC AAG ATC CGC GCC GGG GGC GCG CAG CGC           1761
Lys Val Ser Ser Leu Ser His Lys Ile Arg Ala Gly Gly Ala Gln Arg
            515                 520                 525

GCA GAG GCA GCG TGC GCC CAG CGC TCA GAG GTG GAG GCT GTG TCC CTA           1809
Ala Glu Ala Ala Cys Ala Gln Arg Ser Glu Val Glu Ala Val Ser Leu
        530                 535                 540

GGC GTC CCA CAC GAG GTG GCC GAG GGC GCC ACC TGC CAG GCC TAC GAA           1857
Gly Val Pro His Glu Val Ala Glu Gly Ala Thr Cys Gln Ala Tyr Glu
545                 550                 555                 560

TTG GCC GAC TAC AGC AAC CTA CGG GAG ACC GAT ATT TAAGGACCCC               1903
Leu Ala Asp Tyr Ser Asn Leu Arg Glu Thr Asp Ile
                    565                 570

AGAGCTAGGC CGCGGAGTGT GCTGGGCTTG GGGGTAAGGG GGACCAGAGA GGCGGGCTGG         1963

TGTTCTAAGA GCCCCCGTGC AAATCGGAGA CCCGGAAACT GATCAGGGCA GCTGCTCTGT         2023

GACATCCCTG AGGAACTGGG CAGAGCTTGA GGCTGGAGCC CTTGAAAGGT GAAAAGTAGT         2083

GGGGCCCCCT GCTGGACTCA GGTGCCCAGA ACTCTTTTCT TAGAAGGGAG AGGCTGC           2140

(2) INFORMATION FOR SEQ ID NO:2:

(i) SEQUENCE CHARACTERISTICS:
        (A) LENGTH: 572 amino acids
        (B) TYPE: amino acid
        (D) TOPOLOGY: linear (ii) MOLECULE TYPE: protein (xi) SEQUENCE DESCRIPTION: SEQ ID NO:2:

Met Thr Phe Arg Asp Leu Leu Ser Val Ser Phe Glu Gly Pro Arg Pro
1               5                   10                  15

Asp Ser Ser Ala Gly Gly Ser Ser Ala Gly Gly Gly Gly Ser Ala
            20                  25                  30

Gly Gly Ala Ala Pro Ser Glu Gly Pro Ala Val Gly Val Pro Gly
        35                  40                  45

Gly Ala Gly Gly Gly Gly Val Val Gly Ala Gly Ser Gly Glu Asp
    50                  55                  60
```

-continued

```
Asn Arg Ser Ser Ala Gly Glu Pro Gly Ser Ala Gly Ala Gly Asp
 65                  70                  75                  80

Val Asn Gly Thr Ala Ala Val Gly Gly Leu Val Val Ser Ala Gln Gly
                 85                  90                  95

Val Gly Val Gly Val Phe Leu Ala Ala Phe Ile Leu Met Ala Val Ala
            100                 105                 110

Gly Asn Leu Leu Val Ile Leu Ser Val Ala Cys Asn Arg His Leu Gln
            115                 120                 125

Thr Val Thr Asn Tyr Phe Ile Val Asn Leu Ala Val Ala Asp Leu Leu
            130                 135                 140

Leu Ser Ala Thr Val Leu Pro Phe Ser Ala Thr Met Glu Val Leu Gly
145                 150                 155                 160

Phe Trp Ala Phe Gly Arg Ala Phe Cys Asp Val Trp Ala Ala Val Asp
                165                 170                 175

Val Leu Cys Cys Thr Ala Ser Ile Leu Ser Leu Cys Thr Ile Ser Val
            180                 185                 190

Asp Arg Tyr Val Gly Val Arg His Ser Leu Lys Tyr Pro Ala Ile Met
            195                 200                 205

Thr Glu Arg Lys Ala Ala Ala Ile Leu Ala Leu Leu Trp Val Val Ala
            210                 215                 220

Leu Val Val Ser Val Gly Pro Leu Leu Gly Trp Lys Glu Pro Val Pro
225                 230                 235                 240

Pro Asp Glu Arg Phe Cys Gly Ile Thr Glu Glu Ala Gly Tyr Ala Val
                245                 250                 255

Phe Ser Ser Val Cys Ser Phe Tyr Leu Pro Met Ala Val Ile Val Val
                260                 265                 270

Met Tyr Cys Arg Val Tyr Val Val Ala Arg Ser Thr Thr Arg Ser Leu
            275                 280                 285

Glu Ala Gly Val Lys Arg Glu Arg Gly Lys Ala Ser Glu Val Val Leu
            290                 295                 300

Arg Ile His Cys Arg Gly Ala Ala Thr Gly Ala Asp Gly Ala His Gly
305                 310                 315                 320

Met Arg Ser Ala Lys Gly His Thr Phe Arg Ser Ser Leu Ser Val Arg
                325                 330                 335

Leu Leu Lys Phe Ser Arg Glu Lys Lys Ala Ala Lys Thr Leu Ala Ile
            340                 345                 350

Val Val Gly Val Phe Val Leu Cys Trp Phe Pro Phe Phe Phe Val Leu
            355                 360                 365

Pro Leu Gly Ser Leu Phe Pro Gln Leu Lys Pro Ser Glu Gly Val Phe
370                 375                 380

Lys Val Ile Phe Trp Leu Gly Tyr Phe Asn Ser Cys Val Asn Pro Leu
385                 390                 395                 400

Ile Tyr Pro Cys Ser Ser Arg Glu Phe Lys Arg Ala Phe Leu Arg Leu
                405                 410                 415

Leu Arg Cys Gln Cys Arg Arg Arg Arg Arg Arg Pro Leu Trp Arg
                420                 425                 430

Val Tyr Gly His His Trp Arg Ala Ser Thr Ser Gly Leu Arg Gln Asp
            435                 440                 445

Cys Ala Pro Ser Ser Gly Asp Ala Pro Pro Gly Ala Pro Leu Ala Leu
            450                 455                 460

Thr Ala Leu Pro Asp Pro Asp Pro Glu Pro Pro Gly Thr Pro Glu Met
465                 470                 475                 480

Gln Ala Pro Val Ala Ser Arg Arg Lys Pro Pro Ser Ala Phe Arg Glu
                485                 490                 495
```

-continued

```
Trp Arg Leu Leu Gly Pro Phe Arg Arg Pro Thr Thr Gln Leu Arg Ala
            500                 505                 510

Lys Val Ser Ser Leu Ser His Lys Ile Arg Ala Gly Gly Ala Gln Arg
            515                 520                 525

Ala Glu Ala Ala Cys Ala Gln Arg Ser Glu Val Glu Ala Val Ser Leu
    530                 535                 540

Gly Val Pro His Glu Val Ala Glu Gly Ala Thr Cys Gln Ala Tyr Glu
545                 550                 555                 560

Leu Ala Asp Tyr Ser Asn Leu Arg Glu Thr Asp Ile
            565                 570
```

(2) INFORMATION FOR SEQ ID NO:3:

(i) SEQUENCE CHARACTERISTICS:
        (A) LENGTH: 1738 base pairs
        (B) TYPE: nucleic acid
        (C) STRANDEDNESS: single
        (D) TOPOLOGY: unknown (ii) MOLECULE TYPE: DNA (genomic)

(iii) HYPOTHETICAL: N (iv) ANTI-SENSE: N (ix) FEATURE:
        (A) NAME/KEY: CDS
        (B) LOCATION: 124..1683
        (D) OTHER INFORMATION:

(xi) SEQUENCE DESCRIPTION: SEQ ID NO:3:

```
GCCAGGAGGG CGCCTCTGGG AAGAAGACCA CGGGGGAAGC AAAGTTTCAG GGCAGCTGAG      60

GAGCCTTCGC CGCAGCCCTT CCGAGCCCAA TCATCCCCCA GGCTATGGAG GGCGGACTCT     120

AAG ATG AAT CCC GAC CTG GAC ACC GGC CAC AAC ACA TCA GCA CCT GCC       168
    Met Asn Pro Asp Leu Asp Thr Gly His Asn Thr Ser Ala Pro Ala
    1               5                  10                  15

CAC TGG GGA GAG TTG AAA AAT GCC AAC TTC ACT GGC CCC AAC CAG ACC       216
His Trp Gly Glu Leu Lys Asn Ala Asn Phe Thr Gly Pro Asn Gln Thr
            20                  25                  30

TCG AGC AAC TCC ACA CTG CCC CAG CTG GAC ATC ACC AGG GCC ATC TCT       264
Ser Ser Asn Ser Thr Leu Pro Gln Leu Asp Ile Thr Arg Ala Ile Ser
        35                  40                  45

GTG GGC CTG GTG CTG GGC GCC TTC ATC CTC TTT GCC ATC GTG GGC AAC       312
Val Gly Leu Val Leu Gly Ala Phe Ile Leu Phe Ala Ile Val Gly Asn
    50                  55                  60

ATC CTA GTC ATC TTG TCT GTG GCC TGC AAC CGG CAC CTG CGG ACG CCC       360
Ile Leu Val Ile Leu Ser Val Ala Cys Asn Arg His Leu Arg Thr Pro
65                  70                  75

ACC AAC TAC TTC ATT GTC AAC CTG GCC ATG GCC GAC CTG CTG TTG AGC       408
Thr Asn Tyr Phe Ile Val Asn Leu Ala Met Ala Asp Leu Leu Leu Ser
 80                  85                  90                  95

TTC ACC GTC CTG CCC TTC TCA GCG GCC CTA GAG GTG CTC GGC TAC TGG       456
Phe Thr Val Leu Pro Phe Ser Ala Ala Leu Glu Val Leu Gly Tyr Trp
            100                 105                 110

GTG CTG GGG CGG ATC TTC TGT GAC ATC TGG GCA GCC GTG GAT GTC CTG       504
Val Leu Gly Arg Ile Phe Cys Asp Ile Trp Ala Ala Val Asp Val Leu
        115                 120                 125

TGC TGC ACA GCG TCC ATT CTG AGC CTG TGC GCC ATC TCC ATC GAT CGC       552
Cys Cys Thr Ala Ser Ile Leu Ser Leu Cys Ala Ile Ser Ile Asp Arg
    130                 135                 140

TAC ATC GGG GTG CGC TAC TCT CTG CAG TAT CCC ACG CTG GTC ACC CGG       600
Tyr Ile Gly Val Arg Tyr Ser Leu Gln Tyr Pro Thr Leu Val Thr Arg
145                 150                 155
```

```
AGG AAG GCC ATC TTG GCG CTG CTC AGT GTC TGG GTC TTG TCC ACC GTC        648
Arg Lys Ala Ile Leu Ala Leu Leu Ser Val Trp Val Leu Ser Thr Val
160             165                 170                 175

ATC TCC ATC GGG CCT CTC CTT GGG TGG AAG GAG CCG GCA CCC AAC GAT        696
Ile Ser Ile Gly Pro Leu Leu Gly Trp Lys Glu Pro Ala Pro Asn Asp
                180                 185                 190

GAC AAG GAG TGC GGG GTC ACC GAA GAA CCC TTC TAT GCC CTC TTC TCC        744
Asp Lys Glu Cys Gly Val Thr Glu Glu Pro Phe Tyr Ala Leu Phe Ser
            195                 200                 205

TCT CTG GGC TCC TTC TAC ATC CCT CTG GCG GTC ATT CTA GTC ATG TAC        792
Ser Leu Gly Ser Phe Tyr Ile Pro Leu Ala Val Ile Leu Val Met Tyr
        210                 215                 220

TGC CGT GTC TAT ATA GTG GCC AAG AGA ACC ACC AAG AAC CTA GAG GCA        840
Cys Arg Val Tyr Ile Val Ala Lys Arg Thr Thr Lys Asn Leu Glu Ala
    225                 230                 235

GGA GTC ATG AAG GAG ATG TCC AAC TCC AAG GAG CTG ACC CTG AGG ATC        888
Gly Val Met Lys Glu Met Ser Asn Ser Lys Glu Leu Thr Leu Arg Ile
240             245                 250                 255

CAT TCC AAG AAC TTT CAC GAG GAC ACC CTT AGC AGT ACC AAG GCC AAG        936
His Ser Lys Asn Phe His Glu Asp Thr Leu Ser Ser Thr Lys Ala Lys
                260                 265                 270

GGC CAC AAC CCC AGG AGT TCC ATA GCT GTC AAA CTT TTT AAG TTC TCC        984
Gly His Asn Pro Arg Ser Ser Ile Ala Val Lys Leu Phe Lys Phe Ser
            275                 280                 285

AGG GAA AAG AAA GCA GCT AAG ACG TTG GGC ATT GTG GTC GGT ATG TTC       1032
Arg Glu Lys Lys Ala Ala Lys Thr Leu Gly Ile Val Val Gly Met Phe
        290                 295                 300

ATC TTG TGC TGG CTA CCC TTC TTC ATC GCT CTA CCG CTT GGC TCC TTG       1080
Ile Leu Cys Trp Leu Pro Phe Phe Ile Ala Leu Pro Leu Gly Ser Leu
    305                 310                 315

TTC TCC ACC CTG AAG CCC CCC GAC GCC GTG TTC AAG GTG GTG TTC TGG       1128
Phe Ser Thr Leu Lys Pro Pro Asp Ala Val Phe Lys Val Val Phe Trp
320             325                 330                 335

CTG GGC TAC TTC AAC AGC TGC CTC AAC CCC ATC ATC TAC CCA TGC TCC       1176
Leu Gly Tyr Phe Asn Ser Cys Leu Asn Pro Ile Ile Tyr Pro Cys Ser
                340                 345                 350

AGC AAG GAG TTC AAG CGC GCT TTC GTG CGC ATC CTC GGG TGC CAG TGC       1224
Ser Lys Glu Phe Lys Arg Ala Phe Val Arg Ile Leu Gly Cys Gln Cys
            355                 360                 365

CGC GGC CGC GGC CGC CGC CGA CGC CGC CGC CGC CGT CGC CTG GGC GGC       1272
Arg Gly Arg Gly Arg Arg Arg Arg Arg Arg Arg Arg Leu Gly Gly
        370                 375                 380

TGC GCC TAC ACC TAC CGG CCG TGG ACG CGC GGC GGC TCG CTG GAG CGC       1320
Cys Ala Tyr Thr Tyr Arg Pro Trp Thr Arg Gly Gly Ser Leu Glu Arg
    385                 390                 395

TCG CAG TCG CGC AAG GAC TCG CTG GAC GAC AGC GGC AGC TGC CTG AGC       1368
Ser Gln Ser Arg Lys Asp Ser Leu Asp Asp Ser Gly Ser Cys Leu Ser
400             405                 410                 415

GGC AGC CAG CGG ACC CTG CCC TCG GCC TCG CCG AGC CCG GGC TAC CTG       1416
Gly Ser Gln Arg Thr Leu Pro Ser Ala Ser Pro Ser Pro Gly Tyr Leu
                420                 425                 430

GGC CGC GGC GCG CCA CCG CCA GTC GAG CTG TGC GCC TTC CCC GAG TGG       1464
Gly Arg Gly Ala Pro Pro Pro Val Glu Leu Cys Ala Phe Pro Glu Trp
            435                 440                 445

AAG GCG CCC GGC GCC CTC CTG AGC CTG CCC GCG CCT GAG CCC CCC GGC       1512
Lys Ala Pro Gly Ala Leu Leu Ser Leu Pro Ala Pro Glu Pro Pro Gly
        450                 455                 460

CGC CGC GGC CGC CAC GAC TCG GGC CCG CTC TTC ACC TTC AAG CTC CTG       1560
Arg Arg Gly Arg His Asp Ser Gly Pro Leu Phe Thr Phe Lys Leu Leu
    465                 470                 475
```

```
ACC GAG CCC GAG AGC CCC GGG ACC GAC GGC GGC GCC AGC AAC GGA GGC      1608
Thr Glu Pro Glu Ser Pro Gly Thr Asp Gly Gly Ala Ser Asn Gly Gly
480                 485                 490                 495

TGC GAG GCC GCG GCC GAC GTG GCC AAC GGG CAG CCG GGC TTC AAA AGC      1656
Cys Glu Ala Ala Ala Asp Val Ala Asn Gly Gln Pro Gly Phe Lys Ser
                500                 505                 510

AAC ATG CCC CTG GCG CCC GGG CAG TTT TAGGGCCCCC GTGCGCAGCT            1703
Asn Met Pro Leu Ala Pro Gly Gln Phe
            515                 520

TTCTTTCCCT GGGGAGGAAA ACATCGTGGG GGGGA                               1738
```

(2) INFORMATION FOR SEQ ID NO:4:

(i) SEQUENCE CHARACTERISTICS:
        (A) LENGTH: 520 amino acids
        (B) TYPE: amino acid
        (D) TOPOLOGY: linear (ii) MOLECULE TYPE: protein (xi) SEQUENCE DESCRIPTION: SEQ ID NO:4:

```
Met Asn Pro Asp Leu Asp Thr Gly His Asn Thr Ser Ala Pro Ala His
1               5                   10                  15

Trp Gly Glu Leu Lys Asn Ala Asn Phe Thr Gly Pro Asn Gln Thr Ser
            20                  25                  30

Ser Asn Ser Thr Leu Pro Gln Leu Asp Ile Thr Arg Ala Ile Ser Val
        35                  40                  45

Gly Leu Val Leu Gly Ala Phe Ile Leu Phe Ala Ile Val Gly Asn Ile
    50                  55                  60

Leu Val Ile Leu Ser Val Ala Cys Asn Arg His Leu Arg Thr Pro Thr
65                  70                  75                  80

Asn Tyr Phe Ile Val Asn Leu Ala Met Ala Asp Leu Leu Leu Ser Phe
                85                  90                  95

Thr Val Leu Pro Phe Ser Ala Ala Leu Glu Val Leu Gly Tyr Trp Val
            100                 105                 110

Leu Gly Arg Ile Phe Cys Asp Ile Trp Ala Ala Val Asp Val Leu Cys
        115                 120                 125

Cys Thr Ala Ser Ile Leu Ser Leu Cys Ala Ile Ser Ile Asp Arg Tyr
    130                 135                 140

Ile Gly Val Arg Tyr Ser Leu Gln Tyr Pro Thr Leu Val Thr Arg Arg
145                 150                 155                 160

Lys Ala Ile Leu Ala Leu Leu Ser Val Trp Val Leu Ser Thr Val Ile
                165                 170                 175

Ser Ile Gly Pro Leu Leu Gly Trp Lys Glu Pro Ala Pro Asn Asp Asp
            180                 185                 190

Lys Glu Cys Gly Val Thr Glu Glu Pro Phe Tyr Ala Leu Phe Ser Ser
        195                 200                 205

Leu Gly Ser Phe Tyr Ile Pro Leu Ala Val Ile Leu Val Met Tyr Cys
    210                 215                 220

Arg Val Tyr Ile Val Ala Lys Arg Thr Thr Lys Asn Leu Glu Ala Gly
225                 230                 235                 240

Val Met Lys Glu Met Ser Asn Ser Lys Glu Leu Thr Leu Arg Ile His
                245                 250                 255

Ser Lys Asn Phe His Glu Asp Thr Leu Ser Ser Thr Lys Ala Lys Gly
            260                 265                 270

His Asn Pro Arg Ser Ser Ile Ala Val Lys Leu Phe Lys Phe Ser Arg
        275                 280                 285
```

```
Glu Lys Lys Ala Ala Lys Thr Leu Gly Ile Val Val Gly Met Phe Ile
    290                 295                 300

Leu Cys Trp Leu Pro Phe Phe Ile Ala Leu Pro Leu Gly Ser Leu Phe
305                 310                 315                 320

Ser Thr Leu Lys Pro Pro Asp Ala Val Phe Lys Val Val Phe Trp Leu
                325                 330                 335

Gly Tyr Phe Asn Ser Cys Leu Asn Pro Ile Ile Tyr Pro Cys Ser Ser
                340                 345                 350

Lys Glu Phe Lys Arg Ala Phe Val Arg Ile Leu Gly Cys Gln Cys Arg
                355                 360                 365

Gly Arg Gly Arg Arg Arg Arg Arg Arg Arg Arg Leu Gly Gly Cys
370                 375                 380

Ala Tyr Thr Tyr Arg Pro Trp Thr Arg Gly Gly Ser Leu Glu Arg Ser
385                 390                 395                 400

Gln Ser Arg Lys Asp Ser Leu Asp Asp Ser Gly Ser Cys Leu Ser Gly
                405                 410                 415

Ser Gln Arg Thr Leu Pro Ser Ala Ser Pro Ser Pro Gly Tyr Leu Gly
                420                 425                 430

Arg Gly Ala Pro Pro Val Glu Leu Cys Ala Phe Pro Glu Trp Lys
                435                 440                 445

Ala Pro Gly Ala Leu Leu Ser Leu Pro Ala Pro Glu Pro Pro Gly Arg
450                 455                 460

Arg Gly Arg His Asp Ser Gly Pro Leu Phe Thr Phe Lys Leu Leu Thr
465                 470                 475                 480

Glu Pro Glu Ser Pro Gly Thr Asp Gly Gly Ala Ser Asn Gly Gly Cys
                485                 490                 495

Glu Ala Ala Ala Asp Val Ala Asn Gly Gln Pro Gly Phe Lys Ser Asn
                500                 505                 510

Met Pro Leu Ala Pro Gly Gln Phe
                515                 520

(2) INFORMATION FOR SEQ ID NO:5:

(i) SEQUENCE CHARACTERISTICS:
        (A) LENGTH: 1639 base pairs
        (B) TYPE: nucleic acid
        (C) STRANDEDNESS: single
        (D) TOPOLOGY: unknown (ii) MOLECULE TYPE: DNA (genomic)

(iii) HYPOTHETICAL: N (iv) ANTI-SENSE: N (ix) FEATURE:
        (A) NAME/KEY: CDS
        (B) LOCATION: 126..1523
        (D) OTHER INFORMATION:

(xi) SEQUENCE DESCRIPTION: SEQ ID NO:5:

CCAGCCAAAC CACTGGCAGG CTCCCTCCAG CCGAGACCTT TTATTCCCGG CTCCCGAGCT        60

CCGCCTCCGC GCCAGCCCGG GAGGTGGCCC TGACAGCCGG ACCTCGCCCG GCCCCGGCTG       120

GGACC ATG GTG TTT CTC TCG GGA AAT GCT TCC GAC AGC TCC AAC TGC           167
      Met Val Phe Leu Ser Gly Asn Ala Ser Asp Ser Ser Asn Cys
        1               5                   10

ACC CAA CCG CCG GCA CCG GTG AAC ATT TCC AAG GCC ATT CTG CTC GGG         215
Thr Gln Pro Pro Ala Pro Val Asn Ile Ser Lys Ala Ile Leu Leu Gly
 15                  20                  25                  30
```

| | | | | | | | | | | | | | | | |
|---|---|---|---|---|---|---|---|---|---|---|---|---|---|---|---|
| GTG | ATC | TTG | GGG | GGC | CTC | ATT | CTT | TTC | GGG | GTG | CTG | GGT | AAC | ATC | CTA | 263 |
| Val | Ile | Leu | Gly | Gly | Leu | Ile | Leu | Phe | Gly | Val | Leu | Gly | Asn | Ile | Leu | |
| | | | 35 | | | | | 40 | | | | | 45 | | | |

| | | | | | | | | | | | | | | | |
|---|---|---|---|---|---|---|---|---|---|---|---|---|---|---|---|
| GTG | ATC | CTC | TCC | GTA | GCC | TGT | CAC | CGA | CAC | CTG | CAC | TCA | GTC | ACG | CAC | 311 |
| Val | Ile | Leu | Ser | Val | Ala | Cys | His | Arg | His | Leu | His | Ser | Val | Thr | His | |
| | | | 50 | | | | 55 | | | | | 60 | | | | |

| | | | | | | | | | | | | | | | |
|---|---|---|---|---|---|---|---|---|---|---|---|---|---|---|---|
| TAC | TAC | ATC | GTC | AAC | CTG | GCG | GTG | GCC | GAC | CTC | CTG | CTC | ACC | TCC | ACG | 359 |
| Tyr | Tyr | Ile | Val | Asn | Leu | Ala | Val | Ala | Asp | Leu | Leu | Leu | Thr | Ser | Thr | |
| | | | 65 | | | | 70 | | | | | 75 | | | | |

| | | | | | | | | | | | | | | | |
|---|---|---|---|---|---|---|---|---|---|---|---|---|---|---|---|
| GTG | CTG | CCC | TTC | TCC | GCC | ATC | TTC | GAG | GTC | CTA | GGC | TAC | TGG | GCC | TTC | 407 |
| Val | Leu | Pro | Phe | Ser | Ala | Ile | Phe | Glu | Val | Leu | Gly | Tyr | Trp | Ala | Phe | |
| | | 80 | | | | | 85 | | | | | 90 | | | | |

| | | | | | | | | | | | | | | | |
|---|---|---|---|---|---|---|---|---|---|---|---|---|---|---|---|
| GGC | AGG | GTC | TTC | TGC | AAC | ATC | TGG | GCG | GCA | GTG | GAT | GTG | CTG | TGC | TGC | 455 |
| Gly | Arg | Val | Phe | Cys | Asn | Ile | Trp | Ala | Ala | Val | Asp | Val | Leu | Cys | Cys | |
| 95 | | | | | 100 | | | | | 105 | | | | | 110 | |

| | | | | | | | | | | | | | | | |
|---|---|---|---|---|---|---|---|---|---|---|---|---|---|---|---|
| ACC | GCG | TCC | ATC | ATG | GGC | CTC | TGC | ATC | ATC | TCC | ATC | GAC | CGC | TAC | ATC | 503 |
| Thr | Ala | Ser | Ile | Met | Gly | Leu | Cys | Ile | Ile | Ser | Ile | Asp | Arg | Tyr | Ile | |
| | | | | 115 | | | | | 120 | | | | | 125 | | |

| | | | | | | | | | | | | | | | |
|---|---|---|---|---|---|---|---|---|---|---|---|---|---|---|---|
| GGC | GTG | AGC | TAC | CCG | CTG | CGC | TAC | CCA | ACC | ATC | GTC | ACC | CAG | AGG | AGG | 551 |
| Gly | Val | Ser | Tyr | Pro | Leu | Arg | Tyr | Pro | Thr | Ile | Val | Thr | Gln | Arg | Arg | |
| | | | 130 | | | | | 135 | | | | | 140 | | | |

| | | | | | | | | | | | | | | | |
|---|---|---|---|---|---|---|---|---|---|---|---|---|---|---|---|
| GGT | CTC | ATG | GCT | CTG | CTC | TGC | GTC | TGG | GCA | CTC | TCC | CTG | GTC | ATA | TCC | 599 |
| Gly | Leu | Met | Ala | Leu | Leu | Cys | Val | Trp | Ala | Leu | Ser | Leu | Val | Ile | Ser | |
| | | | 145 | | | | | 150 | | | | | 155 | | | |

| | | | | | | | | | | | | | | | |
|---|---|---|---|---|---|---|---|---|---|---|---|---|---|---|---|
| ATT | GGA | CCC | CTG | TTC | GGC | TGG | AGG | CAG | CCG | GCC | CCC | GAG | GAC | GAG | ACC | 647 |
| Ile | Gly | Pro | Leu | Phe | Gly | Trp | Arg | Gln | Pro | Ala | Pro | Glu | Asp | Glu | Thr | |
| | 160 | | | | | 165 | | | | | 170 | | | | | |

| | | | | | | | | | | | | | | | |
|---|---|---|---|---|---|---|---|---|---|---|---|---|---|---|---|
| ATC | TGC | CAG | ATC | AAC | GAG | GAG | CCG | GGC | TAC | GTG | CTC | TTC | TCA | GCG | CTG | 695 |
| Ile | Cys | Gln | Ile | Asn | Glu | Glu | Pro | Gly | Tyr | Val | Leu | Phe | Ser | Ala | Leu | |
| 175 | | | | | 180 | | | | | 185 | | | | | 190 | |

| | | | | | | | | | | | | | | | |
|---|---|---|---|---|---|---|---|---|---|---|---|---|---|---|---|
| GGC | TCC | TTC | TAC | CTG | CCT | CTG | GCC | ATC | ATC | CTG | GTC | ATG | TAC | TGC | CGC | 743 |
| Gly | Ser | Phe | Tyr | Leu | Pro | Leu | Ala | Ile | Ile | Leu | Val | Met | Tyr | Cys | Arg | |
| | | | | 195 | | | | | 200 | | | | | 205 | | |

| | | | | | | | | | | | | | | | |
|---|---|---|---|---|---|---|---|---|---|---|---|---|---|---|---|
| GTC | TAC | GTG | GTG | GCC | AAG | AGG | GAG | AGC | CGG | GGC | CTC | AAG | TCT | GGC | CTC | 791 |
| Val | Tyr | Val | Val | Ala | Lys | Arg | Glu | Ser | Arg | Gly | Leu | Lys | Ser | Gly | Leu | |
| | | | 210 | | | | | 215 | | | | | 220 | | | |

| | | | | | | | | | | | | | | | |
|---|---|---|---|---|---|---|---|---|---|---|---|---|---|---|---|
| AAG | ACC | GAC | AAG | TCG | GAC | TCG | GAG | CAA | GTG | ACG | CTC | CGC | ATC | CAT | CGG | 839 |
| Lys | Thr | Asp | Lys | Ser | Asp | Ser | Glu | Gln | Val | Thr | Leu | Arg | Ile | His | Arg | |
| | | | 225 | | | | | 230 | | | | | 235 | | | |

| | | | | | | | | | | | | | | | |
|---|---|---|---|---|---|---|---|---|---|---|---|---|---|---|---|
| AAA | AAC | GCC | CCG | GCA | GGA | GGC | AGC | GGG | ATG | GCC | AGC | GCC | AAG | ACC | AAG | 887 |
| Lys | Asn | Ala | Pro | Ala | Gly | Gly | Ser | Gly | Met | Ala | Ser | Ala | Lys | Thr | Lys | |
| | 240 | | | | | 245 | | | | | 250 | | | | | |

| | | | | | | | | | | | | | | | |
|---|---|---|---|---|---|---|---|---|---|---|---|---|---|---|---|
| ACG | CAC | TTC | TCA | GTG | AGG | CTC | CTC | AAG | TTC | TCC | CGG | GAG | AAG | AAA | GCG | 935 |
| Thr | His | Phe | Ser | Val | Arg | Leu | Leu | Lys | Phe | Ser | Arg | Glu | Lys | Lys | Ala | |
| 255 | | | | | 260 | | | | | 265 | | | | | 270 | |

| | | | | | | | | | | | | | | | |
|---|---|---|---|---|---|---|---|---|---|---|---|---|---|---|---|
| GCC | AAA | ACG | CTG | GGC | ATC | GTG | GTC | GGC | TGC | TTC | GTC | CTC | TGC | TGG | CTG | 983 |
| Ala | Lys | Thr | Leu | Gly | Ile | Val | Val | Gly | Cys | Phe | Val | Leu | Cys | Trp | Leu | |
| | | | | 275 | | | | | 280 | | | | | 285 | | |

| | | | | | | | | | | | | | | | |
|---|---|---|---|---|---|---|---|---|---|---|---|---|---|---|---|
| CCT | TTT | TTC | TTA | GTC | ATG | CCC | ATT | GGG | TCT | TTC | TTC | CCT | GAT | TTC | AAG | 1031 |
| Pro | Phe | Phe | Leu | Val | Met | Pro | Ile | Gly | Ser | Phe | Phe | Pro | Asp | Phe | Lys | |
| | | | 290 | | | | | 295 | | | | | 300 | | | |

| | | | | | | | | | | | | | | | |
|---|---|---|---|---|---|---|---|---|---|---|---|---|---|---|---|
| CCC | TCT | GAA | ACA | GTT | TTT | AAA | ATA | GTA | TTT | TGG | CTC | GGA | TAT | CTA | AAC | 1079 |
| Pro | Ser | Glu | Thr | Val | Phe | Lys | Ile | Val | Phe | Trp | Leu | Gly | Tyr | Leu | Asn | |
| | | 305 | | | | | 310 | | | | | 315 | | | | |

| | | | | | | | | | | | | | | | |
|---|---|---|---|---|---|---|---|---|---|---|---|---|---|---|---|
| AGC | TGC | ATC | AAC | CCC | ATC | ATA | TAC | CCA | TGC | TCC | AGC | CAA | GAG | TTC | AAA | 1127 |
| Ser | Cys | Ile | Asn | Pro | Ile | Ile | Tyr | Pro | Cys | Ser | Ser | Gln | Glu | Phe | Lys | |
| | | 320 | | | | | 325 | | | | | 330 | | | | |

| | | | | | | | | | | | | | | | |
|---|---|---|---|---|---|---|---|---|---|---|---|---|---|---|---|
| AAG | GCC | TTT | CAG | AAT | GTC | TTG | AGA | ATC | CAG | TGT | CTC | TGC | AGA | AAG | CAG | 1175 |
| Lys | Ala | Phe | Gln | Asn | Val | Leu | Arg | Ile | Gln | Cys | Leu | Cys | Arg | Lys | Gln | |
| 335 | | | | | 340 | | | | | 345 | | | | | 350 | |

-continued

```
TCT TCC AAA CAT GCC CTG GGC TAC ACC CTG CAC CCG CCC AGC CAG GCC    1223
Ser Ser Lys His Ala Leu Gly Tyr Thr Leu His Pro Pro Ser Gln Ala
            355                 360                 365

GTG GAA GGG CAA CAC AAG GAC ATG GTG CGC ATC CCC GTG GGA TCA AGA    1271
Val Glu Gly Gln His Lys Asp Met Val Arg Ile Pro Val Gly Ser Arg
        370                 375                 380

GAG ACC TTC TAC AGG ATC TCC AAG ACG GAT GGC GTT TGT GAA TGG AAA    1319
Glu Thr Phe Tyr Arg Ile Ser Lys Thr Asp Gly Val Cys Glu Trp Lys
        385                 390                 395

TTT TTC TCT TCC ATG CCC CGT GGA TCT GCC AGG ATT ACA GTG TCC AAA    1367
Phe Phe Ser Ser Met Pro Arg Gly Ser Ala Arg Ile Thr Val Ser Lys
400                 405                 410

GAC CAA TCC TCC TGT ACC ACA GCC CGG GTG AGA AGT AAA AGC TTT TTG    1415
Asp Gln Ser Ser Cys Thr Thr Ala Arg Val Arg Ser Lys Ser Phe Leu
415                 420                 425                 430

CAG GTC TGC TGC TGT GTA GGG CCC TCA ACC CCC AGC CTT GAC AAG AAC    1463
Gln Val Cys Cys Cys Val Gly Pro Ser Thr Pro Ser Leu Asp Lys Asn
                435                 440                 445

CAT CAA GTT CCA ACC ATT AAG GTC CAC ACC ATC TCC CTC AGT GAG AAC    1511
His Gln Val Pro Thr Ile Lys Val His Thr Ile Ser Leu Ser Glu Asn
        450                 455                 460

GGG GAG GAA GTC TAGGACAGGA AAGATGCAGA GGAAAGGGGA ATATCTTAGG        1563
Gly Glu Glu Val
            465

TACCATACCC TGGAGTTCTA GAGGATTCCT CGACAAGCTT ATTCCGATCC AGACATGATA  1623

GATACATTGA TGAGTT                                                  1639
```

(2) INFORMATION FOR SEQ ID NO:6:

(i) SEQUENCE CHARACTERISTICS:
        (A) LENGTH: 466 amino acids
        (B) TYPE: amino acid
        (D) TOPOLOGY: linear (ii) MOLECULE TYPE: protein (xi) SEQUENCE DESCRIPTION: SEQ ID NO:6:

```
Met Val Phe Leu Ser Gly Asn Ala Ser Asp Ser Ser Asn Cys Thr Gln
  1               5                  10                  15

Pro Pro Ala Pro Val Asn Ile Ser Lys Ala Ile Leu Leu Gly Val Ile
                 20                  25                  30

Leu Gly Gly Leu Ile Leu Phe Gly Val Leu Gly Asn Ile Leu Val Ile
             35                  40                  45

Leu Ser Val Ala Cys His Arg His Leu His Ser Val Thr His Tyr Tyr
 50                  55                  60

Ile Val Asn Leu Ala Val Ala Asp Leu Leu Leu Thr Ser Thr Val Leu
 65                  70                  75                  80

Pro Phe Ser Ala Ile Phe Glu Val Leu Gly Tyr Trp Ala Phe Gly Arg
                 85                  90                  95

Val Phe Cys Asn Ile Trp Ala Ala Val Asp Val Leu Cys Cys Thr Ala
                100                 105                 110

Ser Ile Met Gly Leu Cys Ile Ile Ser Ile Asp Arg Tyr Ile Gly Val
            115                 120                 125

Ser Tyr Pro Leu Arg Tyr Pro Thr Ile Val Thr Gln Arg Arg Gly Leu
        130                 135                 140

Met Ala Leu Leu Cys Val Trp Ala Leu Ser Leu Val Ile Ser Ile Gly
145                 150                 155                 160

Pro Leu Phe Gly Trp Arg Gln Pro Ala Pro Glu Asp Glu Thr Ile Cys
                165                 170                 175
```

Gln Ile Asn Glu Glu Pro Gly Tyr Val Leu Phe Ser Ala Leu Gly Ser
            180                 185                 190

Phe Tyr Leu Pro Leu Ala Ile Ile Leu Val Met Tyr Cys Arg Val Tyr
        195                 200                 205

Val Val Ala Lys Arg Glu Ser Arg Gly Leu Lys Ser Gly Leu Lys Thr
210                 215                 220

Asp Lys Ser Asp Ser Glu Gln Val Thr Leu Arg Ile His Arg Lys Asn
225                 230                 235                 240

Ala Pro Ala Gly Gly Ser Gly Met Ala Ser Ala Lys Thr Lys Thr His
            245                 250                 255

Phe Ser Val Arg Leu Leu Lys Phe Ser Arg Glu Lys Lys Ala Ala Lys
        260                 265                 270

Thr Leu Gly Ile Val Val Gly Cys Phe Val Leu Cys Trp Leu Pro Phe
        275                 280                 285

Phe Leu Val Met Pro Ile Gly Ser Phe Phe Pro Asp Phe Lys Pro Ser
    290                 295                 300

Glu Thr Val Phe Lys Ile Val Phe Trp Leu Gly Tyr Leu Asn Ser Cys
305                 310                 315                 320

Ile Asn Pro Ile Ile Tyr Pro Cys Ser Ser Gln Glu Phe Lys Lys Ala
                325                 330                 335

Phe Gln Asn Val Leu Arg Ile Gln Cys Leu Cys Arg Lys Gln Ser Ser
            340                 345                 350

Lys His Ala Leu Gly Tyr Thr Leu His Pro Pro Ser Gln Ala Val Glu
        355                 360                 365

Gly Gln His Lys Asp Met Val Arg Ile Pro Val Gly Ser Arg Glu Thr
        370                 375                 380

Phe Tyr Arg Ile Ser Lys Thr Asp Gly Val Cys Glu Trp Lys Phe Phe
385                 390                 395                 400

Ser Ser Met Pro Arg Gly Ser Ala Arg Ile Thr Val Ser Lys Asp Gln
                405                 410                 415

Ser Ser Cys Thr Thr Ala Arg Val Arg Ser Lys Ser Phe Leu Gln Val
            420                 425                 430

Cys Cys Cys Val Gly Pro Ser Thr Pro Ser Leu Asp Lys Asn His Gln
            435                 440                 445

Val Pro Thr Ile Lys Val His Thr Ile Ser Leu Ser Glu Asn Gly Glu
        450                 455                 460

Glu Val
465

(2) INFORMATION FOR SEQ ID NO:7:

(i) SEQUENCE CHARACTERISTICS:
(A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

CACTCAAGTA CCCAGCCATC ATGAC                                             25

(2) INFORMATION FOR SEQ ID NO:8:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

CGGAGAGCGA GCTGCGGAAG GTGTG                                              25

(2) INFORMATION FOR SEQ ID NO:9:

(i) SEQUENCE CHARACTERISTICS:
            (A) LENGTH: 45 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:9:

GCAAGGCCTC CGAGGTGGTG CTGCGCATCC ACTGTCGCGG CGCGG                        45

(2) INFORMATION FOR SEQ ID NO:10:

(i) SEQUENCE CHARACTERISTICS:
            (A) LENGTH: 47 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:10:

TGCCGTGCGC CCCGTCGGCG CCCGTGGCCG CGCCGCGACA GTGGATG                      47

(2) INFORMATION FOR SEQ ID NO:11:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:11:

CAACGATGAC AAGGAGTGCG GGGTCAC                                            27

(2) INFORMATION FOR SEQ ID NO:12:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:12:

TTTGACAGCT ATGGAACTCC TGGGG                                              25

(2) INFORMATION FOR SEQ ID NO:13:

(i) SEQUENCE CHARACTERISTICS:
            (A) LENGTH: 45 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:13:

AAGGAGCTGA CCCTGAGGAT CCATTCCAAG AACTTTCACG AGGAC                        45

(2) INFORMATION FOR SEQ ID NO:14:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

CCTTGGCCTT GGTACTGCTA AGGGTGTCCT CGTGAAAGTT CTTGG          45

(2) INFORMATION FOR SEQ ID NO:15:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

CCAACCATCG TCACCCAGAG GAG          23

(2) INFORMATION FOR SEQ ID NO:16:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

TCTCCCGGGA GAACTTGAGG AGCCTCAC          28

(2) INFORMATION FOR SEQ ID NO:17:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

TCCGCATCCA TCGGAAAAAC GCCCCGGCAG GAGGCAGCGG GATGG          45

(2) INFORMATION FOR SEQ ID NO:18:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:18:

GAAGTGCGTC TTGGTCTTGG CGCTGGCCAT CCCGCTGCCT CCTGCC          46

(2) INFORMATION FOR SEQ ID NO:19:

(i) SEQUENCE CHARACTERISTICS:
        (A) LENGTH: 521 amino acids
        (B) TYPE: amino acid (C) STRANDEDNESS: single
(D) TOPOLOGY: linear (ii) MOLECULE TYPE: protein (xi) SEQUENCE DESCRIPTION: SEQ ID NO:19:

Met Ala Ala Ala Leu Arg Ser Val Met Met Ala Gly Tyr Leu Ser Glu
1               5                  10                  15

Trp Arg Thr Pro Thr Tyr Arg Ser Thr Glu Met Val Gln Arg Leu Arg
            20                  25                  30

Met Glu Ala Val Gln His Ser Thr Ser Thr Ala Ala Val Gly Gly Leu
        35                  40                  45

Val Val Ser Ala Gln Gly Val Gly Val Gly Val Phe Leu Ala Ala Phe
    50                  55                  60

Ile Leu Thr Ala Val Ala Gly Asn Leu Leu Val Ile Leu Ser Val Ala
65                  70                  75                  80

Cys Asn Arg His Leu Gln Thr Val Thr Asn Tyr Phe Ile Val Asn Leu
                85                  90                  95

Ala Val Ala Asp Leu Leu Leu Ser Ala Ala Val Leu Pro Phe Ser Ala
                100                 105                 110

Thr Met Glu Val Leu Gly Phe Trp Ala Phe Gly Arg Thr Phe Cys Asp
            115                 120                 125

Val Trp Ala Ala Val Asp Val Leu Cys Cys Thr Ala Ser Ile Leu Ser
    130                 135                 140

Leu Cys Thr Ile Ser Val Asp Arg Tyr Val Gly Val Arg His Ser Leu
145                 150                 155                 160

Lys Tyr Pro Ala Ile Met Thr Glu Arg Lys Ala Ala Ile Leu Ala
                165                 170                 175

Leu Leu Trp Ala Val Ala Leu Val Val Ser Val Gly Pro Leu Leu Gly
            180                 185                 190

Trp Lys Glu Pro Val Pro Pro Asp Glu Arg Phe Cys Gly Ile Thr Glu
        195                 200                 205

Glu Val Gly Tyr Ala Ile Phe Ser Ser Val Cys Ser Phe Tyr Leu Pro
    210                 215                 220

Met Ala Val Ile Val Val Met Tyr Cys Arg Val Tyr Val Val Ala Arg
225                 230                 235                 240

Ser Thr Thr Arg Ser Leu Glu Ala Gly Ile Lys Arg Glu Pro Gly Lys
                245                 250                 255

Ala Ser Glu Val Val Leu Arg Ile His Cys Arg Gly Ala Ala Thr Ser
            260                 265                 270

Ala Asp Gly Ala His Gly Met Arg Ser Ala Lys Gly His Thr Phe Arg
        275                 280                 285

Ser Ser Leu Ser Val Arg Leu Leu Lys Phe Ser Arg Glu Lys Lys Ala
    290                 295                 300

Ala Lys Thr Leu Ala Ile Val Val Gly Val Phe Val Leu Cys Trp Phe
305                 310                 315                 320

Pro Phe Phe Phe Val Leu Pro Leu Gly Ser Leu Phe Pro Gln Leu Lys
                325                 330                 335

Pro Ser Glu Gly Val Phe Lys Val Ile Phe Trp Leu Gly Tyr Phe Asn
            340                 345                 350

Ser Cys Val Asn Pro Leu Ile Tyr Pro Cys Ser Ser Arg Glu Phe Lys
        355                 360                 365

Arg Ala Phe Leu Arg Leu Leu Arg Cys Gln Cys Arg Arg Arg Arg Arg
    370                 375                 380

-continued

```
Arg Arg Pro Leu Trp Arg Val Tyr Gly His His Trp Arg Ala Ser Thr
385                 390                 395                 400

Ser Gly Leu Arg Gln Asp Cys Ala Pro Ser Ser Gly Asp Ala Pro Pro
            405                 410                 415

Gly Ala Pro Ala Leu Thr Ala Leu Pro Asp Pro Asp Pro Glu Pro Pro
            420                 425                 430

Gly Thr Pro Glu Met Gln Ala Pro Val Ala Ser Arg Arg Ser His Pro
            435                 440                 445

Ala Pro Ser Ala Ser Gly Gly Cys Gln Gly Arg Ser Gly Asp Pro Arg
450                 455                 460

Pro Ser Cys Ala Pro Lys Ser Pro Ala Cys Arg Thr Arg Ser Pro Pro
465                 470                 475                 480

Gly Ala Arg Ser Ala Gln Arg Gln Arg Ala Pro Ser Ala Gln Arg Trp
            485                 490                 495

Arg Leu Cys Pro Ser Leu Val Pro Ala Glu Cys Gln Ala Tyr Glu Asp
            500                 505                 510

Tyr Ser Asn Leu Arg Glu Thr Asp Ile
            515                 520

(2) INFORMATION FOR SEQ ID NO:20:

(i) SEQUENCE CHARACTERISTICS:
        (A) LENGTH: 559 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:20:

Met Thr Phe Arg Asp Ile Leu Ser Val Thr Phe Glu Gly Pro Arg Ser
1               5                   10                  15

Ser Ser Ser Thr Gly Gly Ser Gly Ala Gly Gly Ala Gly Thr Val
            20                  25                  30

Gly Pro Glu Gly Gly Ala Val Gly Val Pro Gly Ala Thr Gly Gly
            35                  40                  45

Gly Ala Val Val Gly Thr Gly Ser Gly Glu Asp Asn Gln Ser Ser Thr
50                  55                  60

Gly Glu Pro Gly Ala Ala Ala Ser Gly Glu Val Asn Gly Ser Ala Ala
65                  70                  75                  80

Val Gly Gly Leu Val Val Ser Ala Gln Gly Val Gly Val Gly Val Phe
            85                  90                  95

Leu Ala Ala Phe Ile Leu Thr Ala Val Ala Gly Asn Leu Leu Val Ile
            100                 105                 110

Leu Ser Val Ala Cys Asn Arg His Leu Gln Thr Val Thr Asn Tyr Phe
            115                 120                 125

Ile Val Asn Leu Ala Val Ala Asp Leu Leu Leu Ser Ala Ala Val Leu
            130                 135                 140

Pro Phe Ser Ala Thr Met Glu Val Leu Gly Phe Trp Ala Phe Gly Arg
145                 150                 155                 160

Thr Phe Cys Asp Val Trp Ala Ala Val Asp Val Leu Cys Cys Thr Ala
            165                 170                 175

Ser Ile Leu Ser Leu Cys Thr Ile Ser Val Asp Arg Tyr Val Gly Val
            180                 185                 190

Arg His Ser Leu Lys Tyr Pro Ala Ile Met Thr Glu Arg Lys Ala Ala
            195                 200                 205
```

```
Ala Ile Leu Ala Leu Leu Trp Ala Val Ala Leu Val Val Ser Val Gly
    210                 215                 220

Pro Leu Leu Gly Trp Lys Glu Pro Val Pro Pro Asp Glu Arg Phe Cys
225                 230                 235                 240

Gly Ile Thr Glu Glu Val Gly Tyr Ala Ile Phe Ser Ser Val Cys Ser
                    245                 250                 255

Phe Tyr Leu Pro Met Ala Val Ile Val Val Met Tyr Cys Arg Val Tyr
                260                 265                 270

Val Val Ala Arg Ser Thr Thr Arg Ser Leu Glu Ala Gly Ile Lys Arg
            275                 280                 285

Glu Pro Gly Lys Ala Ser Val Val Leu Arg Ile His Cys Arg Gly Ala
        290                 295                 300

Thr Thr Ser Ala Lys Gly Tyr Pro Gly Thr Gln Ser Ser Lys Gly His
305                 310                 315                 320

Thr Leu Arg Ser Ser Leu Ser Val Arg Leu Leu Lys Phe Ser Arg Glu
                325                 330                 335

Lys Lys Ala Ala Lys Thr Leu Ala Ile Val Val Gly Val Phe Val Leu
                340                 345                 350

Cys Trp Phe Pro Phe Phe Phe Val Leu Pro Leu Gly Ser Leu Phe Pro
            355                 360                 365

Gln Leu Lys Pro Ser Glu Gly Val Phe Lys Val Ile Phe Trp Leu Gly
370                 375                 380

Tyr Phe Asn Ser Cys Val Asn Pro Leu Ile Tyr Pro Cys Ser Ser Arg
385                 390                 395                 400

Glu Phe Lys Arg Ala Phe Leu Arg Leu Leu Arg Cys Gln Cys Arg Arg
                405                 410                 415

Arg Arg Arg Arg Leu Trp Ser Leu Arg Pro Pro Leu Ala Ser Leu Asp
            420                 425                 430

Arg Arg Arg Ala Phe Arg Leu Arg Pro Gln Pro Ser His Arg Ser Pro
            435                 440                 445

Arg Gly Pro Ser Ser Pro His Cys Thr Pro Gly Cys Gly Leu Gly Arg
    450                 455                 460

His Ala Gly Asp Ala Gly Phe Gly Leu Gln Gln Ser Lys Ala Ser Leu
465                 470                 475                 480

Arg Leu Arg Glu Trp Arg Leu Leu Gly Pro Leu Gln Arg Pro Thr Thr
                485                 490                 495

Gln Leu Arg Ala Lys Val Ser Ser Leu Ser His Lys Ile Arg Ser Gly
                500                 505                 510

Ala Arg Arg Ala Glu Thr Ala Cys Ala Leu Arg Ser Glu Val Glu Ala
            515                 520                 525

Val Ser Leu Asn Val Pro Gln Asp Gly Ala Glu Ala Val Ile Cys Gln
530                 535                 540

Ala Tyr Glu Pro Gly Asp Tyr Ser Asn Leu Arg Glu Thr Asp Ile
545                 550                 555

(2) INFORMATION FOR SEQ ID NO:21:

(i) SEQUENCE CHARACTERISTICS:
        (A) LENGTH: 513 amino acids
        (B) TYPE: amino acid
        (C) STRANDEDNESS: single
        (D) TOPOLOGY: linear (ii) MOLECULE TYPE: protein
```

(xi) SEQUENCE DESCRIPTION: SEQ ID NO:21

```
Met Asn Pro Asp Leu Asp Thr Gly His Asn Thr Ser Ala Pro Ala His
  1               5                  10                  15

Trp Gly Glu Leu Lys Asp Asp Asn Phe Thr Gly Pro Asn Gln Thr Ser
                 20                  25                  30

Ser Asn Ser Thr Leu Pro Gln Leu Asp Val Thr Arg Ala Ile Ser Val
             35                  40                  45

Gly Leu Val Leu Gly Ala Phe Ile Leu Phe Ala Ile Val Gly Asn Ile
 50                      55                  60

Leu Val Ile Leu Ser Val Ala Cys Asn Arg His Leu Arg Thr Pro Thr
 65                  70                  75                  80

Asn Tyr Phe Ile Val Asn Leu Ala Ile Ala Asp Leu Leu Leu Ser Phe
                     85                  90                  95

Thr Val Leu Pro Phe Ser Ala Thr Leu Glu Val Leu Gly Tyr Trp Val
             100                 105                 110

Leu Gly Arg Ile Phe Cys Asp Ile Trp Ala Ala Val Asp Val Leu Cys
             115                 120                 125

Cys Thr Ala Ser Ile Leu Ser Leu Cys Ala Ile Ser Ile Asp Arg Tyr
130                 135                 140

Ile Gly Val Arg Tyr Ser Leu Gln Tyr Pro Thr Leu Val Thr Arg Arg
145                 150                 155                 160

Lys Ala Ile Leu Ala Leu Leu Ser Val Trp Val Leu Ser Thr Val Ile
                 165                 170                 175

Ser Ile Gly Pro Leu Leu Gly Trp Lys Glu Pro Ala Pro Asn Asp Asp
             180                 185                 190

Lys Glu Cys Gly Val Thr Glu Glu Pro Phe Cys Ala Leu Phe Cys Ser
             195                 200                 205

Leu Gly Ser Phe Tyr Ile Pro Leu Ala Val Ile Leu Val Met Tyr Cys
210                 215                 220

Arg Val Tyr Ile Val Ala Lys Arg Thr Thr Lys Asn Leu Glu Ala Gly
225                 230                 235                 240

Val Met Lys Glu Met Ser Asn Ser Lys Glu Leu Thr Leu Thr Ile His
                 245                 250                 255

Ser Lys Asn Phe His Glu Asp Thr Leu Ser Ser Thr Lys Ala Lys Gly
             260                 265                 270

His Asn Pro Arg Ser Ser Ile Ala Val Lys Leu Phe Lys Phe Ser Arg
             275                 280                 285

Glu Lys Lys Ala Ala Lys Thr Leu Gly Ile Val Val Gly Met Phe Ile
290                 295                 300

Leu Cys Trp Leu Pro Phe Phe Ile Ala Leu Pro Leu Gly Ser Leu Phe
305                 310                 315                 320

Ser Thr Leu Lys Pro Pro Asp Ala Val Phe Lys Val Val Phe Trp Leu
                 325                 330                 335

Gly Tyr Phe Asn Ser Cys Leu Asn Pro Ile Ile Tyr Pro Cys Ser Ser
             340                 345                 350

Lys Glu Phe Lys Arg Ala Phe Met Arg Ile Leu Gly Cys Gln Cys Arg
             355                 360                 365

Arg Arg Arg Arg Arg Arg Arg Leu Gly Ala Cys Ala Tyr Thr Tyr
370                 375                 380

Arg Pro Trp Thr Arg Gly Gly Ser Leu Glu Arg Ser Gln Ser Arg Lys
385                 390                 395                 400

Asp Ser Leu Asp Asp Ser Gly Ser Cys Met Ser Gly Gln Lys Arg Thr
                 405                 410                 415
```

```
Leu Pro Ser Ala Ser Pro Ser Pro Gly Tyr Leu Gly Arg Gly Thr Gln
        420                 425                 430

Pro Pro Val Glu Leu Cys Ala Phe Pro Glu Trp Lys Pro Gly Ala Leu
        435                 440                 445

Leu Ser Leu Pro Glu Pro Pro Gly Arg Arg Gly Arg Leu Asp Ser Gly
450                 455                 460

Pro Leu Phe Thr Phe Lys Leu Leu Gly Asp Pro Glu Ser Pro Gly Thr
465                 470                 475                 480

Glu Ala Thr Ala Ser Asn Gly Gly Cys Asp Thr Thr Asp Leu Ala
        485                 490                 495

Asn Gly Gln Pro Gly Phe Lys Ser Asn Met Pro Leu Gly Pro Gly His
        500                 505                 510

Phe (2) INFORMATION FOR SEQ ID NO:22

(i) SEQUENCE CHARACTERISTICS:
        (A) LENGTH: 515 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:22

Met Asn Pro Asp Leu Asp Thr Gly His Asn Thr Ser Ala Pro Ala Gln
1               5                   10                  15

Trp Gly Glu Leu Lys Asp Ala Asn Phe Thr Gly Pro Asn Gln Thr Ser
        20                  25                  30

Ser Asn Ser Thr Leu Pro Gln Leu Asp Val Thr Arg Ala Ile Ser Val
        35                  40                  45

Gly Leu Val Leu Gly Ala Phe Ile Leu Phe Ala Ile Val Gly Asn Ile
50                  55                  60

Leu Val Ile Leu Ser Val Ala Cys Asn Arg His Leu Arg Thr Pro Thr
65                  70                  75                  80

Asn Tyr Phe Ile Val Asn Leu Ala Ile Ala Asp Leu Leu Leu Ser Phe
            85                  90                  95

Thr Val Leu Pro Phe Ser Ala Thr Leu Glu Val Leu Gly Tyr Trp Val
            100                 105                 110

Leu Gly Arg Ile Phe Cys Asp Ile Trp Ala Ala Val Asp Val Leu Cys
            115                 120                 125

Cys Thr Ala Ser Ile Leu Ser Leu Cys Ala Ile Ser Ile Asp Arg Tyr
130                 135                 140

Ile Gly Val Arg Tyr Ser Leu Gln Tyr Pro Thr Leu Val Thr Arg Arg
145                 150                 155                 160

Lys Ala Ile Leu Ala Leu Leu Ser Val Trp Val Leu Ser Thr Val Ile
            165                 170                 175

Ser Ile Gly Pro Leu Leu Gly Trp Lys Glu Pro Ala Pro Asn Asp Asp
            180                 185                 190

Lys Glu Cys Gly Val Thr Glu Glu Pro Phe Tyr Ala Leu Phe Ser Ser
            195                 200                 205

Leu Gly Ser Phe Tyr Ile Pro Leu Ala Val Ile Leu Val Met Tyr Cys
            210                 215                 220

Arg Val Tyr Ile Val Ala Lys Arg Thr Thr Lys Asn Leu Glu Ala Gly
225                 230                 235                 240

Val Met Lys Glu Met Ser Asn Ser Lys Glu Leu Thr Leu Arg Ile His
            245                 250                 255
```

```
Ser Lys Asn Phe His Glu Asp Thr Leu Ser Ser Thr Lys Ala Lys Gly
            260                 265                 270

His Asn Pro Arg Ser Ser Ile Ala Val Lys Leu Phe Lys Phe Ser Arg
            275                 280                 285

Glu Lys Lys Ala Ala Lys Thr Leu Gly Ile Val Val Gly Met Phe Ile
            290                 295                 300

Leu Cys Trp Leu Pro Phe Phe Ile Ala Leu Pro Leu Gly Ser Leu Phe
305                 310                 315                 320

Ser Thr Leu Lys Pro Pro Asp Ala Val Phe Lys Val Val Phe Trp Leu
                325                 330                 335

Gly Tyr Phe Asn Ser Cys Leu Asn Pro Ile Ile Tyr Pro Cys Ser Ser
            340                 345                 350

Lys Glu Phe Lys Arg Ala Phe Met Arg Ile Leu Gly Cys Gln Cys Arg
            355                 360                 365

Ser Gly Arg Arg Arg Arg Arg Arg Arg Arg Leu Gly Ala Cys Ala Tyr
            370                 375                 380

Thr Tyr Arg Pro Trp Thr Arg Gly Gly Ser Leu Glu Arg Ser Gln Ser
385                 390                 395                 400

Arg Lys Asp Ser Leu Asp Asp Ser Gly Ser Cys Met Ser Gly Ser Gln
                405                 410                 415

Arg Thr Leu Pro Ser Ala Ser Pro Ser Pro Gly Tyr Leu Gly Arg Gly
            420                 425                 430

Ala Gln Pro Pro Leu Glu Leu Cys Ala Tyr Pro Glu Trp Lys Ser Gly
            435                 440                 445

Ala Leu Leu Ser Leu Pro Glu Pro Pro Gly Arg Arg Gly Arg Leu Asp
450                 455                 460

Ser Gly Pro Leu Phe Thr Phe Lys Leu Leu Gly Glu Pro Glu Ser Pro
465                 470                 475                 480

Gly Thr Glu Gly Asp Ala Ser Asn Gly Gly Cys Asp Ala Thr Thr Asp
                485                 490                 495

Leu Ala Asn Gly Gln Pro Gly Phe Lys Ser Asn Met Pro Leu Ala Pro
            500                 505                 510

Gly His Phe
        515

(2) INFORMATION FOR SEQ ID NO:23

(i) SEQUENCE CHARACTERISTICS:
        (A) LENGTH: 466 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:23:

Met Val Phe Leu Ser Gly Asn Ala Ser Asp Ser Ser Asn Cys Thr His
1               5                   10                  15

Pro Pro Pro Pro Val Asn Ile Ser Lys Ala Ile Leu Leu Gly Val Ile
            20                  25                  30

Leu Gly Gly Leu Glu Leu Phe Gly Val Leu Gly Asn Ile Leu Val Ile
            35                  40                  45

Leu Ser Val Ala Cys His Arg His Leu His Ser Val Thr His Tyr Tyr
50                  55                  60
```

-continued

```
Ile Val Asn Leu Ala Val Ala Asp Leu Leu Thr Ser Thr Val Leu
65                  70                  75                  80

Pro Phe Ser Ala Ile Phe Glu Ile Leu Gly Tyr Trp Ala Phe Gly Arg
            85                  90                  95

Val Phe Cys Asn Val Trp Ala Ala Val Asp Val Leu Cys Cys Thr Ala
            100                 105                 110

Ser Ile Met Gly Leu Cys Ile Ile Ser Ile Asp Arg Tyr Ile Gly Val
            115                 120                 125

Ser Tyr Pro Leu Arg Tyr Pro Thr Ile Val Thr Gln Lys Arg Gly Leu
    130                 135                 140

Met Ala Leu Leu Cys Val Trp Ala Leu Ser Val Leu Ile Ser Ile Gly
145                 150                 155                 160

Pro Leu Phe Gly Trp Arg Gln Pro Ala Pro Glu Asp Glu Thr Ile Cys
                165                 170                 175

Gln Ile Asn Glu Glu Pro Gly Tyr Val Leu Phe Ser Ala Leu Gly Ser
            180                 185                 190

Phe Tyr Val Pro Leu Thr Ile Ile Leu Val Met Tyr Cys Arg Val Tyr
        195                 200                 205

Val Val Ala Lys Arg Glu Ser Arg Gly Leu Lys Ser Gly Leu Lys Thr
    210                 215                 220

Asp Lys Ser Asp Ser Glu Gln Val Thr Leu Arg Ile His Arg Lys Asn
225                 230                 235                 240

Ala Gln Val Gly Gly Ser Gly Val Thr Ser Ala Lys Asn Lys Thr His
                245                 250                 255

Phe Ser Val Arg Leu Leu Lys Phe Ser Arg Glu Lys Lys Ala Ala Lys
            260                 265                 270

Thr Leu Gly Ile Val Val Gly Cys Phe Val Leu Cys Trp Leu Pro Phe
    275                 280                 285

Phe Leu Val Met Pro Ile Gly Ser Phe Phe Pro Asp Phe Arg Pro Ser
290                 295                 300

Glu Thr Val Phe Lys Ile Ala Phe Trp Leu Gly Tyr Leu Asn Ser Cys
305                 310                 315                 320

Ile Asn Pro Ile Ile Tyr Pro Cys Ser Ser Gln Glu Phe Lys Lys Ala
                325                 330                 335

Phe Gln Asn Val Leu Arg Ile Gln Cys Leu Arg Arg Lys Gln Ser Ser
            340                 345                 350

Lys His Thr Leu Gly Tyr Thr Leu His Ala Pro Ser His Val Leu Glu
    355                 360                 365

Gly Gln His Lys Asp Leu Val Arg Ile Pro Val Gly Ser Ala Glu Thr
    370                 375                 380

Phe Tyr Lys Ile Ser Lys Thr Asp Gly Val Cys Glu Trp Lys Ile Phe
385                 390                 395                 400

Ser Ser Leu Pro Arg Gly Ser Ala Arg Met Ala Val Ala Arg Asp Pro
            405                 410                 415

Ser Ala Cys Thr Thr Ala Arg Val Arg Ser Lys Ser Phe Leu Gln Val
            420                 425                 430

Cys Cys Cys Leu Gly Pro Ser Thr Pro Ser His Gly Glu Asn His Gln
            435                 440                 445

Ile Pro Thr Ile Lys Ile His Thr Ile Ser Leu Ser Glu Asn Gly Glu
            450                 455                 460

Glu Val
465
```